(12) United States Patent
Takahashi et al.

(10) Patent No.: US 9,206,242 B2
(45) Date of Patent: Dec. 8, 2015

(54) APPLICATION OF ACTIN-BINDING PROTEIN TO DISEASE ASSOCIATED WITH CELL MOTILITY

(75) Inventors: Masahide Takahashi, Nagoya (JP); Atsushi Enomoto, Nagoya (JP)

(73) Assignee: NATIONAL UNIVERSITY CORPORATION NAGOYA UNIVERSITY, Nagoya-shi (JP)

(*) Notice: Subject to any disclaimer, the term of this patent is extended or adjusted under 35 U.S.C. 154(b) by 1703 days.

(21) Appl. No.: 12/085,142

(22) PCT Filed: Nov. 10, 2006

(86) PCT No.: PCT/JP2006/323040
§ 371 (c)(1),
(2), (4) Date: Oct. 21, 2009

(87) PCT Pub. No.: WO2007/060899
PCT Pub. Date: May 31, 2007

(65) Prior Publication Data
US 2010/0050278 A1  Feb. 25, 2010

Related U.S. Application Data

(60) Provisional application No. 60/738,571, filed on Nov. 22, 2005.

(30) Foreign Application Priority Data

Mar. 6, 2006  (JP) .................................. 2006-060330

(51) Int. Cl.
| | |
|---|---|
| *A01K 67/027* | (2006.01) |
| *C07K 16/00* | (2006.01) |
| *C07K 14/47* | (2006.01) |
| *C07K 16/18* | (2006.01) |
| *C12N 15/113* | (2010.01) |
| *C12N 15/85* | (2006.01) |
| *G01N 33/50* | (2006.01) |

(52) U.S. Cl.
CPC ......... *C07K 14/4716* (2013.01); *A01K 67/0276* (2013.01); *C07K 16/18* (2013.01); *C12N 15/113* (2013.01); *C12N 15/8509* (2013.01); *G01N 33/5029* (2013.01); *A01K 2217/075* (2013.01); *A01K 2227/105* (2013.01); *A01K 2267/03* (2013.01); *C12N 2310/14* (2013.01); *C12N 2501/998* (2013.01); *G01N 2333/4703* (2013.01); *G01N 2500/10* (2013.01)

(58) Field of Classification Search
None
See application file for complete search history.

(56) References Cited

U.S. PATENT DOCUMENTS 4,931,385 A * 6/1990 Block et al. .................. 435/7.94

FOREIGN PATENT DOCUMENTS

| WO | WO/01/57190 | * | 9/2001 | ............. C07H 21/04 |
| WO | WO 03/008625 A2 | | 1/2003 | |

OTHER PUBLICATIONS

Lederman et al. (Molecular Immunology 28: 1171-1181, 1991).*
Li et al. (PNAS 77: 3211-3214, 1980).*
Houghten et al. (New Approaches to Immunization, Vaccines 86, Cold Spring Harbor Laboratory, p. 21-25, 1986).*
Falkenberg et al. (J. Clin. Chem. Clin Biochem. 1984, 22:867-82).*
Ridley A., et al.; "Cell Migration: Integrating Signals from Front to Back;" *Science*; 2003; vol. 302; pp. 1704-1709.
Higuchi et al.; "Akt mediates Rac/Cdc42-regulated cell motility in growth factor-stimulated cells in invasive PTEN knockout cells;" *Current Biology*; 2001; vol. 11; pp. 1958-1962.
Merlot S., et al.; "Leading the way: directional sensing through phosphatidylinositol 3-kinase and other signaling pathways;" *Journal of Cell Science*; 2003; vol. 116; pp. 3471-3478.
Enomoto, A. et al.; "Akt/PKB Regulates Actin Organization and Cell Motility via Girdin/APE;" *Developmental Cell*; 2005; vol. 9; No. 3; pp. 389-402.
Enomoto, A. et al.; "Akt ni yoru Saibo Undo no Seigyo Kiko: Shinki Kishitsu Girdin/APE no Dotei to sono Actin Ketsugo Tanpakushitsu to shiteno Kino;" *Cell Technology*; 2005; vol. 24; No. 11; pp. 1192-1193.
Anai, M. et al.; "A Novel Protein Kinase B (PKB)/AKT-binding Protein Enhances PKB Kinase Activity and Regulates DNA Synthesis;" *The Journal of Biological Chemistry*; 2005; vol. 280; No. 18; pp. 18525-18535.
Brazil, D.P. et al.; "PKB Binding Proteins: Getting in on the Akt;" *Cell*; 2002; vol. 111; No. 3; pp. 293-303.
Enomoto, A. et al.; "Girdin/APE, a novel actin-binding protein, regulates actin organization and cell motility via its phosphroylation by Akt;" *Annual Meeting of the Molecular Biology Society of Japan*; 2005; vol. 28; p. 246 (1P-0681).
Anai, M. et al.; "Akt Ketsugo Tanpaku APE no Hatsugen Teika ha Akt Kassei o Teika sase Saibo Zoshoku o Seigyo suru;" *The Journal of the Japan Diabetic Society*; 2005; vol. 48; Supplement 2; p. S-142 (II-6-33).
Anai, M. et al. "A novel Akt-binding protein enhances Akt kinase activity and regulates DNA synthesis and apoptosis;" *Seikagaku*; 2005; vol. 77; No. 8; p. 934 (3P-382).

(Continued)

*Primary Examiner* — Sharon Wen
(74) *Attorney, Agent, or Firm* — Oliff PLC

(57) ABSTRACT

It is intended to identity a protein involved in a molecular mechanism between Akt and cell motility as well as to elucidate its function and find its application. In the present teachings, for achieving the above object, protein or partial peptide thereof containing an amino acid sequence identical or substantially identical to the amino acid sequence represented by SEQ ID: 2 is utilized in the screening of a compound or a salt thereof that activates or inhibits any of cell motility, cell migration and angiogenesis.

45 Claims, 34 Drawing Sheets

(56) References Cited

OTHER PUBLICATIONS

Office Action with translation issued in Japanese Patent Application 2012-011559 mailed Mar. 27, 2012.
Jun. 12, 2012 Office Action issued in Japanese Patent Application No. 2007-546426 (with translation).
Nov. 22, 2011 Notification of Reasons for Rejection issued in Japanese Application No. 2007-546426 with English-language translation.
Ministry of Education, Culture, Sports, Science and Technology, Specific Research, Cancer, Annual Reports, Heisei 15, Version 2004, p. 53-54, 2003.

* cited by examiner

MENEIFTPLL EQFMTSPLVT WVKTFGPLAA GNGTNLDEYV ALVDGVFLNQ VMLQINPKLE
SQRVNKKVNN DASLRMHNLS ILVRQIKFYY QETLQQLIMM SLPNVLIIGK NPFSEQGTEE
VKKLLLLLLG CAVQCQKKEE FIERIQGLDF DTKAAVAAHI QEVTHNQENV FDLQWMEVTD
MSQEDIEPLL KNMALHLKRL IDERDEHSET IIELSEERDG LHFLPHASSS AQSPCGSPGM
KRTESRQHLS VELADAKAKI RRLRQELEEK TEQLLDCKQE LEQMEIELKR LQQENMNLLS
DARSARMYRD ELDALREKAV RVDKLESEVS RYKERLHDIE FYKARVEELK EDNQVLLETK
TMLEDQLEGT RARSDKLHEL EKENLQLKAK LHDMEMERDM DRKKIEELME ENMTLEMAQK
QSMDESLHLG WELEQISRTS ELSEAPQKSL GHEVNELTSS RLLKLEMENQ SLTKTVEELR
TTVDSVEGNA SKILKMEKEN QRLSKKVEIL ENEIVQEKQS LQNCQNLSKD LMKEKAQLEK
TIETLRENSE RQIKILEQEN EHLNQTVSSL RQRSQISAEA RVKDIEKENK ILHESIKETS
SKLSKIEFEK RQIKKELEHY KEKGERASEL ENELHHLEKE NELLQKKITN LKITCEKIEA
LEQENSELER ENRKLKKTLD SFKNLTFQLE SLEKENSQLD EENLELRRNV ESLKCASMKM
AQLQLENKEL ESEKEQLKKG LELLKASFKK TERLEVSYQG LDIENQRLQK TLENSNKKIQ
QLESELQDLQ MENQTLQKNL EELKISSKRL EQLEKENKSL EQETSQLEKD KKQLEKENKR
LRQQAEIKDT TLEENNVKIG NLEKENKTLS KEIGIYKESC VRLKELEKEN KELVKRATID
IKTLVPLRED LVSEKLKTQQ MNNDLEKLTH ELEKIGLNKE RLLHDEQSTD DRYKLLESKL
ESTLKKSLEI KEEKIAALEA RLEESTNYNQ QLRQELKTVK KNYEALKQRQ DEERMVQSSP
PISGEDNKWE RESQETTREL LKVKDRLIEV ERNNATLQAE KQALKTQLKQ LETQNNNLQA
QILALQRQTV SLQEQNTTLQ TQNAKLQVEN STLNSQSTSL MNQNAQLLIQ QSSLENENES
VIKEREDLKS LYDSLIKDHE KLELLHERQA SEYESLISKH GTLKSAHKNL EVEHRDLEDR
YNQLLKQKGQ LEDLEKMLKV EQEKMLLENK NHETVAAEYK KLCGENDRLN HTYSQLLKET
EVLQTDHKNL KSLLNNSKLE QTRLEAEFSK LKEQYQQLDI TSTKLNNQCE LLSQLKGNLE
EENRHLLDQI QTLMLQNRTL LEQNMESKDL FHVEQRQYID KLNELRRQKE KLEEKIMDQY
KFYDPSPPRR RGNWITLKMR KLIKSKKDIN RERQKSLTLT PTRSDSSEGF LQLPHQDSQD
SSSVGSNSLE DGQTLGTKKS SMVALKRLPF LRNRPKDKDK MKACYRRSMS MNDLVQSMVL
AGQWTGSTEN LEVPDDISTG KRRKELGAMA FSTTAINFST VNSSAGFRSK QLVNNKDTTS
FEDIGPQGVS DDSSTGSRVH ASRPASLDSG RTSTSNSMNN ASLHEVKAGA VNNQSRPQSH
SSGEFSLLHD HEAWSSSGSS PIQYLKRQTR SSPVLQHKIS ETLESRHHKI KTGSPGSEVV
TLQQFLEESN KLTSVQIKSS SQENLLDEVM KSLSVSSDFL GKDKPVSCGL ARSVSGKTPG
DFYDRRTTKP EFLRPGPRKT EDTYFISSAG KPTPGTQGKI KLVKESSLSR QSKDSNPYAT
LPRASSVIST AEGTTRRTSI HDFLTKDSRL PISVDSPPAA ADSNTTAASN VDKVQESRNS
KSRSREQQSS

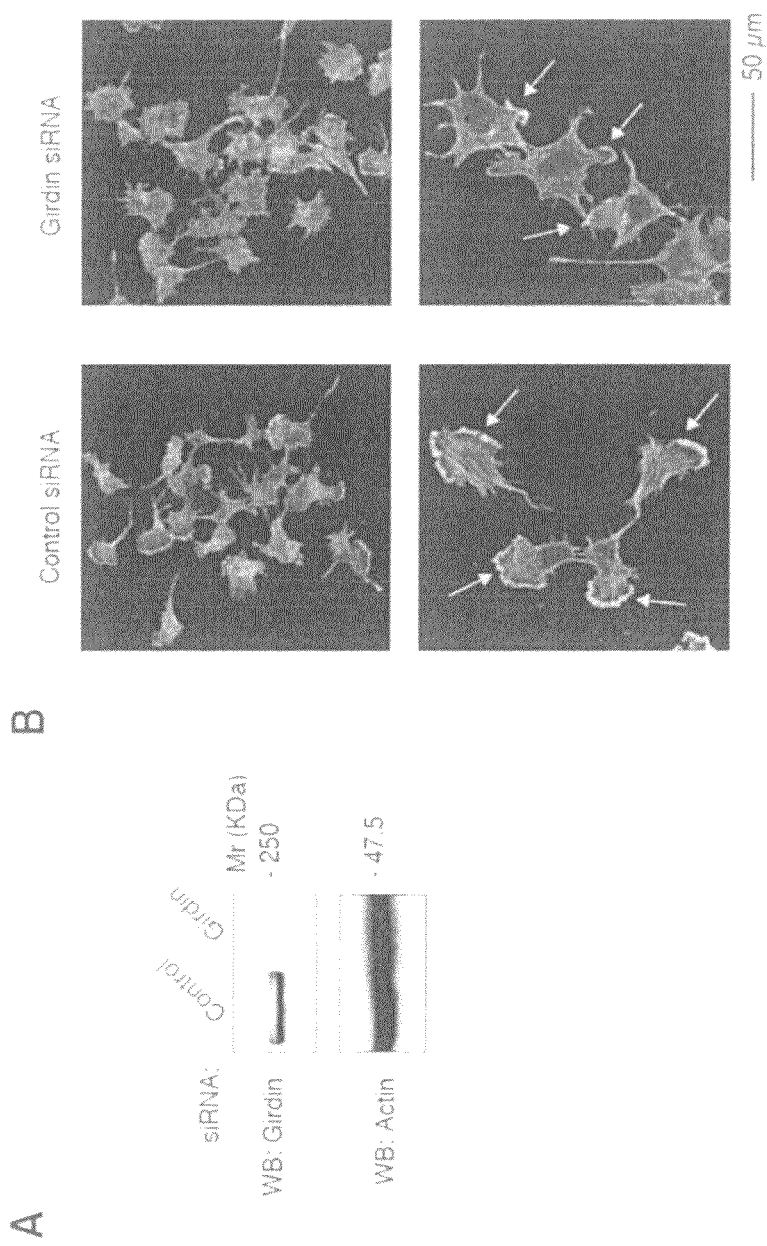

A

B

VEGF 20ng/ml 4hrs
control siRNA Girdin

IB anti-Girdin

APPLICATION OF ACTIN-BINDING PROTEIN TO DISEASE ASSOCIATED WITH CELL MOTILITY

CROSS-REFERENCE TO RELATED APPLICATION

This application claims priority to Japanese patent application No. 2006-060330, filed on Mar. 6, 2006 and U.S. patent application Ser. No. 60/738,571, filed on Nov. 22, 2005, the contents of which are hereby incorporated by reference into the present application.

BACKGROUND OF THE INVENTION

1. Field of the Invention

The present invention relates to an application of Actin-Binding Protein, especially, relates to an application of Actin-Binding Protein Girdin (Akt Phosphorylation Enhancer), a new substrate of serine/threonine kinase, to disease associated with cell motility.

Control mechanism of cell motility is closely associated with morphogenesis in generation, wound healing, and angiogenesis as well as pathological conditions such as cancer cell invasion, arteriosclerosis and immunological disease. A large number of control elements for cell motility including low-molecular G-protein have been identified (Ridley A, et al., Science (2003) 302, p. 1702-1709). Although Akt (also known as Protein Kinase B: PKB) which is serine/threonine kinase is known as an important factor for controlling existence and proliferation of cells, it is also shown in many species such as mammals and cellular slime molds that this factor is essential for cell motility (Higuchi M, et al., Curr. Biol (2001) 11, p. 1958-1962, Merlot S, et al., J. Cell Sci (2003) 116, p. 3471-3478). Malignant tumors which exhibit remarkable expression of Akt tend to show higher invasion.

BRIEF SUMMARY OF INVENTION

However, nothing is known about molecular mechanism by which Akt promotes cell motility. An object of the present invention is therefore to identify a protein involved in molecular mechanism of Akt and cell motility, to elucidate the functions thereof and to attempt utilization thereof.

The present inventors found a novel substrate of Akt using yeast two-hybrid assay, and found that this substrate is an actin-binding protein, whereas its localization is changed to leading edge of moving cells when being phosphorylated by Akt, and, on the other hand, when variants of the actin-binding protein are expressed on the cell, morphology of cells are changed, thereby impairing cell motility dependent on stimulus of proliferation factors. The present inventors further found that this actin-binding protein is essential for integration of actin cellular skeleton and for cell motility, and completed the present invention. That is, the following means are presented according to findings by the present inventors.

(1) A screening method for a compound or a salt thereof that activates or inhibits any of cell motility, cell movement, and angiogenesis, using a protein or a partial peptide thereof containing an amino acid sequence identical with or substantially identical with an amino acid sequence represented by SEQ ID NO: 2.

(2) The screening method according to (1), wherein the protein is a protein consisting of the amino acid sequence represented by SEQ ID NO: 2.

(3) The screening method according to (2), wherein the partial peptide is C-terminal domain (CT1 domain and/or CT2 domain) of a protein including the amino acid sequence represented by SEQ ID NO: 2.

(4) The screening method according to (1) or (2), wherein a serine residue at position 1416 of the amino acid sequence represented by SEQ ID NO: 2 or a serine residue corresponding to the aforesaid serine residue is phosphorylated in the protein.

(5) The screening method according to any of (1) to (4), wherein promotion or inhibition of binding activity with serine/threonine kinase Akt and the protein or a part of the protein containing the amino acid sequence identical with or substantially identical with the amino acid sequence represented by SEQ ID NO: 2 is used as an index.

(6) The screening method according to any of (1) to (4), wherein promotion or inhibition of phosphorylation of the protein by serine/threonine kinase Akt is used as an index.

(7) The screening method according to any of (1) to (4), wherein promotion or inhibition of actin filament binding capability is used as an index.

(8) The screening method according to any of (1) to (4), wherein promotion or inhibition of actin stress fiber forming ability is used as an index.

(9) The screening method according to any of (1) to (4), wherein promotion or inhibition of actin meshwork forming ability in lamellipodia is used as an index.

(10) The screening method according to any of (1) to (4), wherein promotion or inhibition of cell membrane binding is used as an index.

(11) The screening method according to any of (1) to (4), wherein promotion or inhibition of phosphoinositide binding is used as an index.

(12) A screening method for a compound or a salt thereof that activates or inhibits any of cell motility, cell movement, and angiogenesis, using a polynucleotide encoding a protein containing an amino acid sequence identical with or substantially identical with the amino acid sequence represented by SEQ ID NO: 2.

(13) The screening method according to any of (1) to (12), which screening method is for preventive and therapeutic medicine for disorders in which any of cell motility, cell movement, and angiogenesis is involved.

(14) The screening method according to any of (1) to (13), wherein the disorder is any one selected from cancer, Arteriosclerotic disorder, central nervous system damage and peripheral nerve disorder.

(15) A preventive and therapeutic medicine for disorders in which any of cell motility, cell movement, and angiogenesis is involved, wherein the medicine is a compound or a salt thereof expressing one of, or two or more of the following activities for a protein or a partial peptide thereof containing an amino acid sequence identical with or substantially identical with the amino acid sequence represented by SEQ ID NO: 2:

a) Inhibitory activity of binding of serine/threonine kinase Akt and the protein;
b) Inhibitory activity of phosphorylation of the protein by serine/threonine kinase Akt;
c) Inhibitory activity of binding to actin filament;
d) Inhibitory activity of actin stress fiber formation;
e) Inhibitory activity of actin meshwork formation in lamellipodia;
f) Inhibitory activity of cell membrane binding; and
g) Inhibitory activity of binding to phosphoinositide.

(16) A preventive and therapeutic medicine for disorders in which any of cell motility, cell movement, and angiogenesis is involved, wherein the medicine is a compound that suppresses expression level of a protein containing an amino acid sequence identical with or substantially identical with the amino acid sequence represented by SEQ ID NO: 2.

(17) The preventive and therapeutic medicine according to (16), wherein the compound is a polynucleotide or a part thereof having a base sequence complementary to or substantially complementary to a base sequence of a polynucleotide encoding the amino acid sequence represented by SEQ ID NO: 2.

(18) The preventive and therapeutic medicine according to (17), wherein the medicine is an RNA expressing RNA interference.

(19) The preventive and therapeutic medicine according to (16), wherein the medicine is a DNA encoding the RNA according to (18).

(20) The preventive and therapeutic medicine according to (16), which the medicine is a recombinant vector containing the DNA according to (19).

(21) The preventive and therapeutic medicine according to any of (16) through (20), wherein the disorder is any one selected from cancer, Arteriosclerotic disorder, central nervous system damage and peripheral nerve disorder.

(22) A cell in which expression level of a gene encoding a protein containing an amino acid sequence identical with or substantially identical with the amino acid sequence represented by SEQ ID NO: 2 is suppressed.

(23) An animal in which expression level of a gene encoding a protein containing an amino acid sequence identical with or substantially identical with the amino acid sequence represented by SEQ ID NO: 2 is suppressed.

(24) The animal according to (23), wherein suppression of expression level of the gene is made by knockdown.

(25) The animal according to Claim (23) or (24), wherein the animal is for research purpose of disorders associated with any of cell motility, cell movement, and angiogenesis and for screening of preventive and therapeutic medicine.

(26). A qualitative analysis method for a compound or a partial peptide thereof that activates or inhibits any of cell motility, cell movement, and angiogenesis, wherein the quantitative analysis utilizes a reaction between a protein containing an amino acid sequence identical with or substantially identical with the amino acid sequence represented by SEQ ID NO: 2 and serine/threonine kinase Akt.

(27) A quantitative analysis method for a compound or a partial peptide thereof that activates or inhibits any of cell motility, cell movement, and angiogenesis, wherein the quantitative analysis utilizes a reaction between a protein containing an amino acid sequence identical with or substantially identical with the amino acid sequence represented by SEQ ID NO: 2 and serine/threonine kinase Akt.

(28) An antibody specific to a protein or to a partial peptide thereof containing an amino acid sequence identical with or substantially identical with the amino acid sequence represented by SEQ ID NO: 2.

(29) An antibody which is a protein containing an amino acid sequence identical with or substantially identical with the amino acid sequence represented by SEQ ID NO: 2, wherein the protein is specific to a protein where a serine residue at position 1416 of the amino acid sequence represented by SEQ ID NO: 2 or a serine residue corresponding to the aforesaid serine residue is phosphorylated or specific to a partial peptide containing the phosphorylated portion.

(30) A research reagent for activating or inhibiting cell motility, cell movement, and angiogenesis, including the antibody according to (28) or (29).

(31) A diagnostic agent for disorders in which any of cell motility, cell movement, and angiogenesis is involved, including the antibody according to (28) or (29).

(32) A diagnostic method for disorders in which any of cell motility, cell movement, and angiogenesis is involved, utilizing any of the following reactivities for a protein or a partial peptide thereof containing an amino acid sequence identical with or substantially identical with the amino acid sequence represented by SEQ ID NO: 2 in cells of disorder site:
  a) Binding activity of serine/threonine kinase Akt and the protein;
  b) Phosphorylation activity of the protein by serine/threonine kinase Akt;
  c) Binding activity to actin filament;
  d) Actin stress fiber forming activity;
  e) Forming activity of actin meshwork in lamellipodia;
  f) Cell membrane binding activity; and
  g) Binding activity to phosphoinositide.

BRIEF DESCRIPTION OF THE DRAWINGS

FIG. 1h shows a deduced amino acid sequence of Girdin. Residues at positions a and d in the 135 heptad repeats (abcdefg) 135, which are predicted to form an α-helical coiled-coil, are indicated by red and green, respectively. The putative binding site for phosphoinositides is underlined. The box shows the putative Akt phosphorylation site.

FIG. 4e shows knockdown of Girdin affects the formation of the stress fibers and lamellipodia in SK-N-MC cells that express RET tyrosine kinase receptor. (A) shows SK-N-MC (RET) cells were harvested 72 hrs after the start of siRNA transfection. The cell lysates were analyzed by SDS-PAGE, followed by western blot analysis using anti-Girdin and anti-actin antibodies. (B) shows SK-N-MC (RET) cells transfected with siRNAs were stimulated with 50 ng/ml GDNF for 60 min, fixed, and stained with Alexa-488 phalloidin. The Girdin knockdown cells exhibited severe morphological changes with multiple protrusions compared with the control cells. Arrows denote lamellipodia at the leading edge. The Girdin knockdown cells still show the formation of lamellipodia, which is less polarized and extended compared with that of the control cells.

FIG. 6d, (b)) and was subjected to an actin cosedimentation assay. A fixed amount of GST-CT was phosphorylated in vitro and mixed with various amounts of F-actin, followed by ultracentrifugation. The amount of phosphorylated GST-CT bound to F-actin in the pellet fraction was monitored by Western blot analyses with anti-P-Girdin antibody.

DETAILED DESCRIPTION OF THE INVENTION

Figure 1A:
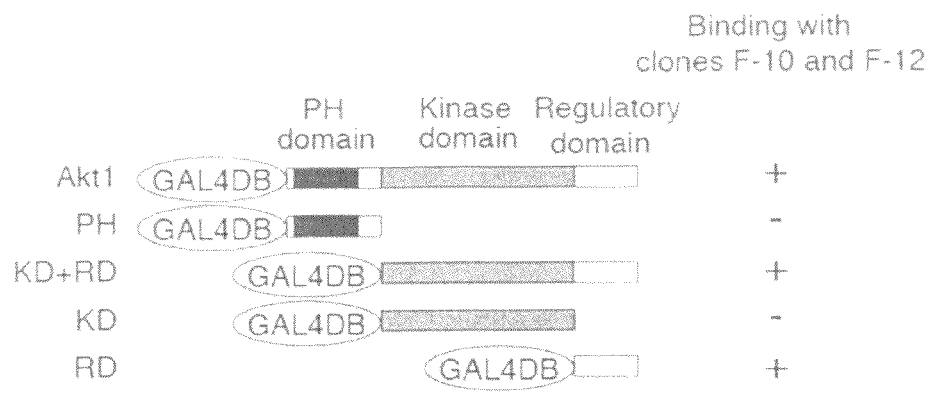
FIG. 1a shows a schematic illustration of respective bait constructs (i.e. expression vectors with various genes integrated) for yeast two-hybrid binding assays. The cDNA fragments corresponding to the indicated domains of human Akt1 were fused in frame to the DNA binding domain of GAL4 transcription factor (GAL4DB) in the pAS2 vector. PH, pleckstrin homology domain; KD, catalytic kinase domain; RD, regulatory domain.
Figure 1B:
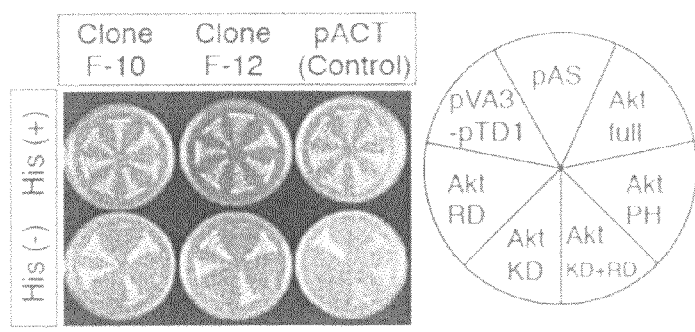
FIG. 1b shows the interactions of clones F-10 and F-12 with human Akt1 in yeast two-hybrid binding assays. pAS, a negative control; pVA3-pTD1, a positive control; His, histidine.

The present invention relates to Girdin, which is a protein referred by the present inventors as 'Girdin', which is to be phosphorylated by serine/threonine kinase Akt (hereafter referred simply as 'Akt'); Girdin is an actin-binding protein, and particularly relates to a protein having the same amino acid sequence as an amino acid sequence represented by SEQ ID NO: 2 (amino acid sequence of Girdin), or a protein including substantially identical amino acid sequence or partial peptide thereof (hereafter, the protein and the partial peptide are collectively referred to as the present protein). Girdin is normally involved in cell motility, cell movement (e.g. migration), and angiogenesis in the process of various parts of the body being formed from human fertilized egg. Specifically, motion and movement of tumor cells are associated with progression, metastasis, invasion of cancers; movement or the like of neuron cells are associated with neurogenesis; and movement of vascular component cells such as vascular endothelial cell are associated with angiogenesis. Therefore, use of the present protein allows searching and provision of preventive and therapeutic medicine effective for disorders in which at least one of cell motility, cell movement, and angiogenesis is involved. Further, the use of the present protein enables diagnosis of these disorders.

The present invention relates, in a relationship between the present protein and Akt, to a compound which promotes or inhibits various activities appearing in cell motility or the like or to salt thereof. Such compound or salt thereof can be utilized as a compound for promoting or inhibiting either of cell motility, cell movement, and angiogenesis, or salt thereof. Since such compound of the present invention is capable of activating or inhibiting either of cell motility, cell movement, and angiogenesis, it is useful, for example, for medical treatment and prevention of disorders in which these cellular kinetics are involved. Further, when a test compound is supplied to the present protein and an action on the present protein is detected, it is possible to perform screening of compounds that are useful as the preventive and therapeutic medicine for disorders associated with cell motility, cell movement, and angiogenesis. Further, since an antibody or the like specific to the present protein allows quantitative measurement or detection of localization of the present protein in cells, diagnosis for prevention and medical treatment of disorders, in which cell motility, cell movement, and angiogenesis are involved, is made possible. The following description explains in detail embodiments of the present invention.

The present protein can include an amino acid sequence identical with or substantially identical with the amino acid sequence represented by SEQ ID NO: 2. Those consisting of these amino acid sequences may be used. As for the amino acid sequence substantially identical with the amino acid sequence represented by SEQ ID NO: 2, amino acid sequence having about 50% or more, preferably about 60% or more, further preferably about 70% or more, more preferably about 80% or more, particularly preferably about 90% or more, most preferably about 95% or more homology. The homology (identity) (%) can be determined using search program (e.g., BLAST, FASTA) which is commonly used in the art at initial setting. Meanwhile, the homology (%) may be determined using optional algorithm known in the art, such as algorithm by Needleman et al, (1970) (J. Mol. Biol. 48: 444-453), Myers and Miller (CABIOS, 1988, 4: 11-17).

The present protein may have an amino acid sequence represented by SEQ ID NO: 2 in which one, two or more (preferably about 1 to 30, more preferably about 1 to 10, further preferably several (e.g. 1 to 5)) amino acids in the amino acid sequence is/are deleted, or amino acid sequence in which the same number of amino acids is/are added, or amino acid sequence in which the same number of amino acids is/are inserted, or amino acid sequence in which the same number of amino acids is/are replaced, or amino acid sequence which is modified by combination of two or more types selected from amino acids in which the same number of amino acids is/are deleted, added, inserted and replaced, or may consist of these amino acid sequences. Site of such amino acid modification is not particularly limited as long as activity of the present protein is not lost.

The protein substantially identical with the amino acid sequence represented by SEQ ID NO: 2 preferably has homogenous activity as the protein including amino acid sequence represented by SEQ ID NO: 2. Homogenous activity denotes that degree of activity is not questioned. Therefore, in some cases, degree of activity is comparable to or less than that of a protein including the amino acid sequence represented by SEQ ID NO: 2; or may be comparable to or more than that. The activity of this sort is, for example, activity as substrate of Akt of the present protein, and in particular, serine at position 1416 in the amino acid sequence represented by SEQ ID NO: 2 or serine at position corresponding to that preferably has activity being phosphorylated by Akt. As for homogenous activity, although above-shown phosphorylating activity is mentioned as preferable one, it is not limited to above-shown activity, and any other activity of the protein including the amino acid sequence represented by SEQ ID NO: 2 may be used, or a combination of 2 or more types may be used. These activities will be discussed later in detail.

Further, as long as the present protein has homogenous activity as the protein represented by SEQ ID NO: 2, it includes partial peptide thereof. Although domain of the partial peptide is not particularly limited, it preferably includes amino acids at position 1376 to position 1870 of the amino acid sequence represented by SEQ ID NO: 2 (CT1 domain and/or CT2 domain), which is CT domain in C-terminal side domain of the protein including the amino acid sequence represented by SEQ ID NO: 2. CT1 domain is the first half portion domain of the amino acid sequence of SEQ ID NO: 2, and preferably includes at least those at position 1389 to position 1407 or sequence corresponding to the amino acid sequence thereof, and also the sequence at positions 1411 to 1416, and for example, it may include amino acid sequence at position 1375 to position 1622. Further CT 2 domain is the second half portion of CT domain and may have, for example, amino acid sequence at position 1623 to position 1870. The partial peptide may have both of domains or only one of them. Preferable CT1 domain has Akt phosphorylation site and at the same time, interacts with cell membrane, and preferable CT2 domain is able to bind actin filament.

As for these proteins, orthologue or homolog of Girdin in human, or proteins artificially modified based on the sequence such as Girdin (NCBI homepage, http://www.ncbi.nlm.nih.gov/, amino acid sequence can be obtained at accession number BAE44387) are mentioned. Further, as a transcriptional variant of Girdin, the protein including amino acid sequence (1843 residues) already described likewise at accession number NP_060554 in NCBI homepage is mentioned.

The present protein includes a protein or partial peptide in such aspect that serine residue at position 1416 of the amino acid sequence represented by SEQ ID NO: 2 or serine residue corresponding to the serine residue is phosphorylated. This phosphorylation is brought about by Akt, and it is inferred that, localization of Girdin is concentrated to leading edge of cells due to the phosphorylation, and Girdin is thereby involved with cell motility. Meanwhile, in cases where nonphosphorylated aspect and phosphorylated aspect should be distinguished specifically, each may hereinbelow be expressed as the present nonphosphorylated protein and the phosphorylated protein respectively.

As for the present protein, although above-shown Girdin that is a naturally-occurring protein including the amino acid sequence represented by SEQ ID NO: 2 is mentioned, the protein or peptide included in the present protein may not include natural amino acids only, and various modifications may be applied thereto within a range in which activity of the present protein is not lost. Various modifications to proteins and amino acids are well known in the art, while, for example, for carboxyl group, either of carboxylate (—COO—), amide (—CONH2) or ester (—COOR) may be used. As for R in the ester, for example, C1-6 alkyl group such as methyl, ethyl, n-propyl, isopropyl, n-butyl; C3-8 cycloalkyl group such as cyclopentyl, cyclohexyl; C6-12 aryl group such as phenyl, α-naphthyl; phenyl C1-2-alkyl group such as benzil, phenethyl; or C7-14 aralkyl group such as α-naphthyl-C1-2 alkyl group such as α-naphthylmethyl; and pivaloyl oxymethyl group may be used. When the protein used in the present invention has carboxyl group (or carboxylate) at positions other than C-terminal, those in which carboxyl group is amidated or esterified are included in the protein used in the present invention. In this case, C-terminal ester mentioned above or the like is used for the ester. Further, amino group such as amino acid residue at N-terminal (e.g., methionine residue) may be protected by protecting group (e.g., C1-6 acyl group such as C1-6 alkanoyl such as formyl group, acetyl group), such one in which N-terminal glutamine residue produced being cut in vivo is pyroglutamated may be used, substituted group on the side chain of amino acid in the molecule (e.g., —OH, —SH, amino group, imidazole group, indole group, guanidino group) may be protected by appropriate protecting group (e.g., C1-6 acyl group such as C1-6 alkanoyl group such as formyl group, acetyl group), and so-called glycoprotein in which sugar chains are bound may be used.

Meanwhile, in the present protein which is not phosphorylated, in the serine at position 1416 of the amino acid sequence represented by SEQ ID NO: 1 or serine corresponding thereto, phosphorylation by Akt is modified in a possible range.

The present protein may be a form of salts. For example, salts with physiologically acceptable acids (e.g., inorganic acid, organic acid) and with bases (e.g., alkaline metal) are used, while physiologically acceptable acid addition salt is preferable. As for such salts, for example, salts with inorganic acid (e.g., hydrochloric acid, phosphoric acid, hydrobromic acid, sulfuric acid) or salts with organic acid (acetic acid, formic acid, propionic acid, fumaric acid, maleic acid, succinic acid, tartaric acid, citric acid, malic acid, oxalic acid, benzoic acid, methanesulfonic acid, benzenesulfonic acid) are used.

The present protein can be acquired by conventional known method. Since the present protein is a ubiquitous protein present in mammalian cells, it can also be acquired from these cells or tissues containing these cells by known protein purification method. Moreover, the present protein can be obtained such that DNA encoding the present protein is acquired, transfectant containing the DNA is produced and incubated. The protein can be purified and isolated by ammonium sulfate precipitation, ethanol precipitation, acid extraction, a combination of chromatographies such as ion exchange chromatograph, hydrophobic chromatography, hydroxy apatite chromatography, reverse phase chromatography, and gel filtration chromatography. Further, in some cases, the protein of present invention can be synthesized by known solid-phase synthesis method of peptides (H. Yajima, S. Sakakibara; Jikken Kagaku Koza 1 (Courses in Experimental Chemistry), Chemistry of proteins, IV, 205, 1977). Protection of functional group used for peptide synthesis, protecting group and desorption of the protecting group, activation of the functional group involved in reactions, or the like may be performed by selecting from known groups or known techniques appropriately. Further, as will be described later, the present protein can be acquired through incubation of cells retaining foreign DNA which expresses the present protein or from cells and tissues of transgenic animals retaining the foreign DNA.

Next, activity of the present protein, namely, activity of Girdin that is a protein including the amino acid sequence represented by SEQ ID NO: 2 will be explained. Girdin has the following activities and the present protein has either of these activities. That is, either of the following activities: (1) Activity as the substrate of Akt (serine at position 1416 in SEQ ID NO: 2 or serine at the site corresponding thereto is phosphorylated by Akt of the present protein), (2) Actin binding protein activity (binds to actin filament to cause cross-linking thereof), and (3) Cell membrane binding activity. Akt substrate activity of (1) is understood as binding with Akt (formation of compound material) and phosphorylation by Atk, actin binding protein activity of (2) is understood as actin stress fiber formation by the present protein or formation of actin meshwork in lamellipodia, and cell membrane binding activity of (3) is understood as binding to phosphoinositide in the cell membrane (interaction).

According to the present inventors, it is already confirmed that various activities as mentioned in (1) to (3) associate with cell motility control by Akt, as consequently associate with cell movement and angiogenesis, and contribute to activation and promotion of cell kinetics thereof. Meanwhile, activities of above-shown (1) and (3) are activities of Girdin that is not phosphorylated yet, and activity of (2) is activity that Girdin possesses regardless of presence or absence of phosphorylation. These various activities can be detected by in vitro or in vivo experimental system as will be explained in detail later in Embodiments.

(Nucleotide Encoding the Present Protein)

In the present invention, nucleotide encoding the protein having an amino acid sequence identical or substantially identical with the amino acid sequence represented by SEQ ID NO: 2 or partial peptide thereof is not particularly limited as long as it has base sequence encoding each of proteins. The nucleotide can be used as DNA, RNA, DNA/RNA chimera having these base sequences and may be single-strand or double-strand. In double-stranded case, DNA/RNA hybrid may be used as well as DNA double-stranded and RNA double-stranded. In single stranded case, either of sense strand and antisense strand may be used. In particular, nucleotide of this sort can be acquired in the form of genome DNA, cDNA, mRNA or PCR product, chemical synthesis DNA, or the like.

As the base sequence encoding the amino acid sequence represented by SEQ ID NO: 2, a base sequence represented by SEQ ID NO: 1 may be employed. This base sequence is a base sequence encoding Girdin. As mentioned above, the nucleotide encoding the present protein is not limited to the base sequence identical with the base sequence represented by SEQ ID NO: 1 and may be a base sequence encoding the same amino acid sequence with the use of codon usage which is different from this base sequence. Further, the base sequence of the present nucleotide may be a nucleotide of DNA or the like that hybridizes the base sequence represented by SEQ ID NO: 1 under stringent conditions or a nucleotide encoding a protein having homogenous activity as the present protein.

As for DNA capable of being hybridized under stringent conditions, for example, DNA containing a base sequence having about 50% or more, preferably about 60% or more, further preferably about 70% or more, more preferably about 80% or more, particularly preferably about 90% or more, most preferably about 95% or more homology with the base sequence represented by each sequence number is used. Hybridization can be performed according to known method or a method in conformance with the same, for example, the method described in Molecular Cloning 2nd (J. Sambrook et al., Cold Spring Harbor Lab. Press 1989). Further, in cases where commercially available library is used, hybridization can be performed according to the instruction manual attached thereto. More preferably, hybridization can be performed according to high-stringent conditions. High-stringent conditions denote, for example, sodium concentration of about 19 to 40 mM, preferably about 19 to 20 mM, temperature of about 50 to 70° C., preferably about 60 to 65° C. In particular, the most preferable conditions are sodium concentration of about 19 mM and temperature of about 65° C.

As for a nucleotide encoding Girdin, for example, nucleotide having the base sequence represented by SEQ ID NO: 1, or such having base sequence hybridizing with the base sequence represented by SEQ ID NO: 1 under high-stringent conditions and encoding a protein having homogenous activity as the protein represented by SEQ ID NO: 2 may be used.

The nucleotide encoding the present protein can assume a form of nucleic acid construct for transformation. In other words, it can assume various forms (Naked DNA, various expression vectors, artificial chromosome, or the like) as the nucleic acid construct for expressing the present protein in host cells such as mammalian cells. Such nucleic acid construct can appropriately possess various elements such as promoter, terminator to allow expression of the present invention.

(Antibody Specific to the Present Protein)

An antibody specific to the present protein is an antibody specific to a protein including an amino acid sequence identical with or substantially identical with the amino acid represented by SEQ ID NO: 2 such as Girdin or a protein including an antibody specific to partial peptide thereof, and an antibody specific to a protein including an amino acid sequence identical with or substantially identical with the amino acid sequence represented by SEQ ID NO: 2 such as phosphorylated Girdin, such as a protein where serine residue at position 1416 of the amino acid sequence represented by SEQ ID NO: 2 or serine residue corresponding to the serine residue is phosphorylated or partial peptide containing the phosphorylated portion.

The antibody of the present invention may be polyclonal antibody or monoclonal antibody. The antibody can be acquired from a warm-blooded animal after an appropriate antigenic substance is given to the warm-blooded animal to produce antibody, while monoclonal antibody can be acquired from monoclonal producing hybridoma finally generated.

The polyclonal antibody can be produced such that, for example, a compound material of an antigen (protein antigen) with immunogenicity and carrier protein is produced, a warm-blooded animal is then immunized appropriately, polyclonal antibody containing substance is collected from the warm-blooded animal, and isolation and purification of the antibody is carried out. Although conventionally known ones may be used as the carrier protein, bovine serum albumin, bovine thyroglobulin, hemocyanin, or the like may be used, and the compound material may be formed with an immunogen with appropriate ratio. As for coupling of haptene and carrier, in general, glutaraldehyde and carbodiimide, maleimide active ester, thiol group, active ester reagent containing dithiopyridyl group may be used. For administration of such compound material, complete Freund's adjuvant or incomplete Freund's adjuvant can be administered appropriately at the same time. The administration can be normally performed once every 2 to 6 week, a total of about 3 to 10 times. The polyclonal antibody can be collected from blood, peritoneal effusion, or the like of the warm-blooded animal that is immunized by above-shown method, preferably from the blood. Determination of polyclonal antibody titer in the antiserum may be performed appropriately using EIA such as ELISA, and isolation and purification of the antibody may be performed according to known isolation and purification method of the antibody.

A monoclonal antibody can be obtained such that, for example, a warm-blooded animal is immunized with a similar manner as production of the polyclonal antibody, individuals which showed antibody titer are selected, spleen or lymph node is collected therefrom appropriate number of days after the final immunization, antibody producing cells contained therein are caused to be fused with myeloma to prepare monoclonal antibody producing hybridoma, the monoclonal antibody producing hybridoma after screening is incubated, and monoclonal antibody is isolated and purified from the culture. Meanwhile, conventional known method may be used for cell fusion operation and selection of monoclonal antibody.

The antibody of the present invention can be a form of being immobilized to a carrier. A form of the carrier is not particularly limited, and beads-shape, flat-plate-shape, microtiter plate, or the like may be used. The antibody immobilized to the carrier in beads-shape can be utilized for immunoprecipitation, affinity chromatography, or the like, and flat-plate-shape carrier, the antibody immobilized to microtiter plate, or the like may be used as an antibody array or EIA or RIA assay plate in ELISA or the like.

(Nucleotide Having Base Sequence Complementary to or Substantially Complementary to Base Sequence of Nucleotide Encoding the Present Protein or a Part Thereof)

As one nucleotide of this aspect, anti-gene nucleotide (preferably DNA) against DNA encoding the present protein such as Girdin or antisense nucleotide (preferably RNA) against mRNA encoding the present protein may be mentioned. These nucleotides can have various aspects similar to the nucleotide encoding the present protein, and various modification can be employed without being limited to their length and modification such as base and saccharide portion as long as they are able to suppress expression of the present protein. Here, "complementary base sequence" denotes, for example, base sequence having about 40% or more, preferably about 60% or more, further preferably about 80% or more, further preferably about 90% or more homology with entire base sequence or partial base sequence of DNA or mRNA encoding the present protein or partial peptide may be given as examples. In particular, of total base sequence of DNA or mRNA of the present invention, antisense DNA having about 40% or more, preferably about 60% or more, further preferably about 80% or more, further preferably about 90% or more homology with the base sequence encoding N-terminal site of the protein of the present invention (e.g., base sequence around start codon) is preferable. These antisense DNAs can be produced using the known DNA synthesis apparatus.

Further, as one other nucleotide of this aspect, nucleotide expressing RNA interference for gene transcription product encoding the present protein such as Girdin may be used Such nucleotide is constructed such that at least a part of transcription product such as mRNA of DNA encoding the present protein, particularly Girdin, is targeted, thereby allowing suppression of expression of Girdin. One aspect of such nucleotide is a nucleotide having double-stranded structure of oligoribonucleotides hybridizing each other. Specifically, relatively shorter double-stranded oligoribonucleotides (small interfering RNA: siRNA) each having, or not having, a protruded 3'-terminal, and single oligonucleotide (short hairpin RNA: shRNA) which forms (or has) hairpin structure may be mentioned as such. Meanwhile, single-strand oligoribonucleotide which does not form hairpin structure can also develop RNA interference.

Although length of the double-strand pairing sense sequence and antisense sequence in the nucleotide of the present aspect is not particularly limited as long as RNA interference effect is obtained, it is preferably 50 base pairs or less, typically 13 to 28 base pairs preferably, more preferably in a range of 13 to 27 base pairs, further preferably 19 to 21 base pairs. Most preferably, it is 19 or 20 base pairs. Sense sequence and antisense sequence including 3'-side structure not forming double-strand is typically 15 to 30 nt preferably, more preferably in a range of 15 to 29 nt, further preferably 21 to 23 nt. Most preferably, it is 21 or 22 nt. Further, 3'-terminal protruding in siRNA is preferably 2 to 4 nt, more preferably 2 nt. Further, loop site in shRNA may have such a loop site length not disturbing formation and maintenance of double-strand (stem in shRNA) and 3'-terminal structure of such aspect.

siRNA and shRNA may be designed based on a target sequence which is determined by applying appropriately rules disclosed. Further, designing of siRNA including target sequence determination method can be performed by applying appropriately various rules already disclosed, such as: http://design.rnai.jp/sidirect/index.php, http://www.rockefeller.edu/labheads/tuschl/sirna.html and Rational siRNA design for RNA interference (Nature Biotechnology, vol. 22, 326-330 (2004), Angela Reynolds, Devin Leake, Queta Boese, Stephen Scaringe, William S Marshall & Anastasia Khvorova), Improved and automated prediction of effective siRNA (Biochem Biophys Res Commun. 2004 Jun. 18; 319 (1):264-74, Chalk A M, Wahlestedt C, Sonnhammer E L.).

The nucleotide expressing RNA interference can employ various modifications, while modifications of base and saccharide portion are not particularly limited.

(Nucleotide Encoding Nucleotide Expressing RNA Interference)

According to the present invention, it is possible to include nucleotide (preferably DNA) encoding nucleotide expressing RNA interference for gene transcription product encoding the present protein such as Girdin and a vector containing this nucleotide. In other words, this is an aspect of the vector encoding siRNA and shRNA to allow expression for gene transcription product encoding the present protein. The nucleotide of such aspect can realize RNA interference with continuity and is preferable in that knockdown animals can be produced. In such aspect, shRNA expression vector can constitute other loop sequence of antisense sequence and sense sequence so that continuous single-strand RNA capable of constructing shRNA by intracellular transcription may be transcribed. Further, siRNA expression vector may be constituted so that RNA having a predetermined sense sequence and antisense sequence are transcribed. In the siRNA expression vector, sense sequence and antisense sequence may be configured to be expressed by single vector, or each to be expressed by different vectors.

The expression vector can assume aspects of plasmid vector or virus vector. The expression vector can be selected corresponding to cells to be introduced regardless of the types of vectors. For example, as for mammal cells, virus vectors such as retrovirus vector, adenovirus vector, adeno-associated virus vector, vaccinia virus vector, lentivirus vector, herpesvirus vector, alpha-virus vector, EB-virus vector, papilloma virus vector, foamy virus vector may be employed. As for promoters used for these expression vectors, either pol II family or pol III family may be used as long as it is capable of producing a corresponding RNA from each of above-shown DNAs.

(Cells)

The present invention, as one aspect thereof, includes a cell, in which expression level of gene encoding protein having amino acid sequence identical with or substantially identical with the amino acid sequence represented by SEQ ID NO: 2 such as Girdin is suppressed. This cell can be acquired by introducing knockout vector produced based on the base sequence encoding the present protein or nucleotide expressing above-shown RNA interference or nucleotide (vector) encoding the nucleotide into the cell, or from nonhuman mammal knockout animals or nonhuman mammal knockdown animals, which will be dealt with later.

The present invention, as one other aspect, includes a cell, in which foreign DNA encoding protein including amino acid sequence identical with or substantially identical with the amino acid sequence represented by SEQ ID NO: 2 such as Girdin is retained. Such cell can be obtained by introducing a nucleic acid construct for expression of the present protein into the cell or from nonhuman mammal transgenic animals as the acquirement source, which will be dealt with later.

Further, the present invention, as one other aspect, includes a cell, in which foreign DNA encoding the present mutant type protein, in which protein including amino acid sequence identical with or substantially identical with the amino acid sequence represented by SEQ ID NO: 2 such as Girdin is mutated, is retained. Such cell can be obtained by introducing the nucleic acid construct for expression of the present mutant type protein into the cell or from nonhuman mammal transgenic animals as the acquirement source, which will be dealt with later.

Each of these various cells can be human cell (cases where transgenic animal, knockout animal and knockdown animal are used as the acquirement source are excluded) and nonhuman mammal cell. These may be nonhuman mammal embryo-stem cells including rodents such as mouse, rat, or somatic stem cell or body cell. Further, target cell of disorders such as neuron cell, vascular endothelial cell, cancer cell to which the present protein is involved may be used. Each of various cells of the present invention as mentioned is useful for screening and assessment of preventive and therapeutic medicine of the present invention, and assessment of cell motility or the like.

Hereafter, applications of the present protein and of nucleotide, antibody, cell or the like obtained in association with the present protein will be explained.

(A Preventive and Therapeutic Medicine for Disorders in Which the Present Protein is Involved)

The present protein can have aforementioned any activities as mentioned in (1) to (3), these activities relate to promoting cell moiety, cell movement, and angiogenesis. Therefore, compounds or salts thereof which suppress any or two or more activities as mentioned in (1) to (3) of the present protein can be utilized as preventive and therapeutic medicines for disorders in which the present protein including Girdin is involved. The disorders include any disorders which cell motility, cell movement, and angiogenesis is involved. Further, compounds or salts thereof that suppress expression of the present protein can be utilized as preventive and therapeutic medicines for disorders related to cell motility, cell movement, and angiogenesis in which the present protein including Girdin is involved.

Here, disorders associated with any of cell motility, cell movement and angiogenesis include all disorders associated with these phenomena, and the following disorders may be exemplified:

(1) Cancer

For example, primary, metastatic or recurrent breast cancer, prostate cancer, pancreatic cancer, stomach cancer, pulmonary cancer, large intestine cancer (colon cancer, rectal cancer, anus cancer), esophageal cancer, duodenal cancer, head and neck cancer (tongue cancer, pharyngeal cancer, larynx cancer), cerebral tumor, neurilemmoma, non-small cell lung cancer, lung small cell cancer, hepatic cancer, kidney cancer, bile duct cancer, uterus cancer (uterine body cancer, uterine cervix cancer), ovary cancer, bladder cancer, skin cancer, vascular neoplasm, malignant lymphoma, malignant melanoma, thyroid cancer, bone tumor, vascular neoplasm, angiofibroma, retinal sarcoma, penile cancer, pediatric solid cancer, Kaposi's sarcoma, Kaposi's sarcoma resulting from AIDS, maxillary sinus tumor, fibrous histiocytoma, leiomyosarcoma, rhabdomyosarcoma, liposarcoma, uterine myoma, osteoblastoma, bone sarcoma, chondrosarcoma, carcinomatous mesothelioma, tumor such as leukemia, Hodgkin's disease.

(2) Arteriosclerotic Disorder

For example, ischemic syndrome (e.g., acute cardiac infarction, instable angina pectoris), peripheral arterial obstruction, coronary artery intervention (percutaneous transluminal coronary angioplasty (PTCA), atherectomy (DCA)), recurrent stenosis after stent placement, recurrent stenosis after coronary-artery bypass surgery, intervention in other peripheral artery (e.g., angioplasty, atherectomy, stent placement), recurrent stenosis after bypass surgery, ischemic disorder (e.g., cardiac infarction, angina), myocarditis, intermittent claudication, lacunar infarct, arterial sclerosis (e.g., atherosclerosis), cardiac failure (acute cardiac failure, chronic cardiac failure including congestive cardiac failure), abnormal heart rhythm, progression of arterial sclerosis nest, thrombosis, hypertension, hypertensive ear tinnitus, hypotension.

(3) Central Nervous System Damage and Peripheral Nerve Disorder

For example, head injury, spinal cord injury, brain edema, sensory role disorder, sensory role abnormality, autonomic dysfunction, abnormal autonomic function, whiplash injury.

As indexes for obtaining a compound or salt thereof which can be used as a preventive medicine and a therapeutic medicine of the present invention, in particular, activities inhibiting the following activities may be used. a) and b) shown below associate with inhibition of Akt substrate activity of above-shown (1), c) to e) associate with inhibition of actin binding protein activity of above-shown (2), f) and g) associate with inhibition of cell membrane binding activity of above-shown (3).

a) Binding of serine/threonine kinase Akt and the protein
b) Phosphorylation of the protein by serine/threonine kinase Akt
c) Binding to actin filament
d) Formation of actin stress fiber
e) Formation of actin meshwork in lamellipodia
f) Binding to cell membrane
g) Binding to phosphoinositide Compounds having these inhibitory activities can be obtained based on the screening method for acquiring compounds inhibiting above-shown a) through g) as will be described later. For such compounds, antibodies specific to the present invention or the like are given as examples. Further, a variant of the present protein having variation at phosphorylation site by Akt (e.g., Girdin) or a variant of the present protein having variation at phosphoinositide binding site (e.g., Girdin) may be used.

For salts of these compounds, salts with physiologically acceptable acids (e.g., inorganic acid, organic acid) or with bases (e.g., alkaline metal) are used, and physiologically acceptable acid addition salts are particularly preferable. For such salts, for example, salts with inorganic acid (e.g., hydrochloric acid, phosphoric acid, hydrobromic acid, sulfuric acid) or salts with organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) are used.

In the cases where the compound or salt thereof obtained by the screening method is used as the preventive and therapeutic medicine of the present invention, pharmaceutical formulation thereof is not limited particularly. Any formulation such as oral agent, parenteral agent such as injectable solution, injected agent, topical agent suited for topical application or the like may be employed. For example, tablet noncoated or sugar coated if necessary, capsules, elixir, microcapsules may be used orally, or parenterally in the form of injectable solution such as aseptic solution with pharmaceutically acceptable solution other than water, or suspension agent. Various pharmaceutical preparations as mentioned are examples of the embodiments of the preventive and therapeutic medicine of the present invention. These may be manufactured by mixing with, for example, physiologically acceptable carrier, flavouring agent, excipient, vehicle, antiseptic agent, stabilizer, binder or the like by unit dose required by generally accepted pharmaceutical preparation. The amount of active ingredient in these pharmaceutical preparations is such that an appropriate dosage within specified limit is obtained. Meanwhile, for various additives to obtain above-shown pharmaceutical preparation, those known in the art may be selected appropriately and used. Pharmaceutical preparations thus obtained may be administered to nonhuman animals such as rat, mouse, guinea pig, rabbit, bird, sheep, swine, bovine, equine, cat, dog, monkey or the like, in addition to human. Dosage of the above-shown compounds may be set considering symptom, individual difference of the patient or the like.

For the preventive and therapeutic medicine of the present invention, a compound that suppresses expression level of the present protein or salt thereof may be used as well as compounds being screened. For the compound that suppresses expression level in cells of the present protein or salt thereof, nucleotides in various aspects contained in "nucleotide having base sequence complementary to or substantially complementary to base sequence of nucleotide encoding the present protein or a part thereof" are mentioned. Since these nucleotides suppress expression of the present protein in cells by anti-gene, anti-sense, RNA interference, they can inhibit above-shown a) through g) as a result, suppress cell motility, cell movement and angiogenesis due to above-shown a) through g), and they can eventually act as the preventive and therapeutic medicine for disorders associated with any of these.

Compounds or salts thereof that suppress expression of the present protein include DNA constructs that can knockout the genes coding the present proteins. The DNA constructs are can be prepared based on base sequences of polynucleotides coding the present proteins.

Introduction of the preventive and therapeutic medicine containing such nucleotide construct into cells is made much easier when an appropriate carrier is contained therein. For this reason, the preventive and therapeutic medicine of the present invention includes those containing such carriers. As for the carrier, vector, liposome, metallic particle, positive charge polymer, calcium phosphate, DEAE dextran suited for introduction into cells may be employed. Further, for the carrier, any of liposome, metallic particle, positive charge polymer, calcium phosphate or DEAE dextran supporting the vector which retains the nucleotide or the like of the present invention may be used. As for the vector for introduction into cells, nonviral vector or viral vector may be used. Furthermore, the preventive and therapeutic medicine may contain ordinary pharmaceutically acceptable carrier, excipient, binder, stabilizer, buffering agent, solubilizing agent, isotonic agent or the like.

Administration is not particularly limited as long as introduction into a target cell is accomplished and suppression of expression level of the present protein could be realized, while the following methods are mentioned. That is, ex vivo method in which gene of the present invention is introduced in vitro to each of cells such as fibroblastic cell, cells which succeeded gene introduction (cells of the present invention) are selected and then transplanted to a target site, and an approach in which local infusion is attempted directly to the target site with the use of viral vector or liposome to allow introduction of the gene of the present invention in vivo. Further, such a method is mentioned that sustained-release dosage form is prepared and is embedded close to the affected area. As for the method for introducing the preventive and therapeutic medicine containing such nucleotide construct into cells or tissues, phosphoric acid-calcium coprecipitation method; nucleic acid direct infusion method using a micro glass tube; gene introduction by inclusive type liposome; gene introduction method by static electricity type liposome; HVJ-liposome method, improved version of HVJ-liposome method (HVJ-AVE liposome method); receptor-mediated gene introduction method; method for transferring nucleic acid molecule into cells together with carrier (metallic particle) by a particle gun; direct introduction of naked-DNA; introduction by positive charge polymer, or the like may be utilized.

The preventive and therapeutic medicine containing such nucleotide construct can be set appropriately within a range where expression level of the present protein is reduced according to administration purpose, age, body weight, symptom of an individual.

(Prevention and Therapeutic Method of Disorders to Which the Present Protein is Involved)

The preventive and therapeutic medicine of the present invention can be used for prevention and therapeutic method of disorders in which any of cell motility, cell movement and angiogenesis is involved. In other words, administration of effective dose of the preventive and therapeutic medicine of the present invention to human or nonhuman warm-blooded animal for prevention and medical treatment is considered to be the prevention method and therapeutic method of above-mentioned disorders.

(Screening Method)

According to the present invention, a method for screening a compound, which promotes or inhibits various activities of the present protein, or increases or decreases expression level of the present protein or salt thereof, which uses the present protein and nucleotide encoding the present protein, is provided. The compound obtained by the screening method or salt thereof can be used as a compound for activating or inhibiting any of cell motility, cell movement and angiogenesis. Further, the compound which inhibits various activities of the present protein or reduces expression level or salt thereof can be used as preventive and therapeutic medicine for disorders to which the present protein is involved, and can also be used particularly as preventive and therapeutic medicine for disorders to which any of cell motility, cell movement and angiogenesis is involved.

With the present screening method, the compound which promotes or inhibits activity of the present protein or salt thereof can be obtained, while a test compound is supplied to the present protein and cells expressing the present protein, whether above-shown activities (1) through (3) of the present protein, specifically above-mentioned (a) through (g), are promoted or inhibited are used as indexes, as compared with a case where the test compound is not supplied. Further, when the test compound is supplied to cells expressing the present protein, and detection, whether expression level of the present protein is increased or decreased as compared with a case where the test compound is not supplied, is possible, it is possible to obtain a compound which increases or decreases expression level of the present protein or salt thereof. Meanwhile, as for the test compound supplied to the screening system at detection of the action, other than the one acting on the present protein, nucleotide encoding the present protein or one acting on the nucleotide may be used. Since the compound which inhibits above-shown activities of the present protein or reduces expression level of the present protein or salt thereof suppresses cell motility, cell movement and angiogenesis, they can be used as the preventive and therapeutic medicine for disorders to which any of these cell kinetics is involved.

For such test compound, for example, peptide, protein, nonpeptide compound, synthetic compound, fermented product, cell extraction liquid, botanical extraction liquid, animal tissue extraction liquid, gene (genome DNA, cDNA) may be employed, and these compounds may be novel compound or known compound.

In the screening method, for detection of expression level of the present protein and various indexes of above-shown a) through g), the following methods may be employed. For example, in order to use binding with the present protein, which is not phosphorylated with Akt, as the index, phosphorylation of the present protein not phosphorylated by Akt is preferably used as the index, and for example, the test compound is supplied to in vitro kinase assay system including active type Akt that is, for example, constitutive active with Girdin (that may be obtained from purifying, by using tag, cell lysate from COS7 cell expressing tagged Girdin) and ATP labeled by P32 or the like, and incubated, and phosphorylation oxide thereby obtained can be detected by autoradiography. Alternatively, EGF is added to a cell expressing Girdin and Akt is activated, while at the same time, the test compound is supplied and incubated; after which the cell lysate is then subjected to immunoprecipitation by Girdin antibody, further subjected to immunoprecipitation by phosphorylated Girdin antibody, and Western blotting analysis is performed by anti-phosphorylation Girdin antibody or the like. Further, in cases where binding to actin filament of the present protein is used as the index, the test compound is supplied to actin coprecipitation assay system containing CT2 domain of Girdin, that is tagged by GST or the like, or Girdin, and incubated, and proteins to be coprecipitated are then collected, separated by SDS-PAGE, and then Western blot analysis is performed using Coomassie brilliant blue (CBB), anti-GST antibody (Cell Signaling Technology) or anti-phosphorylation Girdin antibody. Further, when actin stress fiber formation is used as the index, stimulus for activating Akt such as EGF and the test compound are added to the cell expressing Girdin, Girdin expressing cell is subjected to immunostaining using anti-phosphorylation Girdin antibody that specifically recognizes phosphorylated Girdin to allow observation of formation of actin mesh work by phosphorylated Girdin, or further, phosphorylated Girdin at leading edge may be detected by immunostaining by means of damage healing assay by which a damage is given by scratching to the cell expressing Girdin by supplying the test compound to single-layer cell culture in confluent state. Phosphorylated Girdin at the leading edge is present in the actin meshwork. Further, the cell expressing Girdin may be detected in the form of cell movement in Boyden's chamber method. Further, when binding to cell membrane or phosphoinositide is used as the index, the test compound is supplied to assay system of protein (including Girdin with added tag)-lipid overlay method, protein bound to phosphatide is detected, or the test compound is supplied to the cell expressing Girdin and Girdin may be observed using anti-Girdin antibody.

For a compound obtained by the screening method or salt thereof, an antibody specifically binding to the present protein may be considered. Further, a compound which suppresses binding activity with Akt by changing steric structure of phosphorylated site of the present protein or suppresses phosphorylation of Akt by reducing stability or the like of compound material of Akt-present protein, and Akt inhibitor which reversibly binds to substrate binding site of Akt may be given as the example thereof. Furthermore, a compound or a salt thereof which inhibit cross-linking of the present protein for actin filament or promote releasing of cross-linking state; a compound or salt thereof which inhibit actin stress fiber formation or promote actin stress fiber releasing; a compound or salt thereof which inhibit actin meshwork formation in lamellipodia or promote its releasing; a compound or salt thereof which inhibit cell membrane binding or promote binding releasing; a compound or salt thereof which inhibit binding to phosphoinositide or promote binding releasing may be given as the example. Further, as previously explained, various nucleotide constructs suppressing expression of the present protein by knockout or knockdown may also be utilized.

(Transgenic Animal)

According to the present invention, nonhuman mammal having foreign DNA encoding the present protein is provided. This transgenic animal expresses the present protein by foreign DNA and is therefore suited for study on activities of the present protein, screening and assessment of the preventive and therapeutic medicine for disorders to which the present protein is involved. Here, as non-human mammals, for example, bovine, swine, sheep, goat, rabbit, dog, cat, guinea pig, hamster, mouse, rat are used. Of them, rodents such as mouse and rat are preferable.

Transgenic animals can be obtained such that the foreign DNA or the like is introduced to unfertilized egg, fertilized egg, sperm and germinal cell including their primordial germ cell by means of calcium phosphate method, electric pulse method, lipofection method, condensation method, microinjection method, particle gun method, DEAE-dextran method or the like, and an embryo is thereby produced using the aforesaid cell.

The foreign DNA used for production of the transgenic animal may be a DNA construct which has a domain encoding the present protein under the control of various promoters capable of expressing DNA derived from various mammals (e.g., rabbit, dog, cat, guinea pig, hamster, rat, mouse) and is equipped with terminator or the like. Such DNA construct may be selected appropriately depending on types of DNA introduction method and may assume expression vector aspect known in the art as well as naked DNA.

The transgenic animal may also possess the foreign DNA in the form of hetero or homo. Further, the transgenic animal may be such in which such foreign DNA is introduced at random to host chromosome or introduced to a desired site by knock-in form. The transgenic animal tends to express the present protein in large excess as compared with ordinary case and therefore, when, for example, hyperfunction of the present protein is manifested, the transgenic animal may be used as a model animal of the pathological condition.

Further, according to the present invention, such transgenic animal is also presented which animal retains foreign DNA encoding mutant-type protein that does not have activity homogenous to the present protein, since mutant-type of the present protein, for example, serine at position 1416 is replaced by alanine and is not able to become substrate of Akt. Although the transgenic animal expressing the mutant-type protein may be hetero or homo in a similar way as the transgenic animal to which foreign DNA of the present protein is introduced, in cases where mutant-type foreign DNA is introduced at random, the mutant-type protein is expressed in many cases in addition to the present protein; and in cases where mutant-type foreign DNA is introduced so as to destroy the host chromosome encoding the present protein, it expresses only the mutant-type protein. The transgenic animal that expresses mutant-type protein may be used for elucidation of pathological mechanism of functionally-inactive type refractory symptom of the present protein and research applications of treatment methods of such disorder. Further, such animal may be utilized for screening and assessment of therapeutic medicine for functionally-inactive type refractory symptom of the present protein.

Such transgenic animal may be utilized as a cell source for tissue culture, a tissue source for tissue observation, a cell source for drug screening, a source for acquisition of the present protein or mutant-type protein thereof.

(Knockout Animal)

According to the present invention, a nonhuman animal in which expression of DNA encoding the present protein is suppressed is presented. With such animal, since expression of the present protein is suppressed, there is a possibility that various activities to which the present protein is involved are deleted; it may be used as a model for a disease attributable to inactivation of bioactivity of the present protein.

As for nonhuman mammals, those similar to the transgenic animals may be used. Further, in order to obtain a knockout animal (knockdown animal) in which DNA encoding the present protein is destroyed by knockout, a targeting vector is constructed utilizing the base sequence of genome encoding the present protein, coding region or their proximity to be used for embryo manufacturing. For embryo manufacturing, use of body cell which allows manufacturing of ES cell or nonhuman clone animal is preferable. Further, after the embryo, in which nucleic acid construct capable of expressing the RNA interference is introduced, is manufactured, it is possible to obtain knockdown animal in which expression of DNA encoding the present protein is suppressed by RNA interference.

(Analysis Method or the Like, Diagnosis Example, Diagnostic Method, Diagnostic Kit)

The antibody of the present invention is capable of specifically recognizing the present protein or phosphorylated present protein. Use of the antibody of the present invention allows quantitative determination of the present protein or phosphorylated present protein in a specimen by measurement method such as enzyme antibody method such as particularly ELISA using antibody such as EIA. In other words, the antibody of the present invention may be used as reagent for quantitative determination of the present protein or phosphorylated present protein. It may also be used as qualitative reagent of the present protein as a matter of course. Further, since amount of the present protein or phosphorylated present protein in the specimen such as cell and tissue is associated with diagnosis of disorders to which the present protein is involved, e.g., disorders related to cell motility, cell movement and angiogenesis, the antibody of the present invention may be used as a diagnostic agent for these disorders.

Further, by utilizing a fact that Akt phosphorylates the present protein, concentration of a compound, which activates and inhibits various activities of the present protein, can be detected qualitatively from degree of activation or degree of inhibition of the phosphorylation. In other words, an assay system which contains Akt and the present protein and which can phosphorylate the present protein by Akt is prepared in advance, the test compound is supplied to the assay system, the present protein that is substrate or phosphorylated present protein that is reaction product is then detected to know qualitatively whether the test compound is a compound activating phosphorylation of the present protein by Akt or a compound inhibiting the same. Meanwhile, detection of the present protein or phosphorylated present protein can be made by the enzyme antibody method using an antibody specific to the present protein or an antibody specific to phosphorylated present protein. Further, in a case with a standard curve or the like is drawn utilizing a similar system and in which the test compound is a compound activating or inhibiting phosphorylation of the present protein by Akt, the test compound can be determined quantitatively. Qualitative analysis or quantitative analysis of a test compound by such assay system may be utilized for screening method of the present invention and diagnostic method for disorders to which the present protein is involved.

Quantitative analysis of the protein of the present invention and phosphorylated antibody using the antibody of the present invention is not particularly limited, and any of measurement method may be used as long as amount of the antibody, antigen or antibody-antigen compound material corresponding to antigen level (e.g., amount of protein) in the liquid to be measured is detected by chemical or physical means, and is calculated from the standard curve drawn using a reference solution containing a known amount of antigen. For example, nephrometry, competition method, immunometric method and sandwich method are used preferably, while use of the sandwich method is particularly preferably from sensitivity and specificity viewpoints. As for labeling agent used in the measurement method using labeling substance, for example, radioisotope, enzyme, fluorescent substance, luminescent material or the like are used. For radioisotope, for example, [125I], [131I] are used; for the enzyme, those which are stable and have greater specific activity are preferable and, for example, β-galactosidase, β-glucosidase, alkali phosphatase, peroxidase, malic acid dehydrogenase or the like are used; for fluorescent substance, for example, fluorescamine, fluorescein isothiocyanate or the like are used; as for luminescent material, for example, luminol, luminol derivative, luciferin, lucigenin or the like are used. Further, biotin-avidin system may be used for binding of antibody or antigen and the labeling agent. As for carrier, for example, insoluble polysaccharide such as agarose, dextran, cellulose, synthetic resin such as polystyrene, polyacrylamide, silicone, or glass are used. Antibody molecule itself or a part thereof may be used for above-shown detections.

A diagnosis kit of the present invention may contain one type or two types or more selected from Akt phosphorylation assay system elements including the antibody of the present invention and Akt and the present protein such as Girdin. The antibody of the present invention, Akt phosphorylation assay system explained above may be used for research applications of cell motility, cell movement and angiogenesis as well as diagnosis application.

The present teachings will be described with reference to exemplar embodiments. It should be noted that the present teachings are not limited to the below embodiments. The experimental methods and the like employed in the embodiments will be explained, which will be followed by individual examples thereby carried out.

1. Yeast Two-Hybrid Assays

To identify proteins interacting with Akt, a full-length cDNA encoding human Akt1 was inserted into the pAS2 vector (Clontech). The resulting construct was used as bait to screen a human fetal brain MATCHMAKER cDNA library as previously described (Murakami et al., 2002). Two positive plasmids containing cDNA inserts were selected and sequenced. They contained the cDNA fragments encoding the C-terminal region of Girdin (residues 1217-1870). A full-length cDNA encoding Girdin was isolated from the human fetal brain poly A+ RNA by 5' rapid amplification of cDNA ends (5'-RACE system, Invitrogen). Additionally, yeast two-hybrid binding assays were performed using purified pAS and pACT constructs containing the fragments of human Akt1 and Girdin cDNAs.

2. Plasmids

Wild type, constitutively active and dominant negative human Akt1 constructs were generously provided by Y. Gotoh (University of Tokyo). The constructs of pcDNA3.1-, pGEX-, and pEGFP-Girdin fragments were produced as described elsewhere (Murakami et al., 2002). EGFP was fused to the amino termini, and V5 and myc tags were fused to the carboxyl termini of the proteins. Girdin mutants were generated using the QuikChange™ site-directed mutagenesis kit (Stratagene) according to the manufacturer's protocol. The siRNA-resistant Girdin was created by introducing two silent mutations into Girdin at nucleotides 780-800 (5'-AA-GAAGGCTACGGCAGGAATT-3') (underline indicates mutations).

3. Antibodies

Rabbit anti-Girdin polyclonal antibody was developed against the 19 carboxyl-terminal amino acids of Girdin and affinity-purified with the immunized peptide. The antiphospho Girdin polyclonal antibody was supplied by Kumamoto Immunochemical Laboratory, Transgenic Inc. (Kumamoto, Japan). It was raised by immunizing rabbits with a keyhole limpet hemocyanin-conjugated phosphopeptide corresponding to Girdin amino-acid sequence 1408-1420 (CDINRER-QKpSLTLT). Antiserum was purified as a bound fraction of the phosphopeptide-conjugated column. Other antibodies used in this study include anti-Akt polyclonal antibody (Cell Signaling Technology), anti-phospho Akt polyclonal antibody (Cell Signaling Technology), and anti-Cortactin monoclonal antibody (Upstate).

4. Kinase Assays

Immunoprecipitates with anti-V5 antibody (Invitrogen) from COS7 cells expressing Girdin CT-V5 WT or SA or purified GST-CT were incubated with recombinant active or inactive Akt (500 ng) (Upstate) with 10 µCi of [γ-32P]ATP (3000 Ci/mmol, Amersham) in kinase buffer (20 mM MOPS, 25 mM β-glycerophosphate, 5 mM EGTA, 15 mM MgCl2, 1 mM dithiothreitol and 1 mM NaVO3). Mixtures were incubated at 30° C. for 30 min and reactions were terminated by addition of Laemmli sodium dodecyl sulfate (SDS) sample dilution buffer (20 mM Tris-HCl, pH 6.8, 2 mM EDTA, 2% SDS, 10% sucrose, 20 µg/ml bromophenol blue, 80 mM dithiothreitol).

5. Immunofluorescent Staining

Vero cells were plated on fibronectin (10 µg/ml, Sigma) and collagen I (10 µg/ml, Upstate)-coated cover slips or glass base dishes, fixed, and stained with the indicated antibodies. Fluorescence was examined using a confocal laser-scanning microscope (Fluoview FV500, Olympus).

6. Actin Cosedimentation Assays

F-actin cosedimentation assays were performed according to the manufacturer's protocol (Cytoskeleton). Briefly, purified GST fusion proteins, GST alone, and α-actin (Cytoskeleton) were incubated for 30 min at room temperature with 40 µg of pure actin filaments. The final concentration of F-actin was 18 µM. Filaments were subsequently pelleted by centrifugation (100,000×g) (Beckman). The cosedimented proteins were resolved by SDS-PAGE and detected by either Coomassie Brilliant Blue (CBB) staining or Western blot analyses using anti-GST antibody (Cell Signaling Technology) or anti-phospho Girdin Ab. For quantitative analyses, a fixed concentration of GST-Girdin CT2 (1 µM) was mixed with increasing amounts of F-actin (0-2.5 µM) in polymerization buffer and incubated at room temperature for 30 min. Proteins were centrifuged as described above, and total pellets and supernatants were loaded separately on SDS-PAGE. Protein bands were detected by CBB staining, and scanned and quantified using the software program WinROOF (Mitani Corp., Fukui, Japan).

7. RNA Interference

The siRNA-mediated knockdown of Girdin and Akt was performed using previously described methods (Watanabe et al., 2004). The targeted sequences that effectively mediated the silencing of the expression of Girdin are as follows (only sense sequences are shown): 5'-AACCAGGTCATGCTC-CAAATT-3' (nucleotides 145-165, Girdin siRNA (A)) and 5'-AAGAAGGCTTAGGCAGGAATT-3' (nucleotides 780-800, Girdin siRNA (B)). The 21-nucleotide synthetic duplexes were prepared by Qiagen. The siRNA specific to human Akt1 was purchased from Qiagen. Vero cells were transfected with the siRNAs or a 21-nucleotide irrelevant RNA (Qiagen) as a control, using lipofectamine 2000 (Invitrogen) according to the manufacturer's protocol.

8. Freeze-Replica Electron Microscopy of the Cytoplasmic Cell Surface

Electron microscopy for the cytoplasmic surface of the cell membrane was carried out according to previously described methods (Heuser, 1989, 2000; Usukura, 1993). Vero cells cultured on glass coverslips (3 mm in diameter, standard #1Matsunami, Osaka Japan) were transfected with siRNAs. Immediately after being unroofed from the apical cell membrane, the cells were fixed for 30 min in 2.5% glutaraldehyde in buffer A (70 mM KCl, 5 mM MgCl2, 3 mM EGTA, 30 mM HEPES buffer adjusted at pH 7.4 with KOH). After being washed with buffer A/distilled water, specimens were quickly frozen with liquid helium using the rapid-freezing device (Eiko, Tokyo Japan). Samples were then freeze-etched and rotary shadowed with platinum-carbon, in a newly developed freeze etching device (FR9000, HITACHI, Ibaraki, Japan). For immuno-labeling of Girdin molecules, the unroofed cells were fixed for 30 min in 4% paraformaldehyde/0.5% glutaraldehyde in buffer A. After being washed three times with buffer B (100 mM NaCl, 30 mM Hepes, 2 mM CaCl2), the samples were quenched and blocked, and then labelled for 1 hr at 37° C. with primary and secondary 10 nm-gold conjugated antibodies (Amersham) in buffer B containing 1% BSA. Finally, specimens were rapidly frozen and freeze-etched as described above.

9. Scratch-Induced Cell Migration and Time-Lapse Imaging

Directional cell migration of Vero cells was stimulated in a monolayer using an in vitro scratch-wound assay (Watanabe et al., 2004). Vero cells were seeded on fibronectin-precoated coverslips or 35 mm glass base dishes, and transfected with indicated siRNAs. Forty-eight hrs after the transfection, the confluent Vero cells were scratched with a 200-μl disposable plastic pipette tip and were allowed to migrate toward the wound. The cells were fixed at the indicated times for immunofluorescent staining. For time-lapse observation, cells were cotransfected with siRNAs and GFP-actin, and subjected to the scratch-wound assays. The cells at the wound edges were observed with a confocal laser scanning microscope (Fluoview FV500, Olympus).

10. Three-Dimensional Cell Migration Assays

To assess the motility of cells transfected with various constructs or siRNAs, the modified Boyden chamber migration assay, which enabled the counting GFP-labeled cells migrating across a fluorescence-blocking planer micropore membrane by using HTS FluoroBlok Insert (8.0 μm pores, 24-well format, BECTONE DICKINSON), was performed. Both sides of the membrane were coated with 10 μg/ml of fibronectin for 12 hrs at 37° C. and washed with phosphate-buffered saline (PBS). The chambers were then placed in 24-well dishes filled with Dulbecco's modified medium (DMEM) containing 0.1% BSA with or without 20 ng/ml of human recombinant EGF. For migration assays of HT-1080 cells, DMEM with 10% fetal bovine serum (FBS) was added to the lower chamber. Cells (1×105) were transfected with GFP (0.5 μg, to identify transfected cells), indicated constructs (2.5 μg), and siRNAs (20 pmol) in 24-well plates, plated in the upper compartment and allowed to migrate through the pores of the membrane for 4 hrs. Cell motility was quantified by using a fluorescence microscope to count the GFP-positive cells that had migrated through the membrane.

11. Protein-Lipid Overlay Assays

GST fusion proteins were expressed in DH5□ or BL21-CodonPlus (Stratagene) cells and purified using conventional methods. Binding of the purified GST-CT to phospholipids was examined at 4° C. using a PIP-Strip (Echelon Bioscience) according to the manufacturer's protocol. Bound GST-CT proteins were detected with either anti-Girdin or anti-phospho Girdin antibodies.

Example 1

Identification of an Akt-Interacting Protein, Girdin/APE, Primary Structure Thereof and Expression Manner To identify novel Akt substrates, a yeast two-hybrid screen using full-length human Akt1 as bait was performed, and interacting proteins using a human fetal brain cDNA library were searched for. Two independent and overlapping clones (F-10 and F-12) encoding a novel gene product were identified. When expressed in yeast, the protein encoded by the F-10 and F-12 cDNAs was shown to interact only with the carboxyl-terminal regulatory domain (RD) of Akt1. Use of 5'-rapid amplification of cDNA ends (5'-RACE) provided a clone comprising the entire coding region with an additional 3.8-kb cDNA of contiguous 5' sequence. The full-length cDNA included an open reading frame of 5610-bp (base pair) (GenBank™/EMBL/DDBJ accession number AB201172) and was predicted to encode a novel protein of 1870 amino acids, which was designated Girdin, with a calculated molecular mass of 220 kilodaltons (kDa) (Supplemental FIG. S1). Database searches revealed homologues in mouse, rat, and Drosophila (not shown).

Figure 1C:
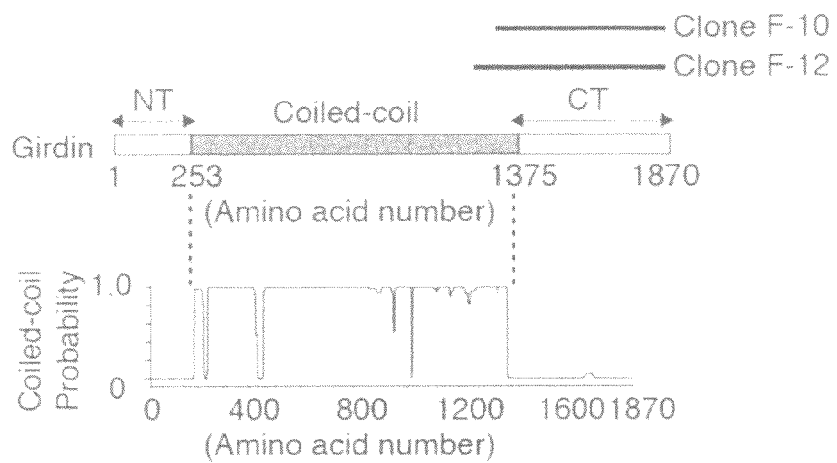
FIG. 1c shows a schematic presentation of Girdin and its structure predictions provided by the COILS algorithm.

The structure of Girdin predicted by the COILS algorithm (Lupas et al., 1991) was showed in FIG. 1c. As described in FIG. 1c, Girdin showed a tendency to form a dimmer with an α-helical coiled-coil conformation in its middle domain, between Ala-253 and Lys-1375 and N-terminus domain (NT). The predicted coiled-coil domain contains 135 continuous heptad repeats (abcdefg) 135 that are typical of α-helical coiled-coils (FIG. 1h).

Figure 1D:
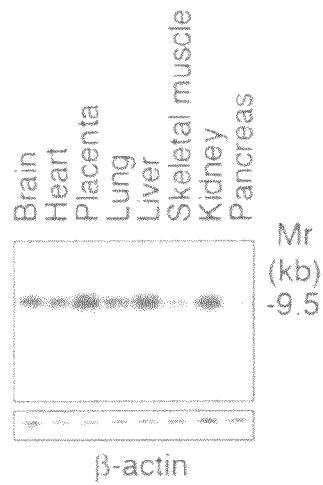
FIG. 1d shows an ubiquitous expression of Girdin mRNA in human adult tissues. A human Multiple-Tissue Northern (MTN™) blot (Clontech) was hybridized with a probe corresponding to the 3' region of Girdin cDNA.
Figure 1E:
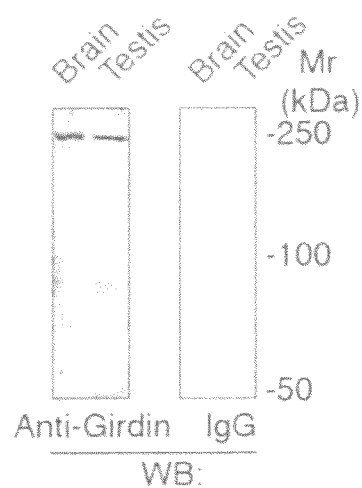
FIG. 1e shows an endogenous Girdin in lysates from human brain and testis, which was detected with anti-Girdin polyclonal antibody but not with rabbit IgG under reducing conditions.

Expression of Girdin mRNA was analyzed by Western blotting. The 9.5 kb Girdin transcript was found to be expressed ubiquitously in various human tissues by high stringency Northern blot analysis (FIG. 1d). To facilitate further studies on Girdin, a polyclonal antibody (Ab) raised against its 19 C-terminal amino acids was generated. Western blotting analysis revealed that the anti-Girdin Ab recognizes a specific band of relative molecular mass of 250 kDa in human brain and testis lysates (FIG. 1e).

Figure 1F:
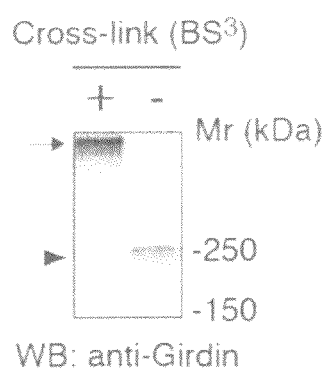
FIG. 1f shows a detection of a large complex formation formed by endogenous Girdin. COS7 postnuclear supernatants were subjected to Western blot analysis using anti-Girdin antibody, either directly (−) or after crosslinking with 100 μM BS3 (+). The size of a band detected after cross-linking (arrow) is extremely large as compared with that without cross-linking (arrowhead).
Figure 1G:
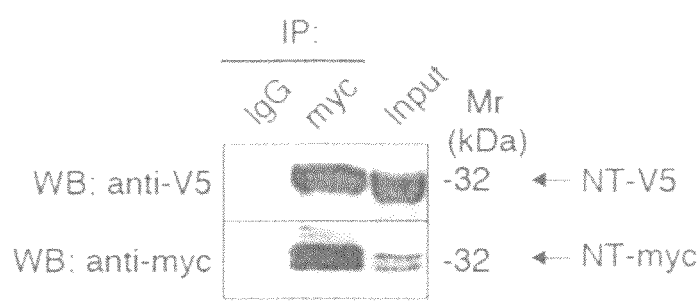
FIG. 1g shows the NT domain of Girdin forms an oligomer. NT-V5 and NT-myc were transfected into COS7 cells and immunoprecipitated with anti-myc antibody, whereby NT-V5 was coimmunoprecipitated with NT-myc. The multiple bands in the lower panel may represent the degradation of NT-myc in cells.
Figure 1I:
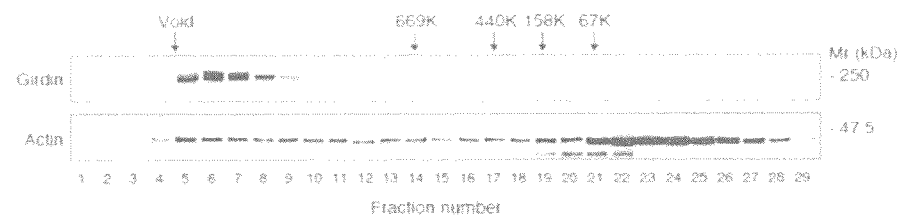
FIG. 1i shows that Girdin forms oligomers in cells and forms a large protein complex with the actin filaments. (A) shows the whole cell lysates from COS7 cells were loaded onto Superpose 6 PC 3.2/30 (Amersham) for gel filtration; then following fractionation, each fraction was examined by Western blot analyses with anti-Girdin (upper panel) and anti-actin (lower panel) antibodies to determine their respective elution profile. Actin was eluted as two peaks, the first one of which excluded in the void volume, which is related to a polymeric form of actin (F-actin). The elution of the majority of actin was at positions corresponding to low molecular mass (<67 kDa), which suggests a partially depolymerized or monomeric form (G-actin). These data suggest that Girdin forms a large complex with F-actin of various lengths. (B) shows that COS7 cells were transfected with either GFP-Girdin N-terminal fragment (NT) tagged with V5 epitope (GFP-NT-V5) (cf. upper panel) or NT tagged with myc epitope (NT-myc) (cf. lower panel), and the cell lysates were loaded onto Superose 6 PC for gel filtration; then following fractionation, each fraction was examined by Western blot analyses with anti-V5 and anti-myc antibodies. Because the calculated molecular mass of the GFP-NT-V5 or NT-myc monomer is 58 or 28 kDa, respectively, the data suggest that the NT domain forms dimers. Method: COS7 cells in dishes were washed with cold PBS and suspended in 0.5 mL of 25 mM Tris-HCl, pH 8.0, 250 mM NaCl, 5 mM EDTA, 1 mM DTT. The suspension was sonicated and centrifuged at 100,000 g for 60 min at 4° C. The supernatants were applied to a Superose 6 PC 3.2/30 column (Amersham). The elution was performed at a flow rate of 40 μl/min. Fractions of 50 μl were collected. The protein markers used were thyroglobulin (669K), Ferritin (440K), Aldolase (158K), and bovine serum albumin (67K).
Figure 1I:
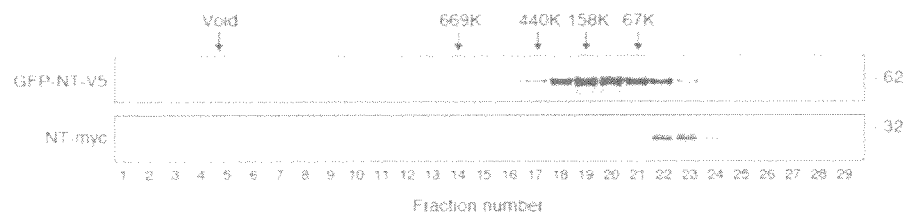

Because of the existence of an α-helical coiled-coil domain in the primary structure of Girdin, the possibility of Girdin being an oligomeric molecule was investigated. Cell lysates from COS7 cells were analyzed by Western blot analysis with anti-Girdin Ab. The results were shown in FIG. 1f. After cross-linking, Girdin was predominantly found in a complex of large molecular mass in intact cells. Further, the lysates from COS7 cells were subjected to gel filtration and the data confirmed that Girdin forms a large protein complex. Then, a test on whether the NT and CT domains contribute to the oligomerization of Girdin was performed. When V5 epitope-tagged NT (NT-V5) and myc epitopetagged NT (NT-myc) were expressed in COS7 cells, a complex of these two NT domains was observed (FIG. 1g). This result implies that the NT domain facilitates the oligomerization of Girdin. In contrast, the CT domain did not form an oligomer in cells (data not shown). Analysis of the lysates from COS7 cells expressing the NT domain by gel filtration suggested that the NT domain forms a dimer (FIG. 1i).

Example 2

Akt Phosphorylates Girdin In Vitro and In Vivo

In vitro and in vivo assays were initially used to ascertain if Girdin and Akt physically interact with each other. Neither in vitro binding nor immunoprecipitation assays using various fragments of Girdin and Akt demonstrated the formation of a stable complex of the two proteins (data not shown), suggesting that they may normally associate in a very transient manner, as observed for the interactions between protein kinases and their substrates. It has been established that Akt preferentially phosphorylates substrates that contain the sequence R-x-R-x-x-S/T. The amino acid sequence adjacent to a serine at position 1416 (Ser-1416, RERQKS) in the CT domain of Girdin had conformed to this consensus sequence. This was the only consensus site in the protein. Since the CT domain with the putative phosphorylation site was conserved in different mammalian Girdin homologues, consideration had been given to whether Akt phosphorylates Girdin.

Figure 2A:
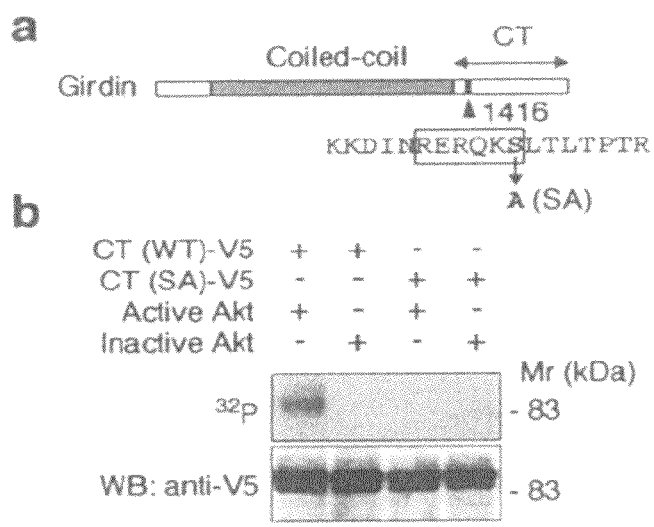
In FIG. 2a, (a) shows a potential Akt phosphorylation site at serine 1416 of the Girdin CT domain. (b) shows respective Girdin CT-V5 WT and SA mutants (in which serine 1416 was replaced with alanine) were transfected into COS7 cells and immunoprecipitated with anti-V5 antibody, followed by incubation with recombinant active and inactive Akt respectively in the presence of radiolabeled ATP. Phosphorylated Girdin CT was detected by autoradiography (cf. upper panel). Immunoprecipitated Girdin CTs were detected by Western blot analysis (cf. lower panel).
Figure 2B:
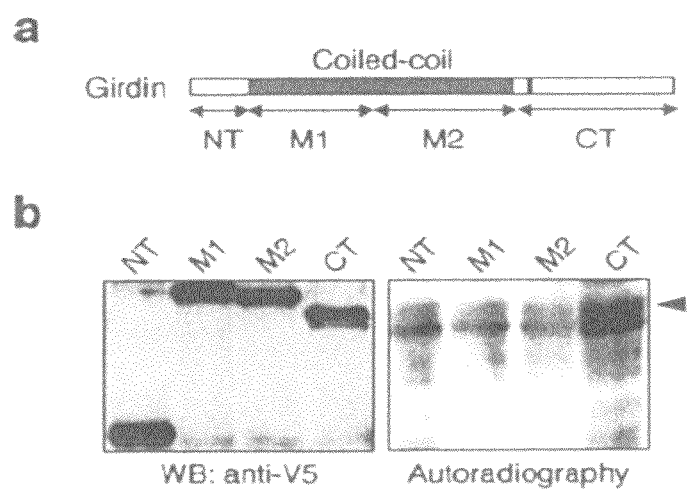
In FIG. 2b, (a) shows various fragments of Girdin tagged with V5 transfected in COS7 cells. (b) shows COS 7 cells transfected with the various fragments and immunoprecipitated with anti-V5 antibody, followed by incubation with recombinant active Akt in the presence of radiolabeled ATP. Immunoprecipitated fragments were detected by Western blot analysis (cf. left panel). Phosphorylated Girdin CT was detected by autoradiography (cf. right panel).

An in vitro kinase assay described in FIG. 2a revealed that Girdin CT wild type (WT), but not its Ser-1416 substituted with Ala mutant (SA), was phosphorylated by active Akt; this fact indicating that Akt directly phosphorylates the Ser-1416 in vitro. In contrast, neither the NT nor the coiled-coil domain of Girdin was phosphorylated by Akt in vitro (FIG. 2b).

Figure 2C:
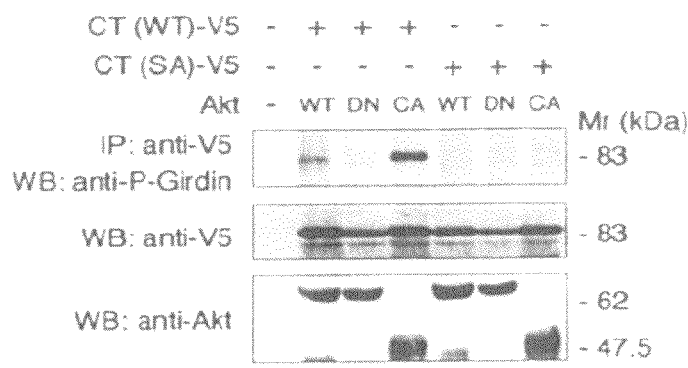
FIG. 2c shows COS7 cells were cotransfected with Girdin CT-V5 (WT and SA respectively) and Akt mutants. Immunoprecipitates with anti-V5 antibody were subjected to Western blot analysis with anti-phospho Girdin (anti-P-Girdin) antibody (cf. upper panel). Expression of Girdin CTs and Akt mutants was monitored by Western blot analyses (cf. middle and lower panels).

In order to confirm that Ser-1416 is the site of Akt-catalyzed phosphorylation in vivo, an antibody that specifically binds to a peptide that includes phosphorylated Ser-1416 was prepared, and used for Western blotting (FIG. 2c). As shown in FIG. 2c, the anti-phospho Ser-1416 peptide antibody (anti-P-Girdin Ab) recognized the Girdin CT (WT) that was coexpressed with wild-type (Akt WT) or constitutively active Akt (Akt CA), but not with dominant negative Akt (Akt DN). The anti-P-Girdin Ab did not recognize the Girdin CT (SA) mutant coexpressed with the Akt CA. These findings indicate that the anti-P-Girdin Ab specifically recognizes the Girdin CT phosphorylated at Ser-1416.

Figure 2D:
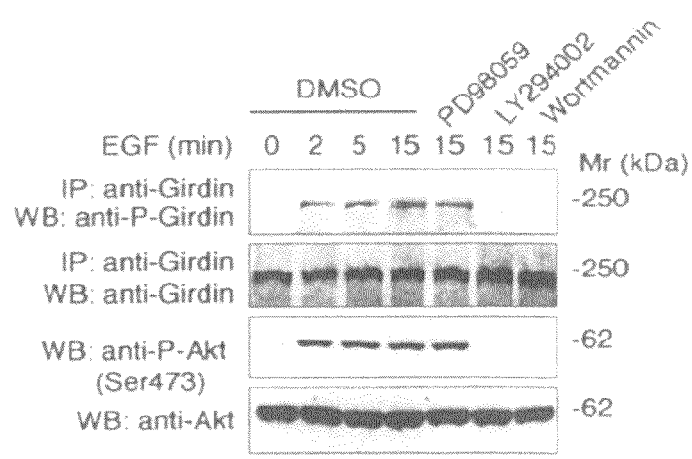
FIG. 2d shows COS7 cells were stimulated with EGF (50 ng/ml) for 15 min in the presence of DMSO (0.1%), PD98059 (50 μM), LY294002 (10 μM), and Wortmannin (30 nM). Immunoprecipitates with anti-Girdin antibody were subjected to Western blot analyses with anti-P-Girdin and anti-Girdin antibodies. Activation of Akt was monitored by Western blot analyses with anti-phospho Akt antibody.
Figure 2E:
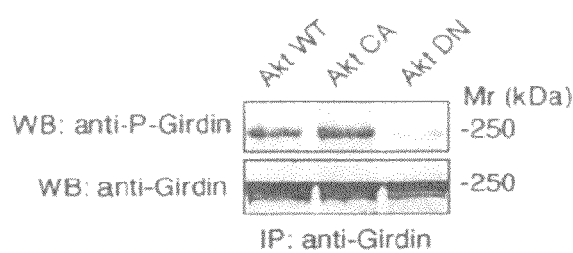
FIG. 2e shows induction of phosphorylation in COS7 cells transfected with Akt WT, Akt CT and Akt DN. COS7 cells were transfected with Akt mutants. Endogenous Girdin was immunoprecipitated with anti-Girdin antibody, followed by Western blot analyses with anti-P-Girdin (cf. upper panel) and anti-Girdin (cf. lower panel) antibodies.
Figure 2F:
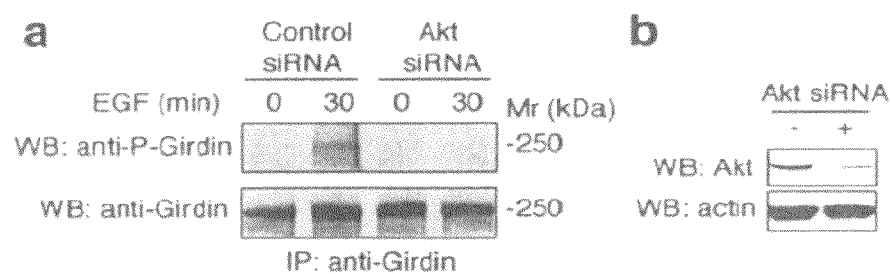
In FIG. 2f, (a) shows effects of Akt knockdown on phosphorylation of endogenous Girdin. COS7 cells were transfected with either control or Akt siRNAs, and incubated for 48 hrs. Cells were then stimulated with EGF for 30 min and the phosphorylation of Girdin was analyzed as described in FIG. 2e. (b) shows depletion of Akt in COS7 cells by siRNA.

Next, whether the anti-P-Girdin Ab can detect the endogenous Girdin phosphorylated in response to external stimuli that physiologically activate endogenous Akt was given consideration to. As shown in FIG. 2d, the addition of epidermal growth factor (EGF) induced the phosphorylation of a protein that corresponds to immunoprecipitated Girdin (250 kDa) with a time course similar to that of Akt activation. Furthermore, the phosphorylation of Girdin was inhibited when cells were treated with the PI3K inhibitors LY294002 and Wortmannin, but not with the mitogen-activated protein kinase kinase 1 (MEK1) inhibitor PD98059. It has therefore been concluded that the phosphorylation of Girdin is induced by EGF in a PI3K-dependent manner. As shown in FIG. 2e, the expression of Akt WT and Akt CA, but not Akt DN, had induced significant phosphorylation of Girdin, indicates that active Akt alone is sufficient to induce its phosphorylation in cells. Moreover, Girdin phosphorylation was undetectable in the cells transfected with Akt small interfering RNA (Akt siRNA). These findings confirmed that Akt activation is necessary for Girdin phosphorylation.

Example 3

Girdin Associates with Actin Filaments Via its C-Terminal Domain

To determine the subcellular localization of Girdin, Vero fibroblasts were immunofluorescently stained with the anti-Girdin Ab. As shown in (a) of FIG. 3a, the results showed that Girdin was colocalized with the actin stress fibers in quiescent cells. When the cells were stimulated with EGF (50 ng/ml), they started to polarize, followed by directional extension of lamellipodia. In the EGF-stimulated cells, Girdin localized not only on the actin stress fibers but also on the lamellipodia at the leading edge, which was illustrated upon staining for the Arp2/3-binding protein Cortactin in (b) of FIG. 3a.

Figure 3A:
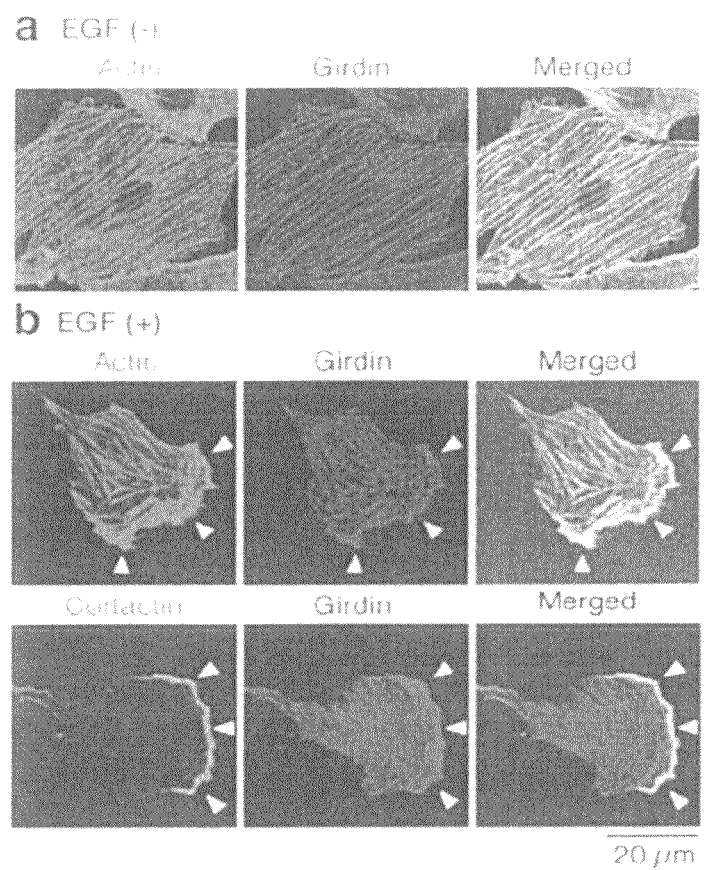
FIG. 3a shows quiescent and EGF-stimulated vero cells were doubly stained with either Alexa488-phalloidin (cf. upper panel) or anti-Cortactin antibody (cf. lower panel) and anti-Girdin antibody Quiescent in (a) and (b), respectively. Arrowheads denote lamellipodia at the leading edge.
Figure 3B:
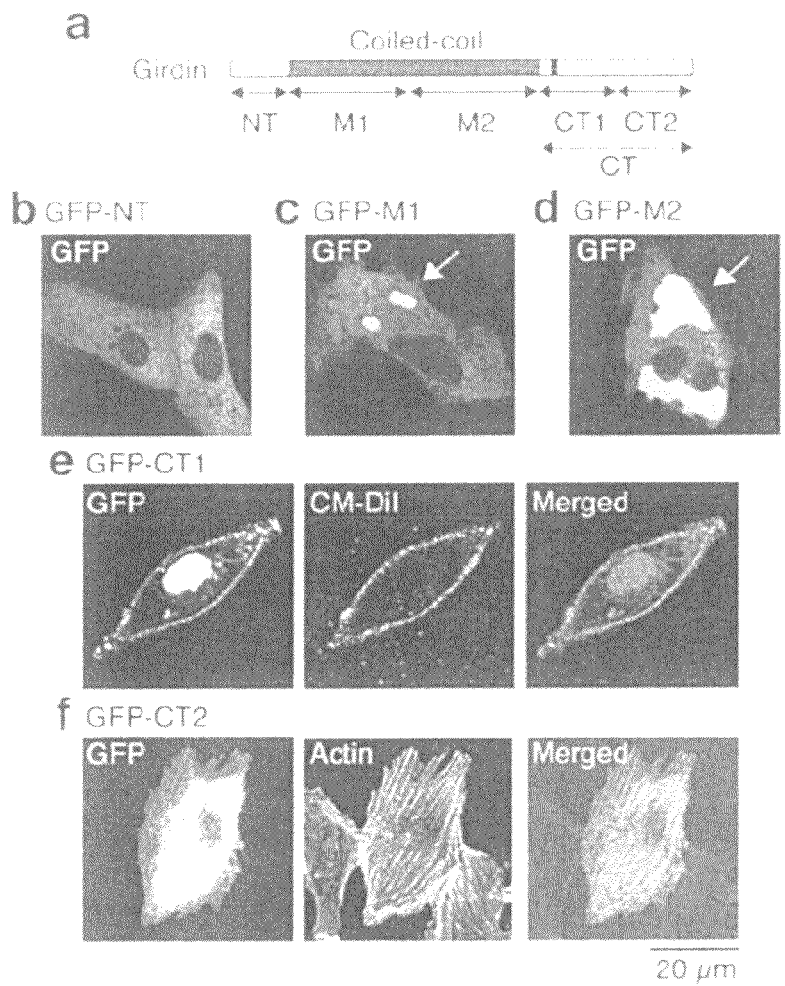
FIG. 3b shows subcellular localization of Girdin fragments. Various fragments of Girdin fused with GFP were expressed in Vero cells, fixed, and stained with the indicated probes. Arrows denote aggregates of the expressed proteins.

The localization of Girdin raises the possibility that Girdin is an F-actin (filamentous actin)-binding protein. To identify the actin-binding domain of Girdin, green fluorescence protein (GFP)-fused truncated versions encoding the NT (GFP-NT), N-terminal half (GFP-M1) and C-terminal half (GFP-M2) of the coiled-coil domain, and the N-terminal half (GFP-CT1) and the C-terminal half (GFP-CT2) of the CT domain were generated, and examined their intracellular localization (FIG. 3b (a)). As shown in FIG. 3b (b) through (d), when expressed in Vero cells, the GFP-NT, GFP-M1 and GFP-M2 localized in the cytoplasm. As shown in FIG. 3b (e), the GFP-CT1 localized in both the nucleus and the plasma membrane as shown by its colocalization with CM-DiI, a carbocyanine membrane probe, while GFP-CT2 apparently localized on the stress fibers as shown in FIG. 3b (f). These findings suggest that Girdin localizes on the actin filament via its CT2 domain, whereas it also associates with the plasma membrane via its CT1 domain. The nuclear localization of the GFPCT1 seen here may be an artifact, because no accumulation of endogenous Girdin was visible in the nucleus (FIG. 3a).

Figure 3C:
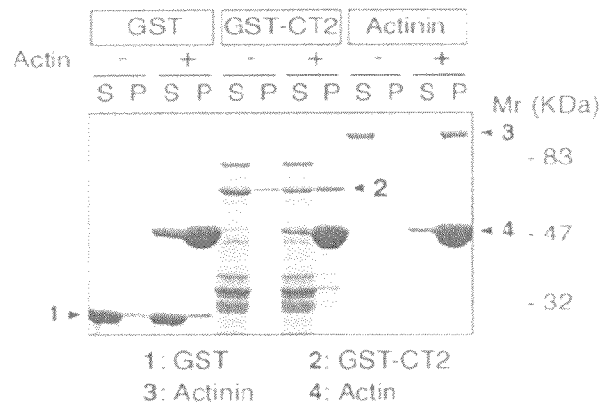
FIG. 3c shows Girdin CT2 fragment directly interacts with filamentous actin in vitro. Purified GST, GST-CT2, and α-actinin were incubated with (cf. +) or without (cf. −) in vitro prepared actin filaments. F-actin was subsequently pelletted by ultracentrifugation. Cosedimentation of the various proteins with F-actin was analyzed by CBB staining of the gel.
Figure 3D:
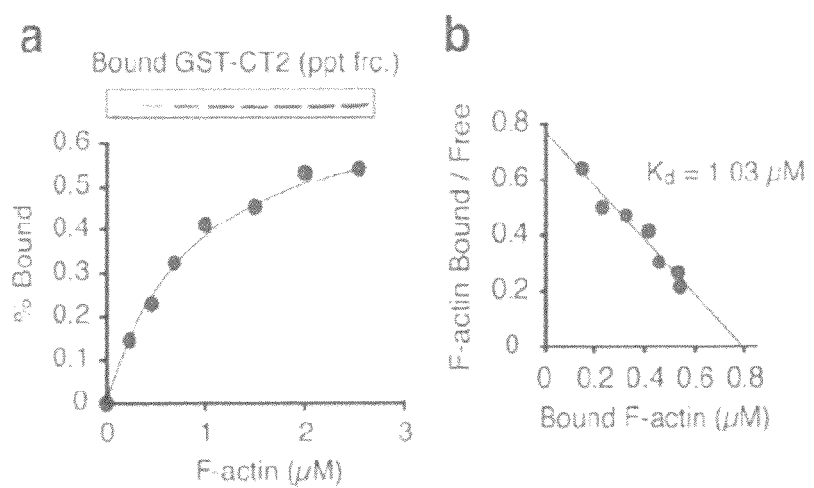
FIG. 3d shows binding manner of GST-CT2 to F-actin. A fixed amount of GST-CT2 was mixed with various amounts of F-actin, followed by ultracentrifugation. Amounts of the free and bound GST-CT2 were quantified, and the percentage of bound GST-CT2 was plotted against the concentration of F-actin, and the Kd value was calculated by Scatchard analysis.
Figure 3E:
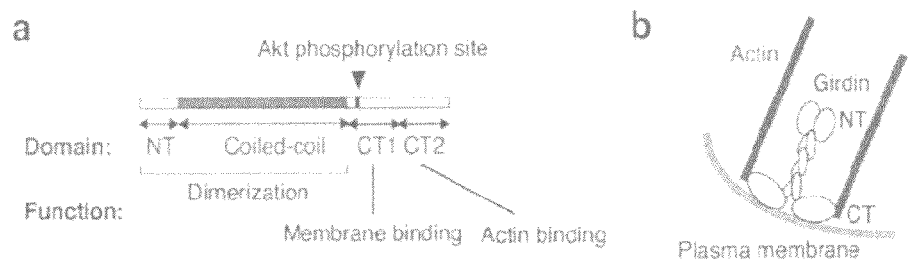
In FIG. 3e, (a) shows summary of the localization and functions of Girdin domains, and (b) shows the proposed structure of Girdin.

In addition, the actin-binding properties of the CT2 domain by actin cosedimentation assays were investigated. As shown in FIGS. 3c and 3d, the purified glutathione S-transferase (GST)-fused CT2 (GST-CT2) cosedimented with purified F-actin, as did β-actinin, whereas GST alone did not, indicating that the GST-CT2 directly binds to F-actin. As the amount of F-actin increased, as shown in FIG. 3d (a), the binding of GST-CT2 with F-actin was saturated. The estimated dissociation constant (Kd) for F-actin was 1.03 µM, indicating Girdin has relatively low affinity for F-actin (FIG. 3d (b)). The domains of Girdin, their predicted functions, and the speculated structure of Girdin are summarized and illustrated in FIG. 3e.

Example 4

Girdin is Required for the Formation of Actin Stress Fibers and Cell Migration

Figure 4A:
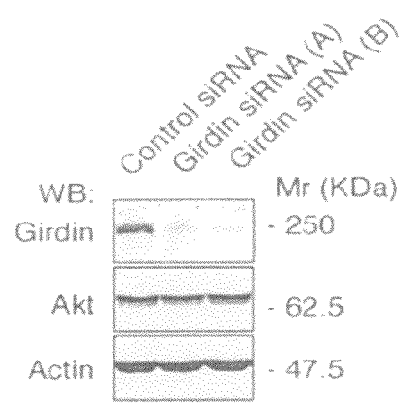
FIG. 4a shows depletion of Girdin in Vero cells by siRNA. Total cell extracts from control siRNA-transfected and Girdin siRNA-transfected Vero cells were detected with anti-Girdin, anti-Akt, and anti-actin antibodies.

To assess the function of Girdin, RNA-mediated interference (RNAi) to suppress (knockdown) the expression of Girdin in Vero cells was employed. Several Girdin small (21-nucleotide) interfering RNAs (Girdin siRNA) and a 21-nucleotide irrelevant RNA (control siRNA) were introduced into Vero cells. Western blotting analyses showed that transfection with the Girdin siRNAs effectively reduced the expression levels of Girdin by over 90% without affecting those of Akt and actin as shown in FIG. 4a. In order to verify the specificity of the knock down experiments, the two oligonucleotides, Girdin siRNA (A) and (B), were utilized for Western blotting analyses and other functional assays described in this study.

Figure 4B:
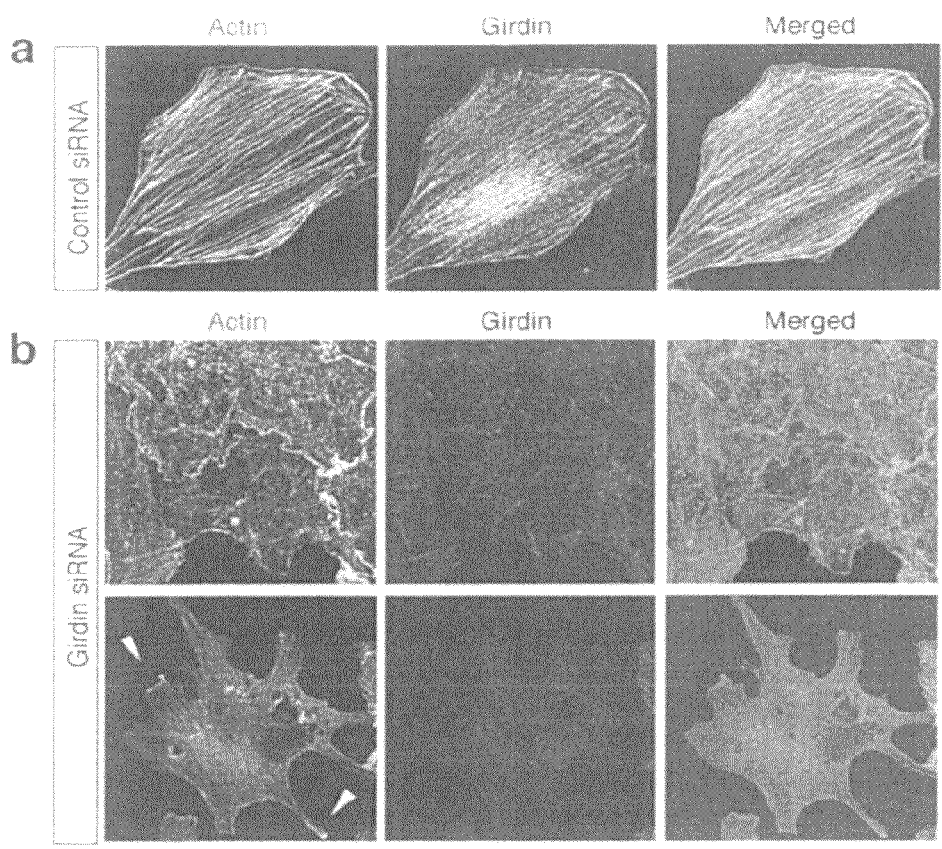
FIG. 4b shows Vero cells were transfected with control or Girdin siRNAs, and fixed 72 hrs after transfection, followed by doubly staining with Alexa488-phalloidin and anti-Girdin antibody. Arrowheads denote lamellipodia at the tips of protrusions.
Figure 4C:
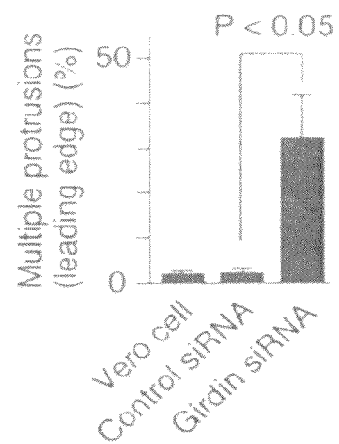
FIG. 4c shows after transfection of each siRNA, the number of cells with multiple protrusions was counted by staining with anti-Girdin antibody and Alexa488-phalloidin. More than 100 transfected cells were counted in each group. Data were expressed as average±standard error.

To test whether Girdin functions to promote the cross-linking of actin filaments, the effects of Girdin knockdown on the organization of the actin cytoskeleton were examined. Immunofluorescent staining with anti-Girdin Ab showed that the expression of Girdin was very low in the Girdin siRNA-transfected cells as shown in FIG. 4b (a). Staining of F-actin-rich structures with phalloidin revealed that the stress fibers were disrupted in the Girdin siRNA-transfected cells as shown in FIG. 4b (b), indicating that Girdin is essential for the formation of the stress fibers.

When observed under higher magnification, Girdin siRNA-transfected cells contained markedly reduced thin and short stress fibers, and lost their shape with rugged boundaries that gave rise to the formation of multiple protrusions (leading edge) (FIG. 4b (b) lower panel and 4c).

Figure 4D:
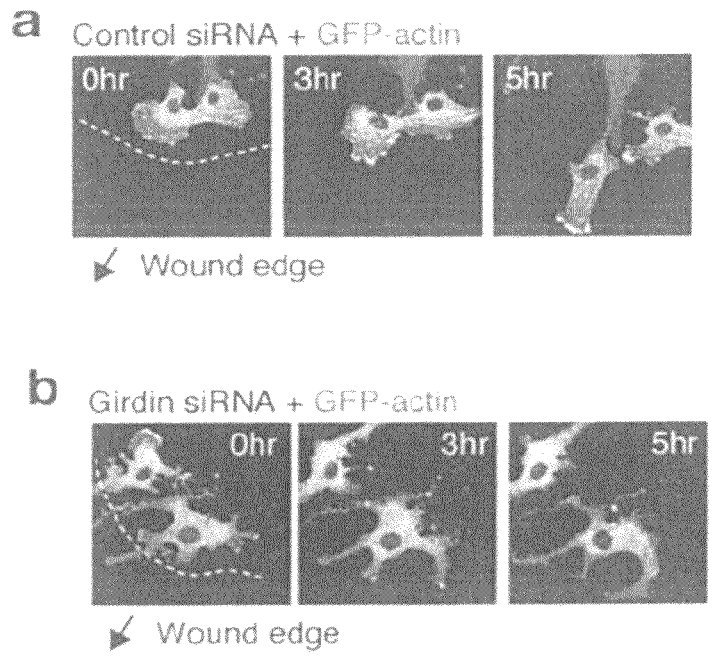
FIG. 4d shows Vero cells were cotransfected with GFP-actin and either control or various siRNA and incubated for 48 hrs. Cells were plated on fibronectin-coated glass coverslips and wounded to induce cell migration. Images were collected every 90 sec for a period of 5-6 hrs starting 2 hrs after scraping. The arrows indicate the direction of cell migration into the wounds.

To further clarify the roles of Girdin in actin dynamics, the behavior of the Girdin-depleted cells during migration in in vitro wound-healing assays was observed. As shown in FIG. 4d, it was found that the Girdin siRNA-transfected cells facing up to the wound failed to produce extended lamellipodia at the leading edge and showed migration defect with multiple protrusions that were repeatedly stretched and shortened. These results suggest that Girdin is essential for organization of actin filaments during cell migration.

To test the specificity of the effect of the Girdin knockdown, the Girdin siRNA was also introduced into another cell line, SK-N-MC neuroblastoma cells that stably express the RET receptor tyrosine kinase. Girdin siRNA-transfected SK-NMC (RET) cells exhibited disruption of the stress fibers and limited formation of lamellipodia in response to the RET ligand, glial cell-line derived neurotrophic factor (GDNF).

Example 5

Figure 5A:
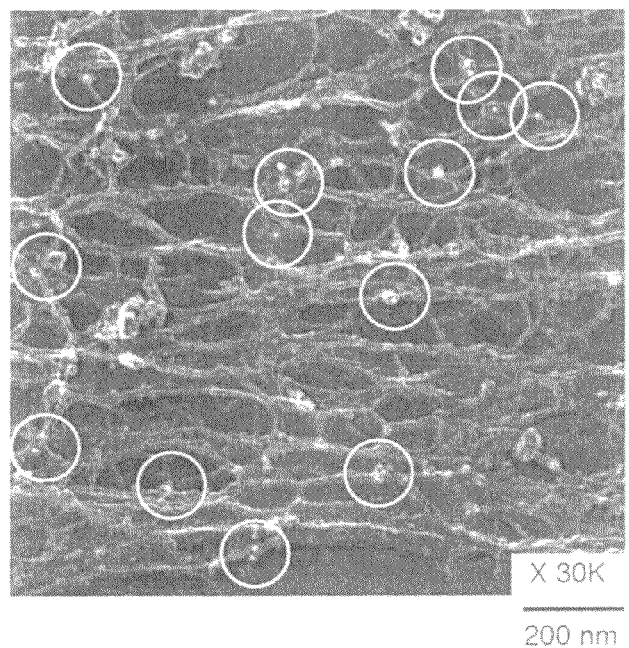
FIG. 5a shows analysis by immunogold electron microscopy with anti-Girdin antibody.
Figure 5B:
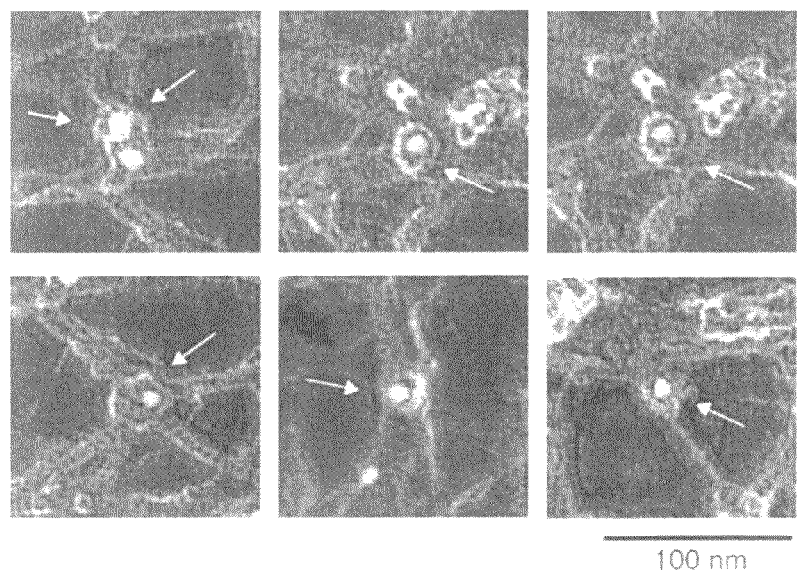
FIG. 5b shows the immunogold signals of Girdin molecules (indicated with circles) under higher magnification. Arrows denote the immunogold signals.
Figure 5C:
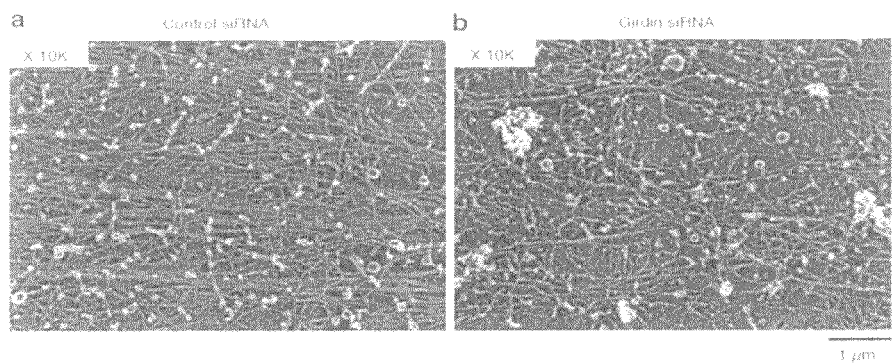
FIG. 5c shows ultrastructure of actin filaments in Vero cells transfected with either control or Girdin siRNA.

Localization of Girdin on Actin Filaments and Ultrastructure of the Girdin-Depleted Cells by Electron Microscopy To further confirm the direct interaction of Girdin with actin filaments in vivo and its roles in actin organization, ultrastructural analysis was performed by deep-etch electron microscopy of "unroofed" Vero cells. As shown in FIG. 5a, immunogold-labeling revealed that Girdin molecules localize with actin filaments. As shown in FIG. 5b, higher magnification views showed extensive colocalization of Girdin with the junctions between the actin filaments. Consistent with the immunofluorescence analysis, the density of the cortical actin filaments visible in electron micrographs of the cytoplasmic surface under the plasma membrane of Girdin-depleted Vero cells is lower than that in the control cells (FIG. 5c), where more tightly organized actin fibers predominate. In the control siRNA transfected cells, the filaments abut one another, run together without separating, and form thick cables tightly cross-linked by many molecules. Some filaments were oriented perpendicular to the other actin cables, resulting in interwoven and dense actin networks. In the Girdin siRNA-transfected cells, however, the actin bundles are sparse, and each actin filament is separated from another and is sometimes disrupted en route.

Example 6

Effects of Phosphorylation of Girdin to Localization and Interaction with Inositol Phospholipid (Phosphoinositide)

Figure 6A:
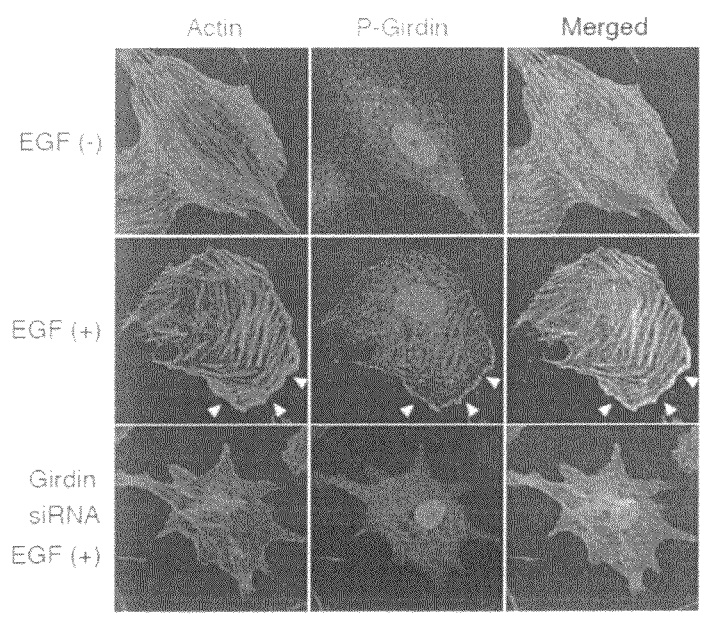
FIG. 6a shows quiescent, EGF-stimulated, and Girdin siRNA-transfected Vero cells, which were fixed and stained with Alexa488-phalloidin and anti-phospho Girdin (P-Girdin) antibody. Arrows denote the lamellipodia where the phosphorylated Girdin accumulates.
Figure 6B:
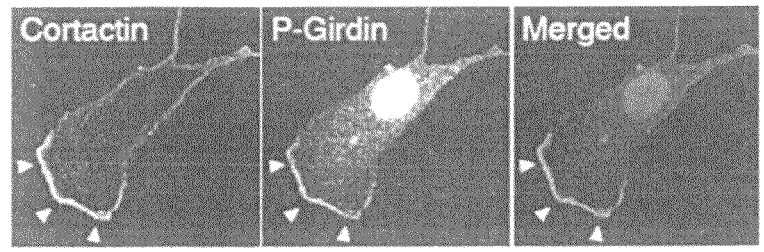
FIG. 6b shows migrating Vero cells which were doubly stained with anti-Cortactin and anti-P-Girdin antibody.
Figure 6C:
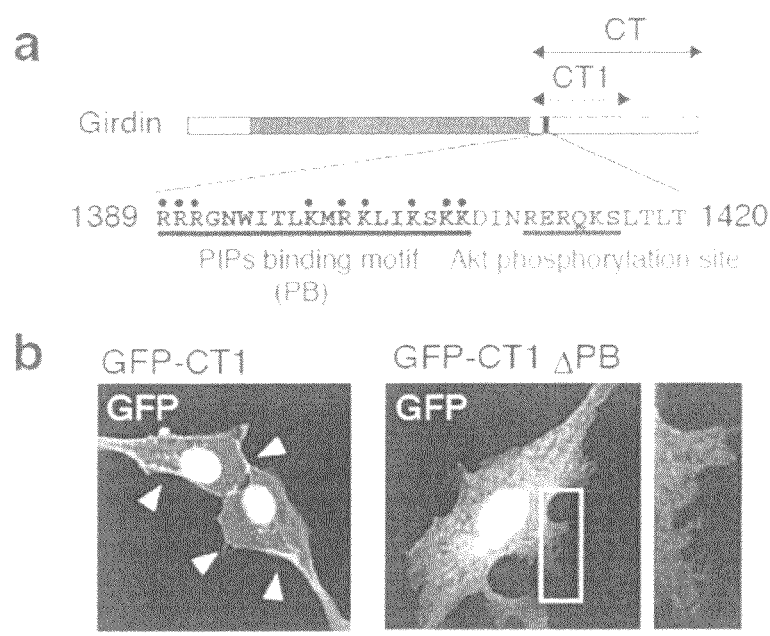
In FIG. 6c, (a) shows the putative phosphoinositide binding site (PB) at upstream of the Akt phosphorylation site in Girdin. (b) shows Vero cells which were transfected with either GFP-CT1 or GFP-CT1 in which the phosphoinositide-binding site was deleted (GFP-CT1 ΔPB). Arrows denote GFP signals at the plasma membrane.
Figure 6D:
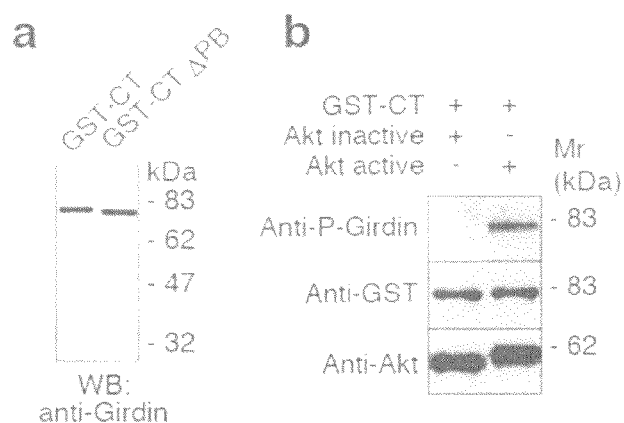
FIG. 6d shows purification of GST-CT and protein-lipid overlay assays. (a) shows purified GST-CT and GST-CT ΔPB which were respectively analyzed by Western blotting with anti-Girdin antibody. (b) shows phosphorylation of purified GST-CT by recombinant Akt in vitro. The phosphorylated GST-CT in the in vitro kinase assay was detected by anti-PGirdin antibody.
Figure 6E:
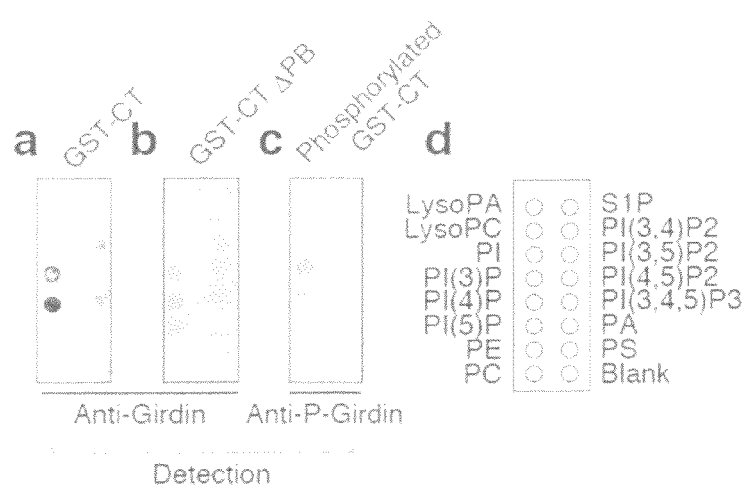
FIG. 6e shows protein-lipid overlay assays with GST-CT, GST-CT ΔPB and the phosphorylated GST-CT. The lipid binding of both GST-CT and GST-CT ΔPB was detected using anti-Girdin antibody, whereas that of phosphorylated GST-CT was detected by anti-P-Girdin antibody. The various lipids spotted on the membrane are indicated in (d).
Figure 6F:
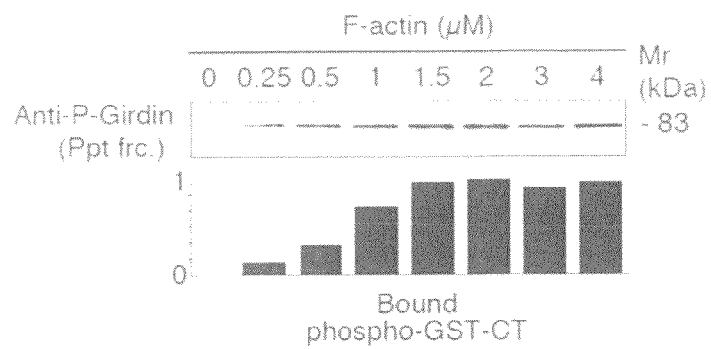
FIG. 6f shows binding of phosphorylated Girdin CT to F-actin. GST-CT was phosphorylated by Akt in vitro (cf.
Figure 6G:
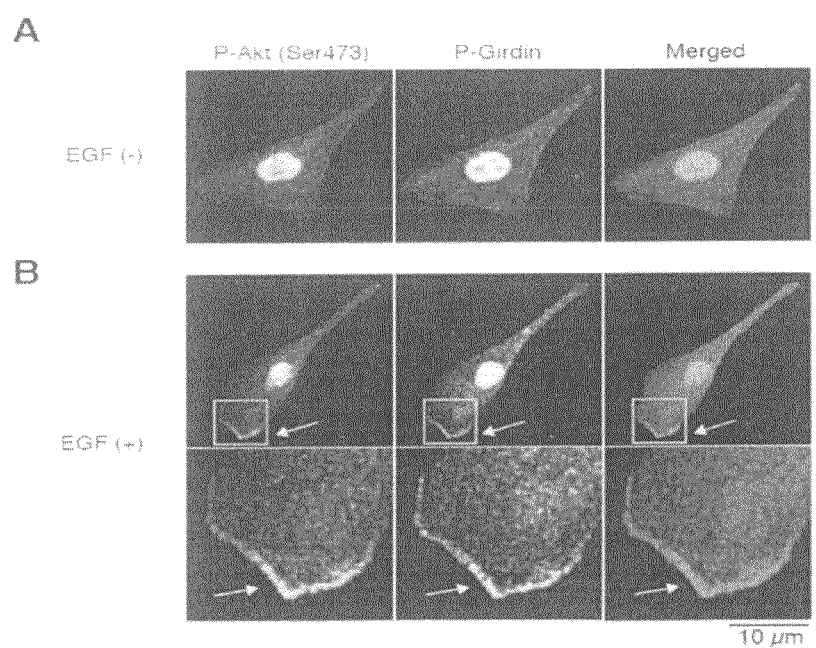
FIG. 6g shows colocalization of active Akt and phosphorylated Girdin at lamellipodia in EGF-stimulated Vero cells. Vero cells that had been serum starved for 24 hrs were either untreated as shown in (A) or treated with 50 ng/ml EGF as shown in (B), for 30 min, fixed, and costained with an anti-phospho Akt monoclonal antibody (green, Cell Signaling Technology) and an anti-phospho Girdin polyclonal antibody (red). Images were visualized by confocal microscopy. Arrows indicate colocalization of phosphorylated Akt and phosphorylated Girdin in lamellipodia at the leading edge. The regions in white boxes are shown magnified.

To gain insight into the role of Girdin phosphorylation by Akt, the location of phosphorylated Girdin in Vero cells was examined by staining with the anti-P-Girdin Ab. As shown in the upper panel in FIG. 6a, in serum-starved quiescent cells, phosphorylation of Girdin was hardly detected throughout the cells, consistent with the results of Western blot analyses shown in FIG. 2d. In cases where cells were stimulated with EGF (50 ng/ml), the immunostaining showed that phosphorylated Girdin appeared in the lamellipodia at the leading edge of migrating cells (FIG. 6a, middle panel). The phosphorylated Girdin was also colocalized with Cortactin that exists at the leading edge (FIG. 6b). Moreover, the stimulation of Vero cells with EGF enhanced the specific accumulation and localization of active Akt with phosphorylated Girdin in lamellipodia at the leading edge were observed (FIG. 6g). In the Girdin siRNA transfected cells, stimulation by EGF induced multiple leading edges, where the signals of phosphorylated Girdin were abolished as expected (FIG. 6a, bottom panel), further supporting the specificity of the immunostaining.

The following experiments were performed to determine the mechanism that determines localization differences between the phosphorylated and non-phosphorylated forms of Girdin. Because the CT1 domain of Girdin localizes to the plasma membrane and contains the phosphorylation site, it was hypothesized that it is the association of Girdin with the plasma membrane that is regulated by the phosphorylation. As shown in FIG. 6c (a), it was found that a positively charged sequence of 19 amino acid residues (Arg-1389 to Lys-1407) upstream of the phosphorylation site resembles a consensus sequence for phosphatidylinositol 4,5-bisphosphate (PI(4,5) P2) binding. When the GFP-CT1 in which the phosphoinositide-binding site was deleted was transfected into Vero cells, localization of the GFP-CT1 to the plasma membrane was not observed (FIG. 6c (b)). This finding suggested that the CT1 domain is anchored at the plasma membrane through binding to phosphoinositides.

Figure 6H:
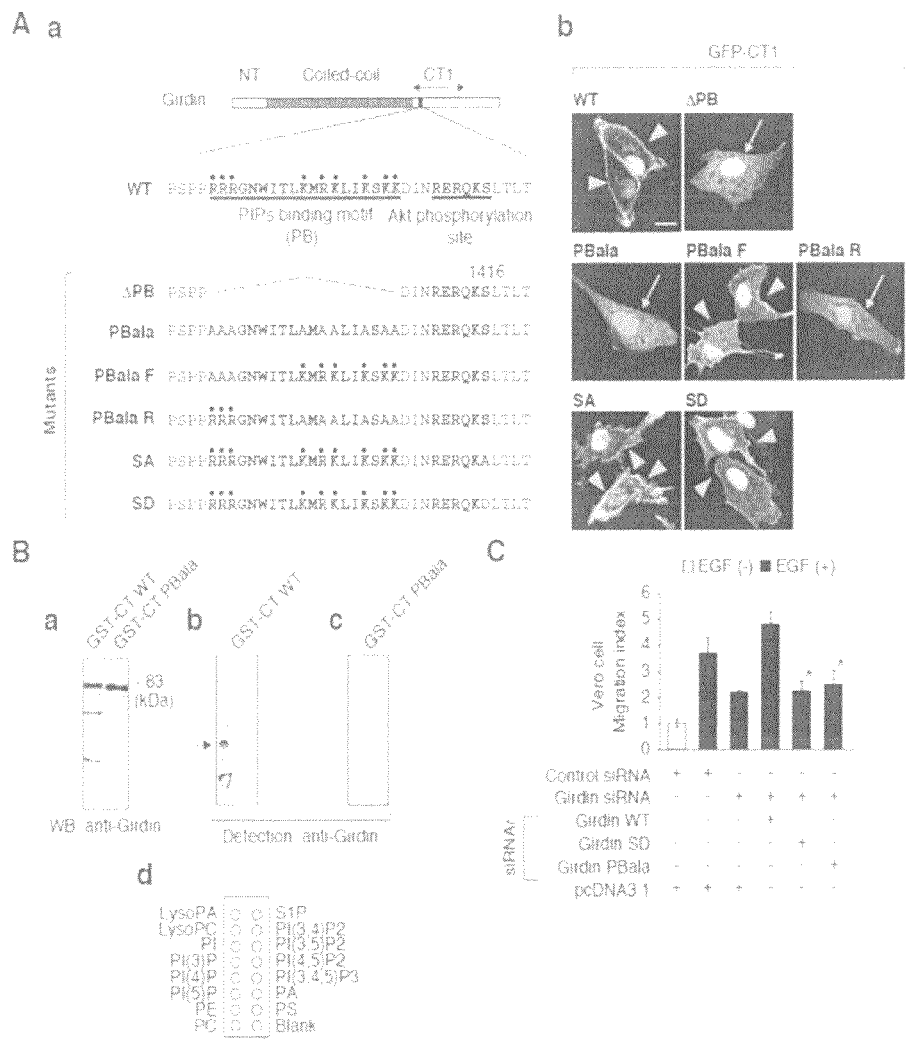
FIG. 6h shows effects of the amino-acid substitutions in the CT1 domain on the function of Girdin. (A) shows positive electrostatic charge in the putative phosphoinositide-binding (PB) site is required for the localization of the CT1 domain at the plasma membrane. Various CT1 mutants, in which either the positively charged residues (lysines or arginines) in the PB site were replaced with alanines (e.g., PBala, PBala F, and PBala R) or the Ser-1416 was replaced with alanine or aspartic acid (SA or SD), were generated as illustrated in (a) and their subcellular localization was examined in Vero cells as shown in (b). Arrowheads denote localization of GFP-CT1 at the plasma membrane, whereas arrows indicate that the mutants fail to localize to the plasma membrane. (B) shows the results for protein-lipid overlay assays. GST-CT wild type (WT) and GST-CT PBala, in which the positively charged residues in the PB site were replaced with alanines, were expressed in BL21-CodonPlus (Stratagene), purified as in (a), and subjected to protein-lipid overlay assays as in (b) and (c). (C) shows Vero cells were cotransfected with GFP (0.5 μg), siRNAs (20 pmol), and indicated siRNA-resistant (siRNAr) constructs (1 μg), incubated for 48 hrs, and subjected to Boyden chamber assays. Asterisks indicate stastical significance (Student's t test; *P<0.05) compared with WT.

To examine the phosphoinositide-binding properties of Girdin, a protein-lipid binding assay with purified GST fusion proteins containing the phosphoinositide-binding site of Girdin was performed. In the experiment, the CT domain fused with GST instead of the CT1 domain was utilized, because the GST-CT1 fusion protein was easily degraded during expression and purification procedures. As shown in FIG. 6e (a), GST-CT bound selectively to PI(4)P and weakly to PI(3) P, but to none of the other phosphoinositides or phospholipids. The binding property of GST-CT to PI(4)P and PI(3)P was abrogated when the phosphoinositide-binding site was deleted (FIG. 6e (b)). It was also found that mutants of the CT1 domain, in which the positively charged basic residues were replaced with alanines (Girdin PBala mutant), failed to bind to the phosphoinositides and were delocalized from the plasma membrane, suggesting that the positive electrostatic charge generated by the basic residues in the phosphoinositide binding motif is required for the association of Girdin with the plasma membrane (FIG. 6h).

Since the phosphoinositide-binding site is located near the Akt phosphorylation site (FIG. 6c (a), the supposition was made that Akt might control the localization of Girdin by regulation of its phosphoinositide-binding property. To determine if this is the case, the phosphoinositide-binding property of phosphorylated GST-CT was examined. Purified GST-CT was effectively phosphorylated by Akt in vitro (FIG. 6d (b)), followed by the protein-lipid binding assay, in which binding was detected by anti-P Girdin Ab. As shown in FIG. 6e (c), the phosphorylated GST-CT bound to neither PI(4)P nor PI(3)P. Moreover, actin cosedimentation assays showed that the phosphorylation of the GST-CT did not attenuate its affinity for F-actin and that the binding kinetics was similar to that of the GST-CT2 (FIGS. 6f and 3d. These findings suggested that the binding of Girdin to the phosphoinositides, but not to F-actin, is attenuated by phosphorylation.

Figure 6I:
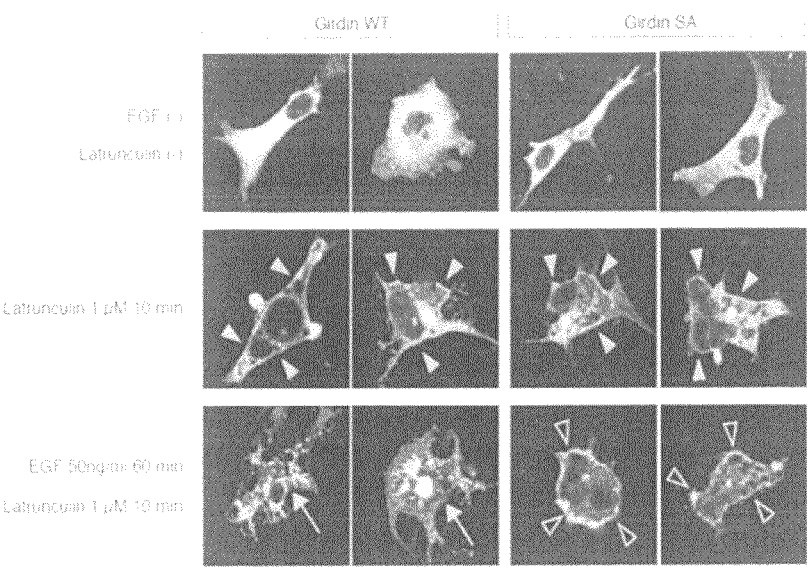
FIG. 6i shows regulation of membrane association of whole Girdin by EGF in Latrunculin-treated cells. (A) shows COS7 cells were transfected with either GFP-full-length Girdin wild type (WT) or SA mutant in which the Ser-1416 was replaced with alanine, and incubated for 24 hrs on glass base dishes. The cells, which were incubated with or without EGF (50 ng/ml) for 60 min, were treated with Latrunculin (1 μM, Calbiochem) for 10 min and fixed. When overexpressed in COS7 cells, both Girdin WT and SA diffusely localized throughout the cells except the nuclei (cf. upper panel). When cells were treated with Latrunculin that disrupts F-actin (cf. middle panel), both Girdin WT and SA were detected on the plasma membrane (cf. yellow arrowheads) as well as in the cytoplasm. When EGF-stimulated cells were treated with Latrunculin (cf. lower panel), the majority of Girdin WT was dissociated from the plasma membrane and accumulated in the cytoplasm in a punctuated pattern (cf. arrows). In contrast, Girdin SA remained associated with the plasma membrane after EGF stimulation (cf. yellow open arrowheads). (B) shows COS7 cells were transfected with GFP-full-length Girdin PBala mutant and treated with Latrunculin. The association of the mutant with the plasma membrane was hardly observed after Latrunculin treatment even in the absence of EGF.
Figure 6I:
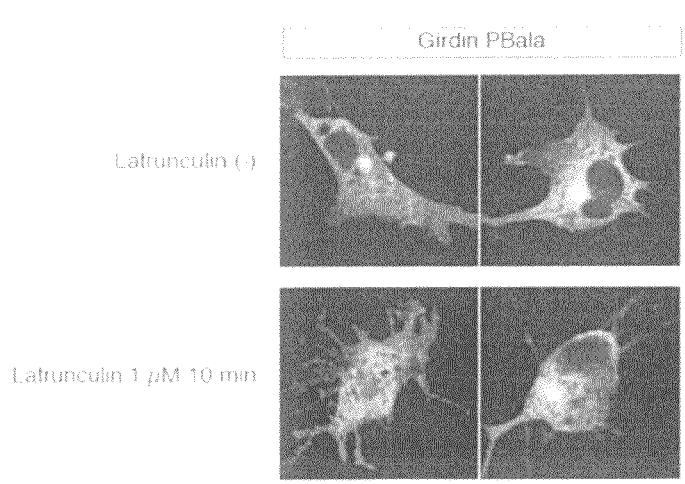

Moreover, whether the membrane association of Girdin is regulated by EGF treatment was investigated, using COS7 cells expressing either GFP-full length Girdin WT or SA mutant. As shown in FIG. 6i, the results supported the view that phosphorylation at the Ser-1416 by Akt is necessary for the delocalization of Girdin from the plasma membrane.

Example 7

Phosphorylation of Girdin by Akt Regulates Cell Migration

Figure 7A:
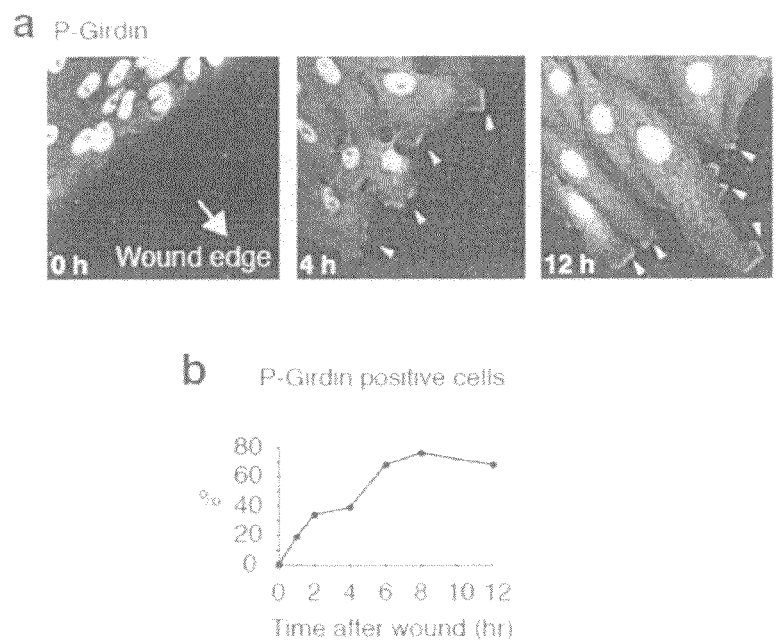
FIG. 7a shows Girdin is phosphorylated at the leading edge during cell migration. (a) shows after scratching a monolayer of Vero cells, the cells facing the wound were fixed and stained with anti-P-Girdin antibody. Arrowheads denote the signals of the phosphorylated Girdin. (b) shows the phosphorylation of Girdin localizing at the leading edge increases in a time-dependent fashion.
Figure 7B:
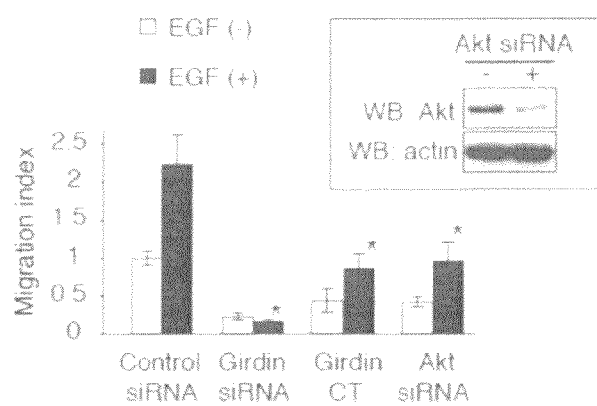
FIG. 7b shows Vero cells were transfected with GFP (0.5 μg) and either siRNA (20 pmol) or Girdin CT (2.5 μg), incubated for 48 hrs, and subjected to Boyden chamber assays in the presence or absence of EGF (100 ng/ml) in the lower chamber. Asterisks indicate statistical significance (Student's t test; P<0.05) compared with control. Inset shows the depletion of Akt in Vero cells by siRNA. Data were expressed as average±standard error.

The localization of phosphorylated Girdin at the leading edge prompted us to following test whether the phosphorylation of Girdin is involved in cell motility. After wounding a confluent monolayer of Vero cells, immunostaining with anti-P-Girdin Ab showed that the level of Girdin phosphorylation in cells at the wound edge increased soon after scratching, reached a maximum at 8 hrs, and lasted for at least 12 hrs (FIG. 7a). The implication is that the phosphorylation of Girdin may play an important role in cell motility. Thus, the role of Girdin in cell motility was examined using Boyden chamber assays. As shown in FIG. 7b, the Girdin knockdown significantly retarded the ability of Vero cells to migrate in response to EGF (50 ng/ml) added to the lower chamber. As shown in FIG. 7b, it was also found that expression of the CT domain in Vero cells significantly attenuated cell migration, supporting the notion that the interaction of endogenous Girdin with actin filaments is important for integral cell migration. Consistent with previous studies, the depletion of Akt by siRNA also attenuated the migration (FIG. 7B), which suggests that intrinsic Akt activity is requisite for Vero cells to migrate through the pores in this assay system.

Figure 7C:
FIG. 7c shows generation of an siRNA-resistant (siRNAr) mutant of Girdin. (a) shows the target sequence of Girdin siRNA (B in FIG. 4A) and the nucleotide substitution for the generation of siRNAr version indicated (due to addition of V5 tag to C-terminus of Giedin expressing constructs). (b) shows cell lysates from COS7 cells cotransfected with indicated siRNAs and constructs were analyzed by Western blotting with anti-V5 antibody.
Figure 7D:
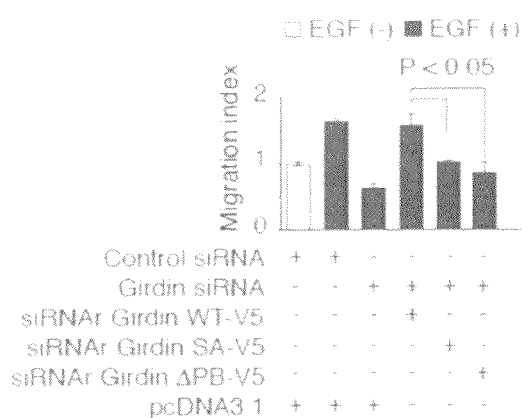
FIG. 7d shows Vero cells were cotransfected with GFP (0.5 μg), siRNAs (20 pmol), and indicated constructs (2.5 μg), incubated for 48 hrs, and subjected to Boyden chamber assays. Expression levels of Girdin mutants in cells prior to plating for migration assays were monitored by Western blot analysis with anti-V5 antibody, and were found to be similar (data not shown). Data were expressed as average±standard error.
Figure 7E:
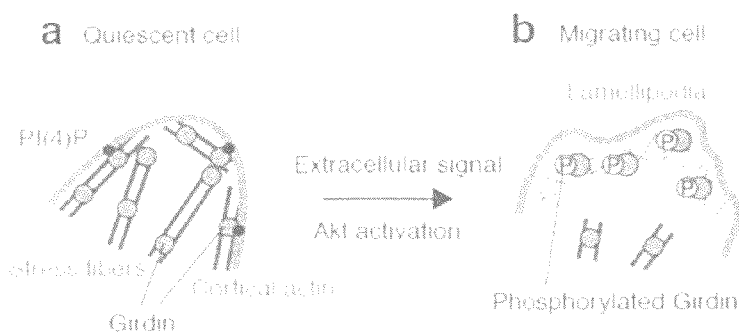
FIG. 7e shows a proposed model for the regulation of cell motility by the phosphorylation of Girdin. In quiescent cells, Girdin cross-links actin filaments and anchors cortical actin at the plasma membrane, whereas during cell migration, Akt-mediated phosphorylation allows Girdin to localize at the leading edge and contribute to the formation of shortbranched filaments in the lamellipodium.
Figure 7F:
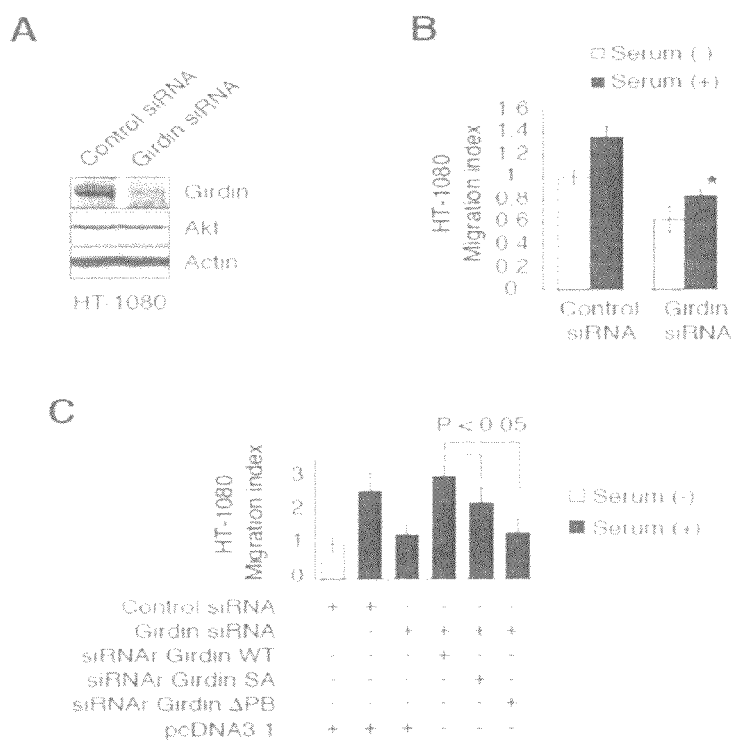
FIG. 7f shows Girdin is essential for directional migration in HT-1080 fibrosarcoma cells. (A) shows depletion of Girdin in HT-1080 cells. Total cell extracts from control siRNA- and Girdin siRNA-transfected HT-1080 cells were subjected to western blot analysis with anti-Girdin, anti-Akt, and anti-actin antibodies, which revealed that Girdin was specifically depleted 48 hrs after the transfection. (B) shows depletion of Girdin impairs directional migration of HT-1080 cells. Cells transfected with siRNAs were subjected to the Boyden chamber assay, in which serum (5%) was added in the lower chamber. *P<0.05 compared with control. (C) shows impaired cell migration by the depletion of Girdin was restored by adding back siRNA-resistant (siRNAr) version of Girdin. HT-1080 cells were cotransfected with GFP (0.5 µg), indicated siRNAs (20 pmol), and constructs (2.5 µg), and subjected to Boyden chamber assays 48 hrs after the transfection. The expression of siRNAr-Girdin wild type (WT) fully restored the cell migration, whereas SA and ΔPB versions did not. The results shown are representative of two independent experiments.

In order to examine whether adding Girdin exogenously restores the defect in cell migration observed in the knockdown cells, siRNA-resistant (siRNAr) versions of Girdin harboring silent mutations were constructed (FIG. 7c). As shown in FIG. 7d, the expression of the siRNAr-Girdin WT fully restored migratory response to EGF. In contrast, the expression of the siRNAr-Girdin mutants in which the Ser-1416 was mutated to Ala (siRNAr-Girdin SA), the phosphoinositide-binding site was deleted (siRNAr-Girdin ΔPB), or the basic residues in the phosphoinositide-binding site were replaced with alanines (siRNAr-Girdin PBala) failed to complement the migration defect (FIGS. 7d and 6h (c)). It was further confirmed these findings by performing migration assays using a human fibrosarcoma cell line, HT-1080 (FIG. 7f).

Figure 7G:
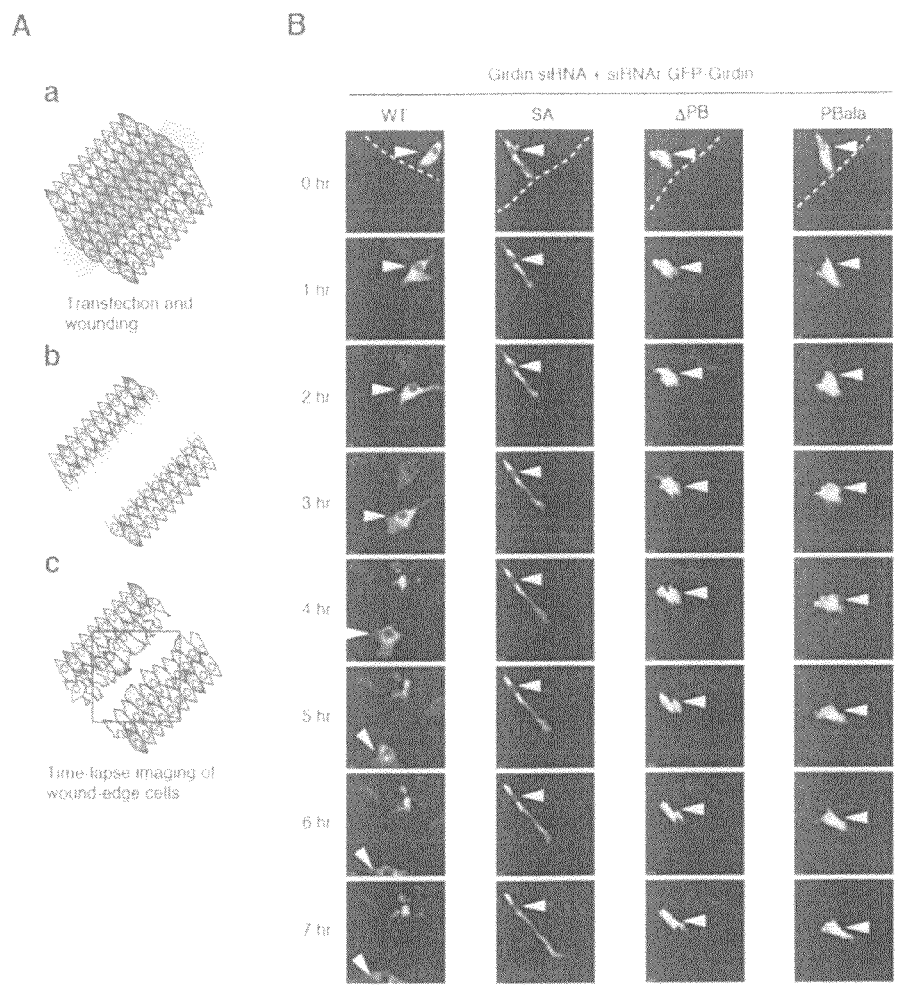
FIG. 7g shows effects of expression of Girdin mutants on directional migration of Vero cells. (A) shows observation of the movement of Vero cells expressing Girdin mutants by wound-healing assays. Confluent Vero cells on glass base dishes coated with fibronectin (10 µg/ml) were cotransfected with Girdin siRNA (20 pmol) and siRNA-resistant (siRNAr) wild-type GFP-Girdin (WT) and indicated mutants (SA, ΔPB, and PBala) (a). 48 hrs after the transfection, the cell monolayer was scratched to initiate cell migration into the wound (b), and cells expressing GFP-Girdin which face up to the wound were analyzed by time-lapse imaging (c). (B) shows time-lapse imaging of the movement of Vero cells expressing wild-type Girdin (WT) or indicated mutants (SA, ΔPB, and PBala). Images were collected every 90 sec for a period of 7 hrs starting 2 hrs after scratching. The white broken lines indicate the wound edge, and the arrowheads indicate the location of nuclei of migrating cells. The results are representative images of two independent experiments.

Finally, the movement of Vero cells expressing the Girdin mutants by wound-healing assays was directly examined (FIG. 7g). Cells expressing Girdin WT effectively and rapidly moved into the wound, but those expressing Girdin SA exhibited elongated shape and the location of the nuclei seemed to be fixed and motionless, suggesting that the cells could not undergo detachment from the matrix. Cells expressing Girdin ΔPB and Girdin PBala were less locomotive compared with those expressing Girdin WT. These results demonstrate that expression of the Girdin mutants impairs proper directional cell migration. Considered with the findings shown in FIG. 6a to 6f and FIG. 6i, these data indicate that the regulation of an interaction between Girdin and the plasma membrane by Akt is crucial for cell migration.

Example 8

Figure 8A:
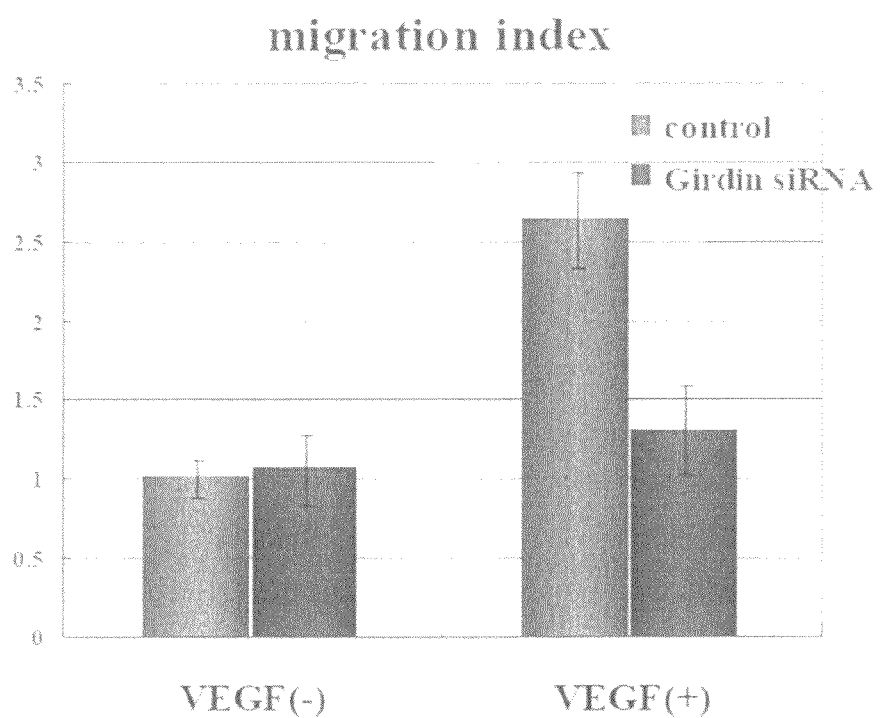
FIG. 8a shows quantitative determination results of migration ability of siRNA-transfected HUVEC cells by Boyden's chamber method.
Figure 8B:
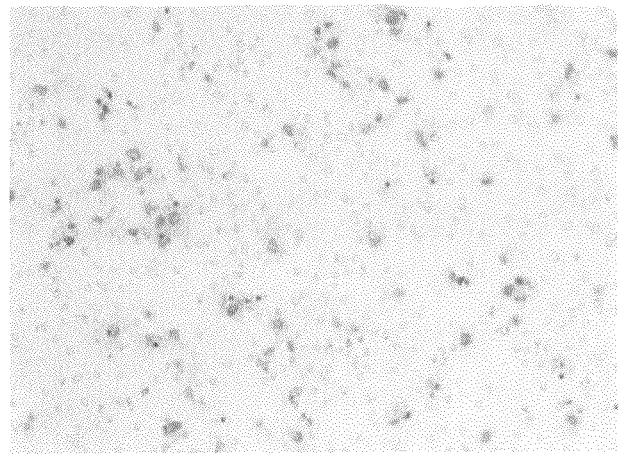
FIG. 8b shows stained images of migrated cells.
Figure 8B:
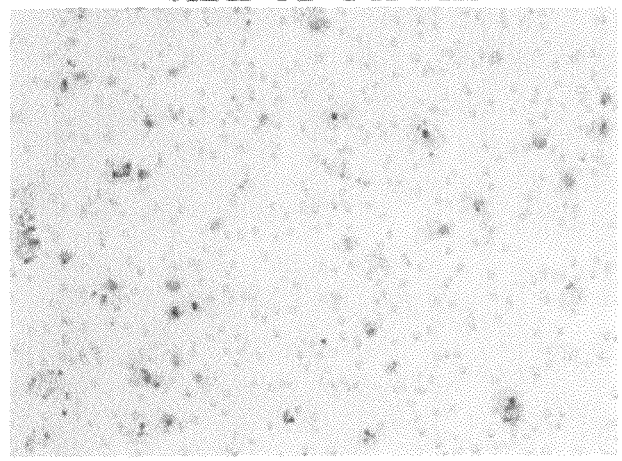

Inhibition of Migration Capability of Human Umbilical Vessel Endothelial Cell HUVEC by Girdin siRNA After HUVEC cell is processed by control siRNA and Girdin siRNA for 48 hours, migration capability by VEGF (vascular endothelial growth factor) was determined by Boyden Chamber method. As shown in FIG. 8a, it has been revealed that migration capability of HUVEC cell processed by Girdin siRNA in the presence of VEGF is reduced markedly. FIG. 8b shows migrated cells being stained to purple. As shown in FIG. 8b, it is apparent that the number of migratory cells of HUVEC cell processed by Girdin siRNA is reduced.

Example 9

Figure 9A:
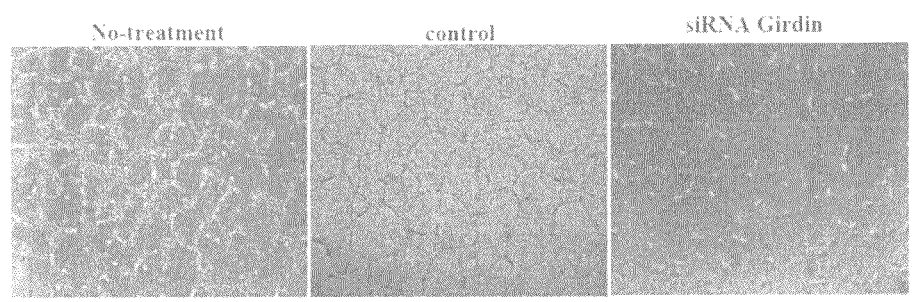
FIG. 9a shows observation results of lumen formation ability.
Figure 9B:
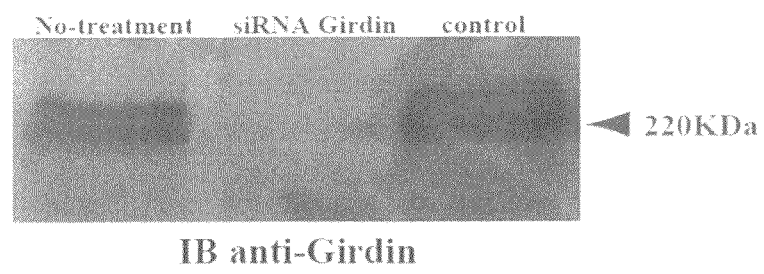
FIG. 9b shows Western blotting of detection with anti-Girdin antibody.

Inhibition of Lumen Formation Capability of Human Umbilical Vessel Endothelial Cell HUVEC by Girdin siRNA After HUVEC cell is processed by Girdin siRNA with a similar manner as Example 8, lumen formation capability was observed. Results of observation are shown in FIG. 9. As shown in FIG. 9a, although unprocessed HUVEC cell and HUVEC cell processed by the control siRNA show lumen formation under normal cultivation conditions, lumen formation was markedly inhibited in HUVEC cell processed by Girdin siRNA. FIG. 9b shows results of Western blotting of detection of Girdin expression in each cell shown in FIG. 9a by anti-Girdin antibody. As shown in FIG. 9b, with HUVEC cell to which Girdin siRNA is introduced, remarkable suppression of Girdin expression is noticed.

Example 10

Figure 10A:
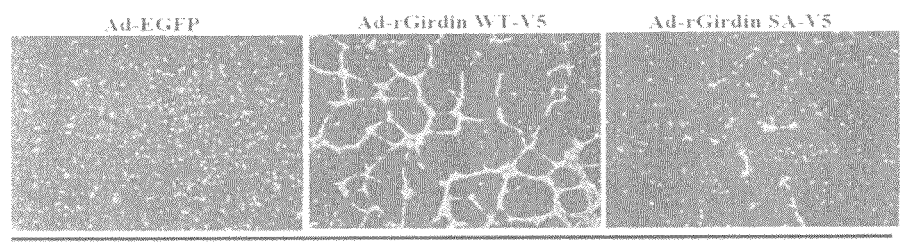
FIG. 10a shows recover of lumen formation ability.
Figure 10B:
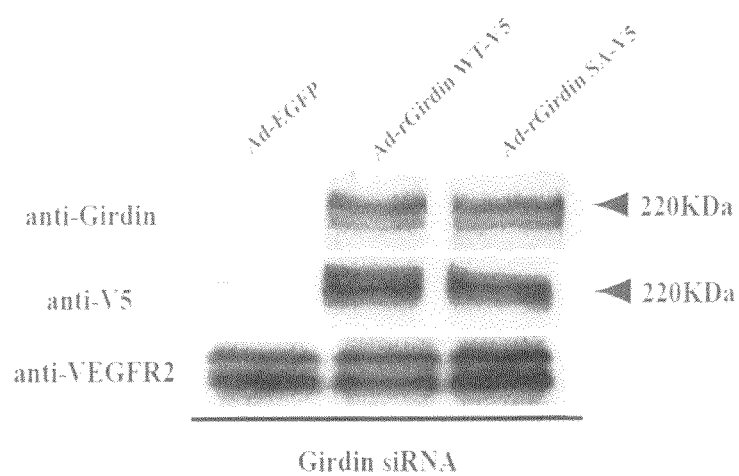
FIG. 10b shows Western blotting of detection with anti-Girdin antibody.

Recovery of Lumen Formation Capability by Expression of siRNA Resistant Girdin Gene cDNA of siRNA resistant Girdin gene was introduced to adenovirus vector (Ad-rGirdin WT-V5). Further, a vector to which Girdin cDNA, in which serine 1416, that is Akt phosphorylation side of Girdin, was replaced by alanine, was introduced, was also produced (Ad-rGirdin SA-V5). As shown in FIG. 10a, simultaneous introduction of siRNA and Ad-rGirdin WT-V5 into HUVEC cell resulted in recovery of lumen formation (center of FIG. 10a). It has been identified that when phosphorylation site by Akt is mutated, lumen formation is not recovered (right of FIG. 10a), and phosphorylation of Girdin by Akt plays an important role in this function. FIG. 10b shows results of Western blotting of detection of Girdin expression in each cell shown in FIG. 10a by anti-Girdin antibody and anti-V5 antibody. Meanwhile, expression of VEGFR2 (vascular endothelial growth factor receptor 2) is shown as the control.

It has been found from results described above that Girdin also plays an important role in angiogenesis, and there is a possibility of development of an antitumor drug aiming at inhibition of angiogenesis in tumors through development of Akt-Girdin family inhibitor compound.

Example 11

Matrigel Plug Assay

A knockdown vector for short hairpin type Girdin siRNA was constructed using adenovirus vector. Target sequence in Girdin gene was set to gaaggagaggcaactggat (SEQ ID NO: 3). 100 μl of the adenovirus ($1 \times 10^{10}$ pcs/ml) was mixed with 400 μl of matrigel containing VEGF 100 ng/ml (BD matrigel (product name)), and total dose thereof was injected subcutaneously to abdomen of a mouse. Matrigel injected site was removed 1 week later and stained with hematoxylin-eosin (HE). The same operations as observed for the example were performed except that adenovirus retaining EGFP was used as the control in lieu of knockdown cassette. Results obtained are shown in FIG. 11.

Figure 11:
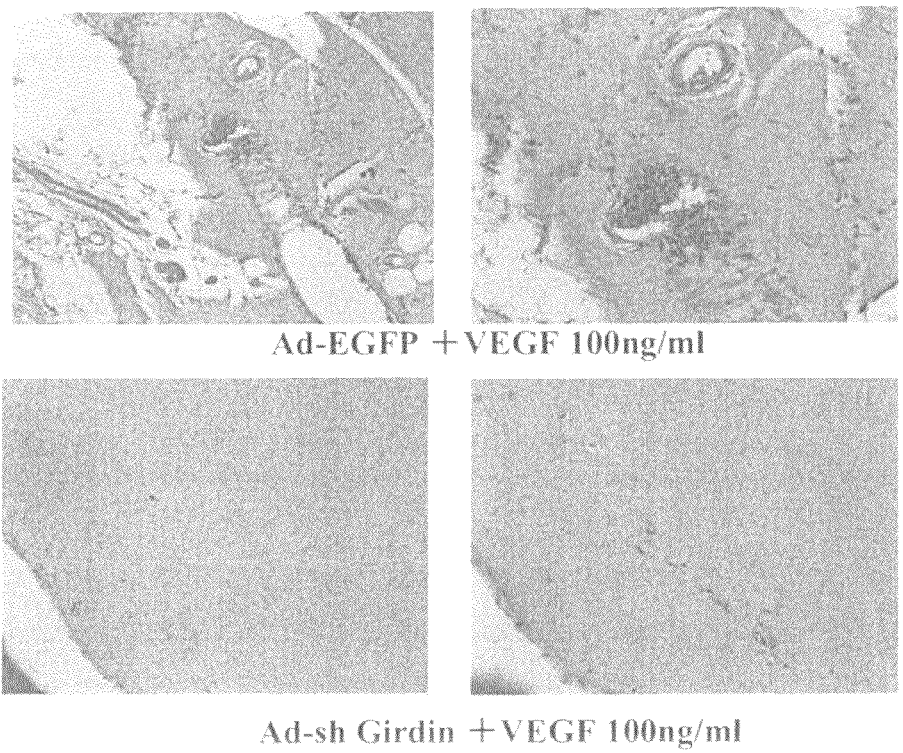
FIG. 11 shows Matrigel plug assay results of control (cf. upper panel) and mouse injected matrigel containing knockdown vector (cf. lower panel).

In FIG. 11, the upper panel shows results of the control and the lower panel shows results of the present example. Neoangiogenesis was observed with the control, while neoangiogenesis was observed little with the example. It is understood that as a result of suppression of Girdin expression, neoangiogenesis was inhibited. Meanwhile, it is confirmed that the knockdown vector used in the present example suppresses expression of Girdin.

Example 12

Expression of Girdin in Tumor Vessel

Figure 12:
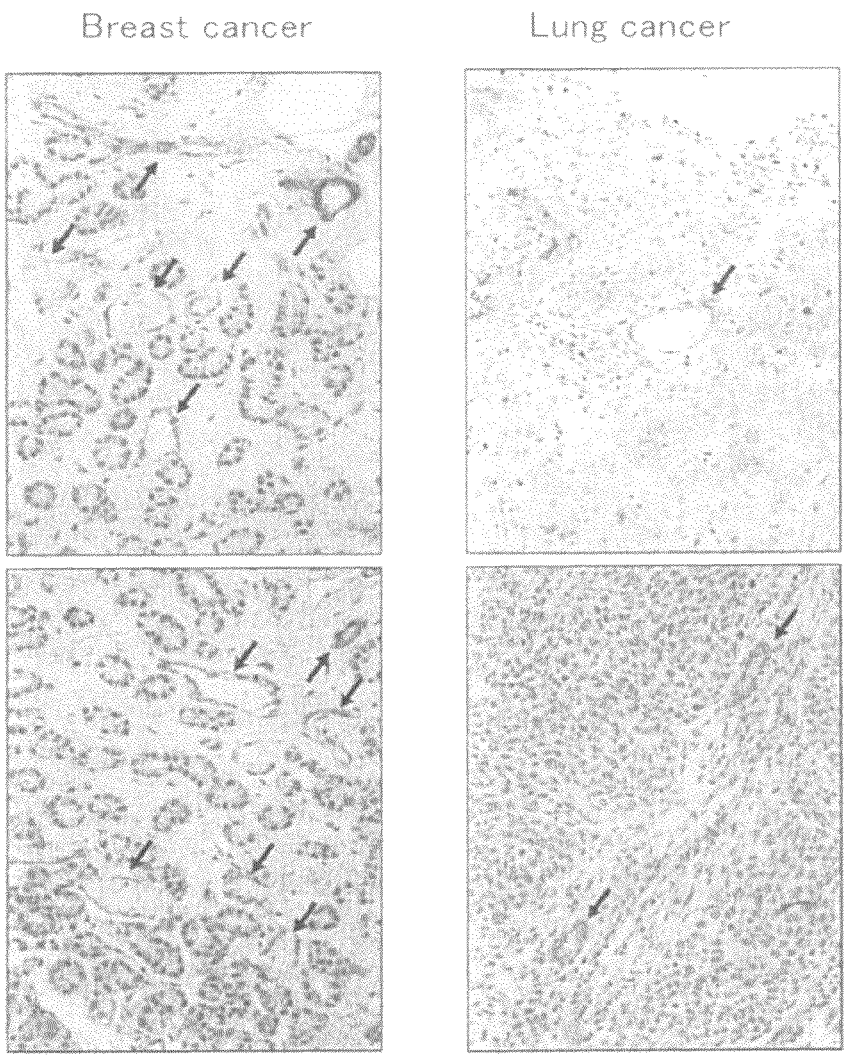
FIG. 12 shows Girdin immunostaining of tissues harvested from breast cancer and cervical cancer.

Tissues of human breast cancer and cervical cancer were harvested and Girdin was subjected to immunostaining by a prescribed method. Results are shown in FIG. 12. For Girdin tissue immunostaining, deparaffinization processing of paraffin-embedded sectioned tissue was performed using xylene, then subjected to dewatering process, endogenous peroxidase activity was inactivated by 0.3% hydrogen peroxide solution to allow blocking. After that, anti Girdin antibody (50-fold dilution by PBS containing BSA) was added, incubated in a moisturizing box (4° C., overnight), washed with PBS, and secondary antibody was added and incubated at room temperature (15 min). After having been washed with PBS, enzyme labeling streptavidin was added, incubated at room temperature for 15 min, washed, and DAB substrate was added. After the reaction had been stopped by immersing into PBS, nuclear staining was performed by hematoxylin staining, washed and dehydrated, and then subjected to xylene treatment. It can be recognized from FIG. 12 that Girdin is stained markedly in vessel endothelial cell (arrows denote markedly stained portion by Girdin). It has been discovered from these results that Girdin expresses markedly in the endothelial cell of tumor vessel.

INDUSTRIAL APPLICABILITY

Present teachings disclosed in the specification are applicable to drugs for preventing/treating of various diseases, screening methods of the drugs, and reagents.

What is claimed is:

1. An isolated antibody specific for a polypeptide comprising an amino acid sequence having at least 95% sequence identity with the amino acid sequence of SEQ ID NO:2 and having the serine residue at position 1416 of SEQ ID NO: 2, wherein the antibody recognizes a portion of the polypeptide delineated by the amino acid residues at positions 1408-1420 of SEQ ID NO: 2.

2. The antibody of claim 1, wherein the antibody only specifically binds to the polypeptide when the serine residue at position 1416 of SEQ ID NO: 2 is phosphorylated.

3. An isolated antibody specific for a polypeptide comprising the amino acid sequence of SEQ ID NO: 2, wherein the antibody only specifically binds the polypeptide when the serine residue at position 1416 of SEQ ID NO: 2 is phosphorylated.

4. The antibody of claim 1, wherein the antibody is monoclonal.

5. The antibody of claim 1, wherein the antibody is polyclonal.

6. The antibody of claim 1, wherein the antibody is immobilized to a carrier.

7. An isolated antibody specific for an antigenic peptide of SEQ ID NO: 2, the antigenic peptide comprising the serine residue at position 1416 of SEQ ID NO: 2.

8. The antibody of claim 7, wherein the antibody only specifically binds the peptide when the serine residue at position 1416 of SEQ ID NO: 2 is phosphorylated.

9. A reagent comprising the antibody of claim 1.

10. The reagent of claim 9, wherein the reagent is a diagnostic reagent.

11. The reagent of claim 9, wherein the reagent is a research reagent.

12. A kit comprising the antibody of claim 1.

13. The kit of claim 12, wherein the kit is a diagnostic kit.

14. The kit of claim 12, wherein the kit is a research kit.

15. A diagnostic reagent for disorders involving any of cell motility, cell movement or angiogenesis, comprising the antibody of claim 1.

16. A diagnostic reagent for cancer comprising the antibody of claim 1.

17. A reagent for conducting research on activation or inhibition of any of cell motility, cell movement or angiogenesis, comprising the antibody of claim 1.

18. An array comprising the antibody of claim 1.

19. An assay comprising the antibody of claim 1.

20. The assay of claim 19, wherein the assay is an enzyme immunoassay (EIA).

21. The assay of claim 19, wherein the assay is an enzyme-linked immunosorbent assay (ELISA).

22. A hybridoma that produces the antibody of claim 1.

23. A method comprising:
contacting a sample with the antibody of claim 1; and
detecting a protein for which the antibody is specific when present in the sample.

24. A method comprising:
contacting a sample with the antibody of claim 1; and
quantifying the amount of a protein for which the antibody is specific when present in the sample.

25. A method comprising:
contacting a sample with the antibody of claim 1, the antibody being immobilized on a carrier; and
immunoprecipitating a protein for which the antibody is specific when present in the sample.

26. The antibody of claim 2, wherein the antibody is monoclonal.

27. The antibody of claim 2, wherein the antibody is polyclonal.

28. The antibody of claim 2, wherein the antibody is immobilized to a carrier.

29. A reagent comprising the antibody of claim 2.

30. The reagent of claim 29, wherein the reagent is a diagnostic reagent.

31. The reagent of claim 29, wherein the reagent is a research reagent.

32. A kit comprising the antibody of claim 2.

33. The kit of claim 32, wherein the kit is a diagnostic kit.

34. The kit of claim 32, wherein the kit is a research kit.

35. A diagnostic reagent for disorders involving any of cell motility, cell movement or angiogenesis, comprising the antibody of claim 2.

36. A diagnostic reagent for cancer comprising the antibody of claim 2.

37. A reagent for conducting research on activation or inhibition of any of cell motility, cell movement or angiogenesis, comprising the antibody of claim 2.

38. An array comprising the antibody of claim 2.

39. An assay comprising the antibody of claim 2.

40. The assay of claim 39, wherein the assay is an enzyme immunoassay (EIA).

41. The assay of claim 39, wherein the assay is an enzyme-linked immunosorbent assay (ELISA).

42. A hybridoma that produces the antibody of claim 2.

43. A method comprising:
contacting a sample with the antibody of claim 2; and
detecting a protein for which the antibody is specific when present in the sample.

44. A method comprising:
contacting a sample with the antibody of claim 2; and
quantifying the amount of a protein for which the antibody is specific when present in the sample.

45. A method comprising:
contacting a sample with the antibody of claim 2, the antibody being immobilized on a carrier; and
immunoprecipitating a protein for which the antibody is specific when present in the sample.

* * * * *

SEQUENCE LISTING

```
<160> NUMBER OF SEQ ID NOS: 3

<210> SEQ ID NO 1
<211> LENGTH: 5613
<212> TYPE: DNA
<213> ORGANISM: Homo sapiens

<400> SEQUENCE: 1
atggagaacg aaattttac tccccttctg gagcagttca tgaccagccc tttggtcact      60
tgggttaaaa cgtttggacc tctggccgca ggaaatggga ccaaccttga tgaatatgtg     120
gctttggtgg atggggtatt cttgaaccag gtcatgctcc aaattaatcc taaattggag    180
agtcagagag taaataaaaa agtcaataat gatgcctcac ttagaatgca caatctatcc    240
attttggtga gacagataaa attttattac caggagactt tgcagcaatt gatcatgatg    300
tcgttgccaa atgtcttaat cattggcaaa aatcccttt ctgaacaagg cacagaagaa     360
gttaaaaaac tgcttttact tttattgggt tgtgcagttc agtgtcagaa aaaagaggaa    420
tttattgaaa gaattcaagg tttagatttt gatacaaaag cagcggttgc cgcacatatt    480
caagaggtaa ctcataatca ggaaaatgtg tttgacctgc aatggatgga agtgactgat    540
atgtcgcagg aggacataga accactcttg aaaaatatgg cattgcatct aaaaagactt    600
atagatgaga gagatgaaca ttcagagact atcatagaac tctctgaaga gcgggatggt    660
ctccattttc taccccatgc ctcttcatct gcacagtcac cctgtggttc tccaggcatg    720
aagcgaacag aaagtcgaca acatctgtcg gtggaactgg cagatgctaa agccaagata    780
agaaggctta ggcaggaatt ggaggaaaag actgagcagt tgttggattg taaacaagaa    840
cttgagcaaa tggaaataga actcaaaagg ctgcaacaag agaacatgaa tttgctttcg    900
gatgctcgct ctgccagaat gtaccgagat gaattagatg cacttcgaga gaaagcagtc    960
agagtcgata agcttgaaag tgaagtcagc agatataaag agagactaca tgatattgaa   1020
ttttataagg caagagttga ggaattaaaa gaagacaatc aagttttatt agaaacaaaa   1080
accatgttgg aagaccaact agagggaact cgtgctcgtt ccgataaatt acatgaatta   1140
gaaaaagaga acttacaact gaaagctaaa cttcatgata tggaaatgga acgagatatg   1200
gatagaaaaa agattgaaga attaatgaa gaaaatatga ctttggaaat ggcacagaaa   1260
caaagtatgg atgaatcatt acatcttggc tgggaactgg aacagatatc cagaactagt   1320
gaactttccg aagcacccca gaaatccctg ggccatgagg tgaatgagtt gacatcaagt   1380
agattattga agctagagat ggaaaatcaa agtttgacaa aaaccgtgga agagcttcgg   1440
actactgtgg attctgtaga aggcaatgct tccaaaatcc tgaaaatgga aaaagaaaat   1500
caaaggctca gtaaaaaggt tgagattctt gaaaatgaga ttgttcaaga aaagcaaagt   1560
cttcagaatt gtcagaattt aagcaaggat ctaatgaagg agaaagctca gcttgaaaaa   1620
```

```
acaatagaaa cactgagaga aaattcagag agacagatta agatactgga acaggaaaat  1680
gaacatctga atcaaacagt gtcttcctta aggcagcggt cccagataag tgcagaagca  1740
agagtgaaag acattgaaaa agaaaacaaa attcttcatg aatctatcaa agaaacaagt  1800
agcaagctaa gcaagattga atttgaaaaa agacaaatta aaaagaatt ggaacattat  1860
aaagaaaaag gagaacgagc tgaagaactt gaaatgaat tgcatcatct tgaaaaagaa  1920
aatgaattat tacagaaaaa ataactaat ttaaaaatta cttgtgaaaa aattgaggcc  1980
ttagaacaag aaaattcaga gctagaaaga gaaatagaa aattaaaaaa aacattggat  2040
agctttaaaa atctgacctt tcagttagaa tccctagaaa aagagaattc ccaacttgat  2100
gaggaaaact tagaactgcg aaggaatgta gaatctttga agtgtgcaag catgaaaatg  2160
gctcagctac agctagaaaa caaagaactg gaaagtgaaa aagagcaact taagaagggt  2220
ttggagctcc tgaaagcatc tttcaagaaa acagaacgct tagaagttag ctaccagggt  2280
ttagatatag aaaatcaaag actgcaaaaa actttagaga acagcaataa aaaaatccag  2340
caattagaga gtgaactaca agacttagag atggaaaatc aaacattgca gaaaaaccta  2400
gaagaactaa aaatatctag caaaagacta gaacagctgg aaaaagaaaa taatcatta  2460
gagcaagaga cttctcaact ggaaaaggat aagaaacaat tggagaagga aaataagaga  2520
ctccgacaac aagcagaaat taagatacc acattagaag aaaataatgt gaagattgga  2580
aatttggaaa agaaaacaa aaccctatcc aaagaaattg gtatatataa agaatcttgt  2640
gtccgtctga aagaactaga aaagaaaat aaggagcttg tgaaaagagc aactattgat  2700
ataaaaacgt tggttacact acgtgaggat ttggtgagtg aaaagttgaa gacccaacag  2760
atgaacaatg atctcgaaaa attaactcat gagcttgaga agatagggtt aaataaggag  2820
cgactcttac atgatgaaca aagtactgat gacaggtata aacttttgga atcaaaatta  2880
gaatccactc ttaagaagtc tcttgaaata aaagaagaaa aaattgctgc tttagaagct  2940
cgattagaag aatccacgaa ttataaccag caattgcgcc aagaacttaa aacagtgaaa  3000
aaaaattatg aagctctcaa acagagacaa gatgaggaaa ggatggtaca gagctctcct  3060
ccaatatctg gtgaagacaa caaatgggag cgagaaagtc aagaaacgac tagagaactt  3120
ctgaaagtta agacagatt aattgaagta gaaagaaata atgctacact gcaagcagag  3180
aagcaagcgt tgaaaactca actgaagcaa cttgagacac agaacaataa tttgcaggct  3240
cagattcttg cacttcagag gcagacagtg tcattacaag aacagaatac cactcttcaa  3300
acacagaatg ccaagcttca ggttgaaaat tccacccta attcccaaag tacctcactc  3360
atgaaccaga atgcccaact cctaatccag cagtcttcct tagaaaatga aatgaatct  3420
gtaatcaaag agcgagaaga cctaaaatct ctctatgatt ctctgatcaa agatcatgaa  3480
aagctggaac ttcttcatga acgtcaggct tcagagtatg aatctcttat ctctaaacat  3540
ggaactctga agtctgccca caaaaatctt gaggtggaac atagagacct tgaagaccgt  3600
tacaatcagt tattaaaaca gaaaggacag ttggaagatt tggaaaaaat gctcaaagta  3660
gaacaggaaa aaatgctgct tgaaaataaa aatcatgaaa cagtagctgc agaatacaag  3720
aaactttgtg gtgaaaatga taggctgaat catacctata gtcaactttt aaaagagact  3780
gaagttttac aaactgacca taaaaatttg aaagtcttc tgaataattc caaactggaa  3840
caaacaagat tagaagctga attttcaaaa ctaaaggaac aataccaaca attggatatt  3900
acatcaacca agctgaataa ccagtgtgag ttgctaagcc aacttaaagg aaatttagaa  3960
gaagaaaatc ggcatctact agatcaaatt cagacattaa tgctacagaa cagaacactt  4020
```

-continued

```
ttggagcaga atatggaaag caaggatctt tttcatgttg aacaaagaca gtacattgat    4080
aagttaaatg aattaagacg tcagaaggag aaactagaaa gaaaattat ggatcaatac     4140
aaatttatg acccatctcc tcctagaagg agaggcaact ggattactct aaaaatgaga    4200
aaattgataa agtctaagaa agatattaat cgggaacgcc agaaatctct aacattaaca    4260
cccacccgct cagactccag tgaaggattt cttcagctcc ctcatcaaga cagtcaagat    4320
agttcttcag taggttcaaa ctcttagaa gatggccaga ccttggggac caagaaaagc     4380
agcatggttg cactgaaaag actgcccttt tgaggaaca gaccgaagga taaagacaaa     4440
atgaaggcct gctaccgtcg ttccatgtcc atgaatgacc tggtgcagtc catggtccta    4500
gcaggacagt ggacaggtag tactgagaat ttggaggttc ctgatgatat ttcaacgggt    4560
aaaaggagaa aagaattggg agctatggcc ttctctacta cagccatcaa cttttcaact    4620
gtcaactctt ctgcaggctt cagatccaag cagttggtta ataataaaga tactacatcc    4680
tttgaagaca taagtccaca aggtgttagt gatgattcta gtacgggatc aagagttcat    4740
gcttcaagac cagccagcct tgatagtggc agaacatcca ctagcaatag caataataat    4800
gcttcactac atgaagtcaa agcaggtgca gttaataacc aaagcaggcc acaaagccac    4860
agcagtggag aatttagcct gcttcatgac catgaggctt ggtccagcag tggtagcagt    4920
ccaatccagt acttgaaaag acagaccaga tcaagcccag tgctccagca caaaatatct    4980
gaaacactgg agagtcgaca tcacaagatc aaaactggtt cccctggaag tgaagttgtt    5040
actctacaac agttttttgga agaaagcaat aagcttacct cagtacagat aaagtcctca    5100
agtcaagaga atcttttaga tgaagtaatg aaaagtttgt ctgtctcttc tgactttttg    5160
ggaaaagaca aaccagttag ctgtggtctg gccaggtcag taagtggaaa acccccaggg    5220
gacttctatg atagacggac aactaagcct gagtttttga gacctggtcc tcgaaaaact    5280
gaagatacct acttcattag ttctgcggga aaacctacac caggcactca aggaaaaata    5340
aaattagtaa aagaatcttc tctgtcacga caatcaaaag atagtaaccc ttatgcaact    5400
ttacctcgtg caagcagcgt gatctcaact gccgaaggaa ctacacgaag acaagcatc     5460
catgattttt tgaccaagga cagtagactg cctatatcag ttgattcacc accagctgct    5520
gctgacagca acaccactgc agcatctaat gtggacaaag tacaagaaag cagaaattca    5580
aaaagcaggt ctagggagca acaaagctcc taa                                 5613
```

<210> SEQ ID NO 2
<211> LENGTH: 1870
<212> TYPE: PRT
<213> ORGANISM: Homo Sapiens

<400> SEQUENCE: 2

```
Met Glu Asn Glu Ile Phe Thr Pro Leu Leu Glu Gln Phe Met Thr Ser
1               5                   10                  15

Pro Leu Val Thr Trp Val Lys Thr Phe Gly Pro Leu Ala Ala Gly Asn
            20                  25                  30

Gly Thr Asn Leu Asp Glu Tyr Val Ala Leu Val Asp Gly Val Phe Leu
        35                  40                  45

Asn Gln Val Met Leu Gln Ile Asn Pro Lys Leu Glu Ser Gln Arg Val
    50                  55                  60

Asn Lys Lys Val Asn Asn Asp Ala Ser Leu Arg Met His Asn Leu Ser
65                  70                  75                  80

Ile Leu Val Arg Gln Ile Lys Phe Tyr Tyr Gln Glu Thr Leu Gln Gln
```

```
                     85                  90                  95
Leu Ile Met Met Ser Leu Pro Asn Val Leu Ile Ile Gly Lys Asn Pro
                100                 105                 110
Phe Ser Glu Gln Gly Thr Glu Val Lys Lys Leu Leu Leu Leu
            115                 120                 125
Leu Gly Cys Ala Val Gln Cys Gln Lys Lys Glu Glu Phe Ile Glu Arg
130                 135                 140
Ile Gln Gly Leu Asp Phe Asp Thr Lys Ala Ala Val Ala Ala His Ile
145                 150                 155                 160
Gln Glu Val Thr His Asn Gln Glu Asn Val Phe Asp Leu Gln Trp Met
                165                 170                 175
Glu Val Thr Asp Met Ser Gln Glu Asp Ile Glu Pro Leu Leu Lys Asn
                180                 185                 190
Met Ala Leu His Leu Lys Arg Leu Ile Asp Glu Arg Asp Glu His Ser
                195                 200                 205
Glu Thr Ile Ile Glu Leu Ser Glu Glu Arg Asp Gly Leu His Phe Leu
                210                 215                 220
Pro His Ala Ser Ser Ala Gln Ser Pro Cys Gly Ser Pro Gly Met
225                 230                 235                 240
Lys Arg Thr Glu Ser Arg Gln His Leu Ser Val Glu Leu Ala Asp Ala
                245                 250                 255
Lys Ala Lys Ile Arg Arg Leu Arg Gln Glu Leu Glu Glu Lys Thr Glu
                260                 265                 270
Gln Leu Leu Asp Cys Lys Gln Glu Leu Glu Gln Met Glu Ile Glu Leu
                275                 280                 285
Lys Arg Leu Gln Gln Glu Asn Met Asn Leu Leu Ser Asp Ala Arg Ser
                290                 295                 300
Ala Arg Met Tyr Arg Asp Glu Leu Asp Ala Leu Arg Glu Lys Ala Val
305                 310                 315                 320
Arg Val Asp Lys Leu Glu Ser Glu Val Ser Arg Tyr Lys Glu Arg Leu
                325                 330                 335
His Asp Ile Glu Phe Tyr Lys Ala Arg Val Glu Glu Leu Lys Glu Asp
                340                 345                 350
Asn Gln Val Leu Leu Glu Thr Lys Thr Met Leu Glu Asp Gln Leu Glu
                355                 360                 365
Gly Thr Arg Ala Arg Ser Asp Lys Leu His Glu Leu Glu Lys Glu Asn
                370                 375                 380
Leu Gln Leu Lys Ala Lys Leu His Asp Met Glu Met Glu Arg Asp Met
385                 390                 395                 400
Asp Arg Lys Lys Ile Glu Glu Leu Met Glu Glu Asn Met Thr Leu Glu
                405                 410                 415
Met Ala Gln Lys Gln Ser Met Asp Glu Ser Leu His Leu Gly Trp Glu
                420                 425                 430
Leu Glu Gln Ile Ser Arg Thr Ser Glu Leu Ser Glu Ala Pro Gln Lys
                435                 440                 445
Ser Leu Gly His Glu Val Asn Glu Leu Thr Ser Ser Arg Leu Leu Lys
                450                 455                 460
Leu Glu Met Glu Asn Gln Ser Leu Thr Lys Thr Val Glu Glu Leu Arg
465                 470                 475                 480
Thr Thr Val Asp Ser Val Glu Gly Asn Ala Ser Lys Ile Leu Lys Met
                485                 490                 495
Glu Lys Glu Asn Gln Arg Leu Ser Lys Lys Val Glu Ile Leu Glu Asn
                500                 505                 510
```

```
Glu Ile Val Gln Glu Lys Gln Ser Leu Gln Asn Cys Gln Asn Leu Ser
            515                 520                 525

Lys Asp Leu Met Lys Glu Lys Ala Gln Leu Glu Lys Thr Ile Glu Thr
        530                 535                 540

Leu Arg Glu Asn Ser Glu Arg Gln Ile Lys Ile Leu Glu Gln Glu Asn
545                 550                 555                 560

Glu His Leu Asn Gln Thr Val Ser Ser Leu Arg Gln Arg Ser Gln Ile
                565                 570                 575

Ser Ala Glu Ala Arg Val Lys Asp Ile Glu Lys Glu Asn Lys Ile Leu
            580                 585                 590

His Glu Ser Ile Lys Glu Thr Ser Ser Lys Leu Ser Lys Ile Glu Phe
        595                 600                 605

Glu Lys Arg Gln Ile Lys Lys Glu Leu Glu His Tyr Lys Glu Lys Gly
    610                 615                 620

Glu Arg Ala Glu Glu Leu Glu Asn Glu Leu His His Leu Glu Lys Glu
625                 630                 635                 640

Asn Glu Leu Leu Gln Lys Lys Ile Thr Asn Leu Lys Ile Thr Cys Glu
                645                 650                 655

Lys Ile Glu Ala Leu Glu Gln Glu Asn Ser Glu Leu Glu Arg Glu Asn
            660                 665                 670

Arg Lys Leu Lys Lys Thr Leu Asp Ser Phe Lys Asn Leu Thr Phe Gln
        675                 680                 685

Leu Glu Ser Leu Glu Lys Glu Asn Ser Gln Leu Asp Glu Glu Asn Leu
    690                 695                 700

Glu Leu Arg Arg Asn Val Glu Ser Leu Lys Cys Ala Ser Met Lys Met
705                 710                 715                 720

Ala Gln Leu Gln Leu Glu Asn Lys Glu Leu Glu Ser Glu Lys Glu Gln
                725                 730                 735

Leu Lys Lys Gly Leu Glu Leu Leu Lys Ala Ser Phe Lys Lys Thr Glu
            740                 745                 750

Arg Leu Glu Val Ser Tyr Gln Gly Leu Asp Ile Glu Asn Gln Arg Leu
        755                 760                 765

Gln Lys Thr Leu Glu Asn Ser Asn Lys Lys Ile Gln Gln Leu Glu Ser
    770                 775                 780

Glu Leu Gln Asp Leu Glu Met Glu Asn Gln Thr Leu Gln Lys Asn Leu
785                 790                 795                 800

Glu Glu Leu Lys Ile Ser Ser Lys Arg Leu Glu Gln Leu Glu Lys Glu
                805                 810                 815

Asn Lys Ser Leu Glu Gln Glu Thr Ser Gln Leu Glu Lys Asp Lys Lys
            820                 825                 830

Gln Leu Glu Lys Glu Asn Lys Arg Leu Arg Gln Gln Ala Glu Ile Lys
        835                 840                 845

Asp Thr Thr Leu Glu Glu Asn Asn Val Lys Ile Gly Asn Leu Glu Lys
    850                 855                 860

Glu Asn Lys Thr Leu Ser Lys Glu Ile Gly Ile Tyr Lys Glu Ser Cys
865                 870                 875                 880

Val Arg Leu Lys Glu Leu Glu Lys Glu Asn Lys Glu Leu Val Lys Arg
                885                 890                 895

Ala Thr Ile Asp Ile Lys Thr Leu Val Thr Leu Arg Glu Asp Leu Val
            900                 905                 910

Ser Glu Lys Leu Lys Thr Gln Gln Met Asn Asn Asp Leu Glu Lys Leu
        915                 920                 925
```

-continued

```
Thr His Glu Leu Glu Lys Ile Gly Leu Asn Lys Glu Arg Leu Leu His
930                 935                 940

Asp Glu Gln Ser Thr Asp Asp Arg Tyr Lys Leu Leu Glu Ser Lys Leu
945                 950                 955                 960

Glu Ser Thr Leu Lys Lys Ser Leu Glu Ile Lys Glu Glu Lys Ile Ala
            965                 970                 975

Ala Leu Glu Ala Arg Leu Glu Glu Ser Thr Asn Tyr Asn Gln Gln Leu
                980                 985                 990

Arg Gln Glu Leu Lys Thr Val Lys Lys Asn Tyr Glu Ala Leu Lys Gln
            995                 1000                1005

Arg Gln Asp Glu Glu Arg Met Val Gln Ser Ser Pro Pro Ile Ser
    1010                1015                1020

Gly Glu Asp Asn Lys Trp Glu Arg Glu Ser Gln Glu Thr Thr Arg
    1025                1030                1035

Glu Leu Leu Lys Val Lys Asp Arg Leu Ile Glu Val Glu Arg Asn
    1040                1045                1050

Asn Ala Thr Leu Gln Ala Glu Lys Gln Ala Leu Lys Thr Gln Leu
    1055                1060                1065

Lys Gln Leu Glu Thr Gln Asn Asn Asn Leu Gln Ala Gln Ile Leu
    1070                1075                1080

Ala Leu Gln Arg Gln Thr Val Ser Leu Gln Glu Gln Asn Thr Thr
    1085                1090                1095

Leu Gln Thr Gln Asn Ala Lys Leu Gln Val Glu Asn Ser Thr Leu
    1100                1105                1110

Asn Ser Gln Ser Thr Ser Leu Met Asn Gln Asn Ala Gln Leu Leu
    1115                1120                1125

Ile Gln Gln Ser Ser Leu Glu Asn Glu Asn Glu Ser Val Ile Lys
    1130                1135                1140

Glu Arg Glu Asp Leu Lys Ser Leu Tyr Asp Ser Leu Ile Lys Asp
    1145                1150                1155

His Glu Lys Leu Glu Leu Leu His Glu Arg Gln Ala Ser Glu Tyr
    1160                1165                1170

Glu Ser Leu Ile Ser Lys His Gly Thr Leu Lys Ser Ala His Lys
    1175                1180                1185

Asn Leu Glu Val Glu His Arg Asp Leu Glu Asp Arg Tyr Asn Gln
    1190                1195                1200

Leu Leu Lys Gln Lys Gly Gln Leu Glu Asp Leu Glu Lys Met Leu
    1205                1210                1215

Lys Val Glu Gln Glu Lys Met Leu Leu Glu Asn Lys Asn His Glu
    1220                1225                1230

Thr Val Ala Ala Glu Tyr Lys Lys Leu Cys Gly Glu Asn Asp Arg
    1235                1240                1245

Leu Asn His Thr Tyr Ser Gln Leu Leu Lys Glu Thr Glu Val Leu
    1250                1255                1260

Gln Thr Asp His Lys Asn Leu Lys Ser Leu Leu Asn Asn Ser Lys
    1265                1270                1275

Leu Glu Gln Thr Arg Leu Glu Ala Glu Phe Ser Lys Leu Lys Glu
    1280                1285                1290

Gln Tyr Gln Gln Leu Asp Ile Thr Ser Thr Lys Leu Asn Asn Gln
    1295                1300                1305

Cys Glu Leu Leu Ser Gln Leu Lys Gly Asn Leu Glu Glu Asn
    1310                1315                1320

Arg His Leu Leu Asp Gln Ile Gln Thr Leu Met Leu Gln Asn Arg
```

```
                    1325                1330                1335
Thr Leu Leu Glu Gln Asn Met Glu Ser Lys Asp Leu Phe His Val
            1340                1345                1350

Glu Gln Arg Gln Tyr Ile Asp Lys Leu Asn Glu Leu Arg Arg Gln
            1355                1360                1365

Lys Glu Lys Leu Glu Glu Lys Ile Met Asp Gln Tyr Lys Phe Tyr
            1370                1375                1380

Asp Pro Ser Pro Pro Arg Arg Gly Asn Trp Ile Thr Leu Lys
            1385                1390                1395

Met Arg Lys Leu Ile Lys Ser Lys Lys Asp Ile Asn Arg Glu Arg
            1400                1405                1410

Gln Lys Ser Leu Thr Leu Thr Pro Thr Arg Ser Asp Ser Ser Glu
            1415                1420                1425

Gly Phe Leu Gln Leu Pro His Gln Asp Ser Gln Asp Ser Ser Ser
            1430                1435                1440

Val Gly Ser Asn Ser Leu Glu Asp Gly Gln Thr Leu Gly Thr Lys
            1445                1450                1455

Lys Ser Ser Met Val Ala Leu Lys Arg Leu Pro Phe Leu Arg Asn
            1460                1465                1470

Arg Pro Lys Asp Lys Asp Lys Met Lys Ala Cys Tyr Arg Arg Ser
            1475                1480                1485

Met Ser Met Asn Asp Leu Val Gln Ser Met Val Leu Ala Gly Gln
            1490                1495                1500

Trp Thr Gly Ser Thr Glu Asn Leu Glu Val Pro Asp Asp Ile Ser
            1505                1510                1515

Thr Gly Lys Arg Arg Lys Glu Leu Gly Ala Met Ala Phe Ser Thr
            1520                1525                1530

Thr Ala Ile Asn Phe Ser Thr Val Asn Ser Ser Ala Gly Phe Arg
            1535                1540                1545

Ser Lys Gln Leu Val Asn Asn Lys Asp Thr Thr Ser Phe Glu Asp
            1550                1555                1560

Ile Ser Pro Gln Gly Val Ser Asp Asp Ser Ser Thr Gly Ser Arg
            1565                1570                1575

Val His Ala Ser Arg Pro Ala Ser Leu Asp Ser Gly Arg Thr Ser
            1580                1585                1590

Thr Ser Asn Ser Asn Asn Ala Ser Leu His Glu Val Lys Ala
            1595                1600                1605

Gly Ala Val Asn Asn Gln Ser Arg Pro Gln Ser His Ser Ser Gly
            1610                1615                1620

Glu Phe Ser Leu Leu His Asp His Glu Ala Trp Ser Ser Ser Gly
            1625                1630                1635

Ser Ser Pro Ile Gln Tyr Leu Lys Arg Gln Thr Arg Ser Ser Pro
            1640                1645                1650

Val Leu Gln His Lys Ile Ser Glu Thr Leu Glu Ser Arg His His
            1655                1660                1665

Lys Ile Lys Thr Gly Ser Pro Gly Ser Glu Val Val Thr Leu Gln
            1670                1675                1680

Gln Phe Leu Glu Glu Ser Asn Lys Leu Thr Ser Val Gln Ile Lys
            1685                1690                1695

Ser Ser Ser Gln Glu Asn Leu Leu Asp Glu Val Met Lys Ser Leu
            1700                1705                1710

Ser Val Ser Ser Asp Phe Leu Gly Lys Asp Lys Pro Val Ser Cys
            1715                1720                1725
```

| | | | | | | | | | | | |
|---|---|---|---|---|---|---|---|---|---|---|---|
|Gly|Leu|Ala|Arg|Ser|Val|Ser|Gly|Lys|Thr|Pro|Gly|Asp|Phe|Tyr|
| |1730| | | |1735| | | | |1740| | | | |
|Asp|Arg|Arg|Thr|Thr|Lys|Pro|Glu|Phe|Leu|Arg|Pro|Gly|Pro|Arg|
| |1745| | | |1750| | | | |1755| | | | |
|Lys|Thr|Glu|Asp|Thr|Tyr|Phe|Ile|Ser|Ser|Ala|Gly|Lys|Pro|Thr|
| |1760| | | |1765| | | | |1770| | | | |
|Pro|Gly|Thr|Gln|Gly|Lys|Ile|Lys|Leu|Val|Lys|Glu|Ser|Ser|Leu|
| |1775| | | |1780| | | | |1785| | | | |
|Ser|Arg|Gln|Ser|Lys|Asp|Ser|Asn|Pro|Tyr|Ala|Thr|Leu|Pro|Arg|
| |1790| | | |1795| | | | |1800| | | | |
|Ala|Ser|Ser|Val|Ile|Ser|Thr|Ala|Glu|Gly|Thr|Thr|Arg|Arg|Thr|
| |1805| | | |1810| | | | |1815| | | | |
|Ser|Ile|His|Asp|Phe|Leu|Thr|Lys|Asp|Ser|Arg|Leu|Pro|Ile|Ser|
| |1820| | | |1825| | | | |1830| | | | |
|Val|Asp|Ser|Pro|Pro|Ala|Ala|Ala|Asp|Ser|Asn|Thr|Thr|Ala|Ala|
| |1835| | | |1840| | | | |1845| | | | |
|Ser|Asn|Val|Asp|Lys|Val|Gln|Glu|Ser|Arg|Asn|Ser|Lys|Ser|Arg|
| |1850| | | |1855| | | | |1860| | | | |
|Ser|Arg|Glu|Gln|Gln|Ser|Ser| | | | | | | | |
| |1865| | | |1870| | | | | | | | | |

```
<210> SEQ ID NO 3
<211> LENGTH: 19
<212> TYPE: DNA
<213> ORGANISM: Artificial
<220> FEATURE:
<223> OTHER INFORMATION: Girdin siRNA Target sequece

<400> SEQUENCE: 3
gaaggagagg caactggat                                              19
```